US009163094B2

(12) United States Patent
Schmidt et al.

(10) Patent No.: US 9,163,094 B2
(45) Date of Patent: Oct. 20, 2015

(54) LIGHT-ACTIVATED FUSION PROTEINS AND USES THEREFOR

(71) Applicant: Massachusetts Institute of Technology, Cambridge, MA (US)

(72) Inventors: Daniel Schmidt, Cambridge, MA (US); Edward Boyden, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/629,335

(22) Filed: Sep. 27, 2012

(65) Prior Publication Data

US 2013/0116165 A1 May 9, 2013

Related U.S. Application Data

(60) Provisional application No. 61/539,480, filed on Sep. 27, 2011.

(51) Int. Cl.
| | |
|---|---|
| *A61K 38/00* | (2006.01) |
| *C12Q 1/02* | (2006.01) |
| *C12N 15/00* | (2006.01) |
| *C12N 5/07* | (2010.01) |
| *C12N 5/10* | (2006.01) |
| *C07K 1/00* | (2006.01) |
| *C07K 14/00* | (2006.01) |
| *C07K 17/00* | (2006.01) |
| *C07H 21/02* | (2006.01) |
| *C07K 19/00* | (2006.01) |
| *C07K 14/415* | (2006.01) |
| *A61K 38/01* | (2006.01) |

(52) U.S. Cl.
CPC ............... *C07K 19/00* (2013.01); *C07K 14/415* (2013.01); *A61K 38/011* (2013.01); *C07K 2319/02* (2013.01); *C07K 2319/03* (2013.01); *C07K 2319/035* (2013.01); *C07K 2319/55* (2013.01)

(58) Field of Classification Search
CPC ............. C07K 19/00; C07K 2319/035; C07K 2319/03; C07K 2319/55; C07K 2319/02; A61K 38/011
See application file for complete search history.

(56) References Cited

U.S. PATENT DOCUMENTS

| | | | |
|---|---|---|---|
| 6,699,677 | B1 | 3/2004 | Schall et al. |
| 8,202,699 | B2 | 6/2012 | Hegemann et al. |
| 2005/0239170 | A1 | 10/2005 | Hedley et al. |
| 2006/0057614 | A1 | 3/2006 | Heintz |
| 2010/0004162 | A1 | 1/2010 | Heintz et al. |
| 2012/0165204 | A1* | 6/2012 | Hahn et al. ............... 506/2 |

FOREIGN PATENT DOCUMENTS

WO      WO 00/17356      3/2000

OTHER PUBLICATIONS

Pham et al "A Synthetic Photoactivated Protein to Generate Local or Global Ca2+ Signals" Chem Biol 18:880-890. Published Jul. 29, 2011.*
Kreiter et al "Increased Antigen Presentation Efficiency by Coupling Antigens to MHC Class I Trafficking Signals" J Immunol 180:309-318. Published Jan. 1, 2008.*
Lisanti et al "Fusion proteins containing a minimal GPI-attachment signal are apically expressed in transfected MDCK cells" Cell Sci 99:637-640. Published 1991.*
Auer, et al., "Silencing neurotransmission with membrane—tethered toxins", Nature Methods, (Mar. 2010), vol. 7, No. 3, pp. 229-236.
Auer and Ibanez-Tallon, "The King is dead": Checkmating ion channels with tethered toxins, Toxicon, (2010), vol. 56, pp. 1293-1298.
Banghart et al., Light-activated ion channels for remote control of neuronal firing, Nature Neuroscience, (Dec. 2004), vol. 7, No. 12., pp. 1381-1386.
Bekkers and Delaney, Modulation of excitability by alpha-dendrotoxin-sensitive potassium channels in a neocortical pyramidal neurons, Journal of Neuroscience, (Sep. 2001), vol. 21, No. 17, pp. 6553-6560.
Blumenthal and Seibert, Voltage-gated sodium channel toxins: poisons, probes, and future promise, Cell Biochemistry Biophysics, (2003), vol. 38, pp. 215-238.
Boyden et al., Millisecond-timescale, genetically targeted optical control of neural activity, Nature Neuroscience, (Sep. 2005), vol. 8. No. 9., pp. 1263-1268.
Busskamp et al., Genetic reactivation of cone photoreceptors restores visual responses in retinitis pigmentosa, Science Jul. 23, 2010, vol. 329, No. 5990, pp. 413-417.
Chang, et al., Activation of Calcitonin Receptor and Calcitonin Receptor-like Receptor by Membrane-anchored Ligands, The Journal of Biological Chemistry, (Jan. 2010), vol. 285, No. 2., pp. 1075-1080.
Choi, et al., "Cellular Dissection of Circadian Peptide Signals with Genetically Encoded Membrane-Tethered Ligands", Current Biology, (Jul. 2009), vol. 19, pp. 1167-1175.
Chow et al., High-performance genetically targetable optical neural silencing by light-driven proton pumps, Nature Neuroscience, (Jan. 2010), vol. 463, No. 7277, pp. 98-102.
Christie, "Phototropin Blue-Light Receptors", Annual Review Plant Biology, (Oct. 2007), vol. 58, pp. 21-45.
Christie, et al., "Steric interactions stabilize the signaling state of the LOV2 domain of phototropin 1", Biochemistry, (2007), 46(32): 9310-9.
Corzo and Escoubas, "Pharmacologically active spider peptide toxins", CMLS Cellular and Molecular Life Science, (2003), vol. 60, pp. 2409-2426.
Ellis-Davies, Caged compounds: photorelease technology for control of cellular chemistry and physiology, Nature Methods, (Aug. 2007), vol. 4, No. 8., pp. 619-628.

(Continued)

*Primary Examiner* — Christina Bradley
*Assistant Examiner* — Zachary J Miknis
(74) *Attorney, Agent, or Firm* — Finch & Maloney PLLC

(57) ABSTRACT

The invention, in some aspects relates to synthetic, light-activated fusion proteins and their encoding polynucleotide molecules. In some aspects the invention additionally includes expression of the light-activated fusion proteins in cells and their use in methods such as therapeutic methods and candidate compound screening methods.

21 Claims, 6 Drawing Sheets

(56) References Cited

OTHER PUBLICATIONS

Fortin, et. al, "Membrane-tethered ligands are effective probes for exploring class B1 G protein-coupled receptor function", PNAS, dated (May 2009), vol. 106, No. 19, pp. 8049-8054.
Fortin, et al., "Discovery of Dual-Action Membrane-Anchored Modulators of Incretin Receptors", Plos One, (Sep. 2011), vol. 6, Issue 9, e24693, pp. 1-13.
Ferenczi and Deisseroth, "When the electricity (and the lights) go out: transient changes in excitability", Nature Neuroscience, (Jul. 2012), pp. 1058-1060, vol. 15, No. 8.
Gasparini et al., "Delineation of the functional site of alpha-dendrotoxin. The functional topographies of dendrotoxins are different but share a conserved core with those of other Kv1 potassium channel-blocking toxins", Journal of Biological Chemistry, (Sep. 1998), pp. 25393-25403, vol. 273, No. 39.
Gunning et al., "Nerve growth factor-induced differentiation of PC12 cells: evaluation of changes in RNA and DNA metabolism", Journal of Neuroscience, (Apr. 1981), pp. 368-379, vol. 1, No. 4.
Halliwell, et al., "Central action of dendrotoxin: selective reduction of a transient K conductance in hippocampus and binding to localized acceptors", Proc Natl Aced Sci, (1986), 83(2): 493-497.
Han et al., "Millisecond-timescale optical control of neural dynamics in the nonhuman primate brain", Neuron, dated (Apr. 2009), pp. 191-198, vol. 62, No. 2.
Han and Boyden, "Multiple-color optical activation, silencing, and desynchronization of neural activity, with single-spike temporal resolution", PLoS ONE, (Mar. 2007), vol. 2, No. 3.
Hara, et al., "Membrane-displayed peptide ligand activates the pheromone response pathway in Saccharomyces cerevisiae", The Journal of Biochemistry, (2012), 151(5), pp. 551-557.
Harper, et al., "Structural Basis of a Phototropin Light Switch", Science AAAS, (Sep. 2003), pp. 1541-1544, vol. 301.
Harvey, Twenty years of dendrotoxins, Toxicon, (Jan. 2001), vol. 39, No. 1, pp. 15-26.
He, et al., "ATDB: a uni-database platform for animal toxins", Nucleic Acids Research, (2008), vol. 36, Database Issue, D293-D297.
Holford, et al., "Manipulating neuronal circuits with endogenous and recombinant cell-surface tethered modulators", Frontiers in Molucular Neuroscience, (Oct. 2009), vol. 2, Article 21, pp. 1-10.
Ibanez-Tallon and Nitabach, "Tethering toxins and peptide ligands for modulation of neuronal function", Current Opinion in Neurobiology, (2012), vol. 22, pp. 72-78.
Ibanez-Tallon, et al., "Tethering Naturally Occuring Peptide Toxins for Cell-Autonomous Modulation of Ion Channels and Receptors In Vivo", Neuron, (Aug. 2004), vol. 43, pp. 305-311.
Kini and Doley, Structure, function and evolution of three-finger toxins: mini proteins with multiple targets, Toxicon, (Nov. 2010), pp. 855-867, vol. 56, No. 6.
Koh, et al., "Snake venom components and their applications in biomedicine", Cellular and Molecular Life Science, (Nov. 2006), vol. 63, pp. 3030-3041.
Lai and Jan, The distribution and targeting of neuronal voltage-gated ion channels, Nature Review Neuroscience, (Jul. 2006), pp. 548-562, vol. 7, No. 7.
Lim, et al., "T3DB: a comprehensively annotated database of common toxins and their targets", Nucleic Acids Research, (2010), vol. 38, Database issue, p. D781-D786.
Losi and Gärtner, "The evolution of flavin-binding photoreceptors: an ancient chromophore serving trendy blue-light sensors", Annu Rev Plant Bio, (2012), 63:49-72.
Losi and Gärtner, "Old chromophores, new photoactivation paradigms, trendy applications: flavins in blue light-sensing photoreceptors", Photochem Photobiol, 87(3): 491-510.
Lungu, et al., Designing photoswitchable peptides using the AsLOV2 domain, Chemical Biology, (2012), vol. 19, pp. 507-517.
Miesenböck, The optogenetic catechism, Science, (Oct. 2009), pp. 395-399, vol. 326.
Miesenböck, "Optogenetic control of cells and circuits", Annu Rev Cell Dev Biol, (2011), 27:731-58.
Möglich and Moffat, "Engineered photoreceptors as novel optogenetic tools", Photochem Photobiology Science, (2010), 9(10), pp. 1286-1300.
Möglich, et al., "Structure and Function of Plant Photoreceptors", Annual Review of Plant Biology, (Jan. 2010), vol. 61, pp. 21-47.
Näreoja, et al., "Glycosylphosphatidylinositol (GPI)-anchoring of mamba toxins enables cell-restricted receptor silencing", Biochemical and Biophysical Research Communications, dated (2012), vol. 417, pp. 93-97.
Nirthanan and Gwee, "Three-Finger $\alpha$-Neurotoxins and the Nicotinic Acetylcholine Receptor Forty Years On", Journal of Pharmacological Sciences, (2004), vol. 94, pp. 1-17.
Olivera, E.E. Just Lecture, 1996. Conus venom peptides, receptor and ion channel targets, and drug design: 50 million years of neuropharmacology, Molecular Biology of the Cell, (Nov. 1997), vol. 8, No. 11. pp. 2101-2109.
Raimondo, et al., "Optogenetic silencing strategies differ in their effects on inhibitory synaptic transmission", Nature Neuroscience, (Jun. 2012), vol. 15, No. 8., pp. 1102-1104.
Rashid, et al., "Hmrbase: a database of hormones and their receptors", BMC Genomics, (2009), 10:307, pp. 1-10.
Salomon, et al., "Photochemical and mutational analysis of the FMN-binding domains of the plant blue light receptor, phototropin." Biochemistry, (2000), 39(31): 9401-10.
Strickland, et al., "TULIPS: tunable, light-controlled interacting protein tags for cell biology", Nature Methods, (2012), vol. 9, pp. 379-384.
Stürzebecher, et al., "An in vivo tethered toxin approach for the cell-autonomous inactivation of voltage-gated sodium channel currents in nociceptors", The Journal of Physiology, (2010), vol. 588, pp. 1695-1707 and Supplemental Tables and Figures.
Terlau and Olivera, Conus venoms: a rich source of novel ion channel-targeted peptides, Physiological Reviews, (Jan. 2004), vol. 84, No. 1., pp. 41-68.
Vanhee, et al., "PepX: a structural database of non-redundant protein-peptide complexes", Nucleic Acids Research, (2009), vol. 38, Database Issue, pp. D545-D551.
Volgraf et al., Allosteric control of an ionotropic glutamate receptor with an optical switch, Nature Chemical Biology, (Jan. 2006), vol. 2. No. 1, pp. 47-52.
Wang, et al., "Spatiotemporal control of gene expression by a light-switchable transgene system", Nature Methods, (Mar. 2012), vol. 9, No. 3, pp. 266-271.
Wu, et al., "Phase Coupling of a Circadian Neuropeptide With Rest/Activity Rhythms Detected Using a Membrane-Tethered Spider Toxin", Plos Biology, (Nov. 2008), vol. 6, Issue 11, pp. 2512-2529, e273.
Yao, et al., "Estimation of the available free energy in a LOV2-J$\alpha$ photoswitch", Nature Chemical Biology, (Aug. 2008), vol. 4, No. 8, pp. 491-497.
Zamyatnin, et al., "The EROP—Moscow oligopeptide database", Nucleic Acids Research, (2006), vol. 34, Database issue, pp. D261-D266.
Zemelman et al., Photochemical gating of heterologous ion channels: remote control over genetically designated populations of neurons, Proceedings of the National Academy of Sciences, (Feb. 2003), pp. 1352-1357, vol. 110, No. 3, USA.
Zoltowski, et al., "Mechanism Based Tuning of a LOV Domain Photoreceptor", National Chemical Biology, (2009), 5(11), pp. 827-834.

* cited by examiner

Figure 1

SEQUENCE LISTING

```
<160> NUMBER OF SEQ ID NOS: 75

<210> SEQ ID NO 1
<211> LENGTH: 59
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Synthetic Peptide

<400> SEQUENCE: 1

Gln Pro Arg Arg Lys Leu Cys Ile Leu His Arg Asn Pro Gly Arg Cys
1               5                   10                  15

Tyr Asp Lys Ile Pro Ala Phe Tyr Tyr Asn Gln Lys Lys Lys Gln Cys
            20                  25                  30

Glu Arg Phe Asp Trp Ser Gly Cys Gly Gly Asn Ser Asn Arg Phe Lys
        35                  40                  45

Thr Ile Glu Glu Cys Arg Arg Thr Cys Ile Gly
    50                  55

<210> SEQ ID NO 2
<211> LENGTH: 62
<212> TYPE: PRT
<213> ORGANISM: Centruroides noxious

<400> SEQUENCE: 2

Met Lys Val Leu Ile Leu Ile Met Ile Ile Ala Ser Leu Met Ile Met
1               5                   10                  15

Gly Val Glu Met Asp Arg Asp Ser Cys Val Asp Lys Ser Arg Cys Ala
            20                  25                  30

Lys Tyr Gly Tyr Tyr Gln Glu Cys Gln Asp Cys Cys Lys Asn Ala Gly
        35                  40                  45
```

His Asn Gly Gly Thr Cys Met Phe Phe Lys Cys Lys Cys Ala
    50                  55                  60

<210> SEQ ID NO 3
<211> LENGTH: 57
<212> TYPE: PRT
<213> ORGANISM: Buthus eupeus

<400> SEQUENCE: 3

Met Lys Ile Ser Phe Val Leu Leu Leu Thr Leu Phe Ile Cys Ser Ile
1               5                   10                  15

Gly Trp Ser Glu Ala Arg Pro Thr Asp Ile Lys Cys Ser Glu Ser Tyr
            20                  25                  30

Gln Cys Phe Pro Val Cys Lys Ser Arg Phe Gly Lys Thr Asn Gly Arg
        35                  40                  45

Cys Val Asn Gly Phe Cys Asp Cys Phe
    50                  55

<210> SEQ ID NO 4
<211> LENGTH: 95
<212> TYPE: PRT
<213> ORGANISM: Bungarus multicinctus

<400> SEQUENCE: 4

Met Lys Thr Leu Leu Leu Thr Leu Val Val Thr Ile Val Cys Leu
1               5                   10                  15

Asp Leu Gly Tyr Thr Ile Val Cys His Thr Thr Ala Thr Ser Pro Ile
            20                  25                  30

Ser Ala Val Thr Cys Pro Pro Gly Glu Asn Leu Cys Tyr Arg Lys Met
        35                  40                  45

Trp Cys Asp Ala Phe Cys Ser Ser Arg Gly Lys Val Val Glu Leu Gly
    50                  55                  60

Cys Ala Ala Thr Cys Pro Ser Lys Lys Pro Tyr Glu Glu Val Thr Cys
65                  70                  75                  80

Cys Ser Thr Asp Lys Cys Asn Pro His Pro Lys Gln Arg Pro Gly
                85                  90                  95

<210> SEQ ID NO 5
<211> LENGTH: 76
<212> TYPE: PRT
<213> ORGANISM: Agelenopsis aperta

<400> SEQUENCE: 5

Ser Cys Ile Asp Ile Gly Gly Asp Cys Asp Gly Glu Lys Asp Asp Cys
1               5                   10                  15

Gln Cys Cys Arg Arg Asn Gly Tyr Cys Ser Cys Tyr Ser Leu Phe Gly
            20                  25                  30

Tyr Leu Lys Ser Gly Cys Lys Cys Val Val Gly Thr Ser Ala Glu Phe
        35                  40                  45

Gln Gly Ile Cys Arg Arg Lys Ala Arg Gln Cys Tyr Asn Ser Asp Pro
    50                  55                  60

Asp Lys Cys Glu Ser His Asn Lys Pro Lys Arg Arg
65                  70                  75

<210> SEQ ID NO 6
<211> LENGTH: 48
<212> TYPE: PRT
<213> ORGANISM: Agelenopsis aperta

<400> SEQUENCE: 6

-continued

```
Lys Lys Lys Cys Ile Ala Lys Asp Tyr Gly Arg Cys Lys Trp Gly Gly
1               5                   10                  15

Thr Pro Cys Cys Arg Gly Arg Gly Cys Ile Cys Ser Ile Met Gly Thr
                20                  25                  30

Asn Cys Glu Cys Lys Pro Arg Leu Ile Met Glu Gly Leu Gly Leu Ala
        35                  40                  45

<210> SEQ ID NO 7
<211> LENGTH: 35
<212> TYPE: PRT
<213> ORGANISM: Psalmopoeus cambridgei

<400> SEQUENCE: 7

Ser Glu Cys Arg Trp Phe Met Gly Gly Cys Asp Ser Thr Leu Asp Cys
1               5                   10                  15

Cys Lys His Leu Ser Cys Lys Met Gly Leu Tyr Tyr Cys Ala Trp Asp
                20                  25                  30

Gly Thr Phe
        35

<210> SEQ ID NO 8
<211> LENGTH: 34
<212> TYPE: PRT
<213> ORGANISM: Psalmopoeus cambridgei

<400> SEQUENCE: 8

Glu Cys Arg Trp Tyr Leu Gly Gly Cys Lys Glu Asp Ser Glu Cys Cys
1               5                   10                  15

Glu His Leu Gln Cys His Ser Tyr Trp Glu Trp Cys Leu Trp Asp Gly
                20                  25                  30

Ser Phe

<210> SEQ ID NO 9
<211> LENGTH: 36
<212> TYPE: PRT
<213> ORGANISM: Leiurus quinquestriatus

<400> SEQUENCE: 9

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
                20                  25                  30

Cys Leu Cys Arg
        35

<210> SEQ ID NO 10
<211> LENGTH: 27
<212> TYPE: PRT
<213> ORGANISM: Homo sapiens

<400> SEQUENCE: 10

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
                20                  25

<210> SEQ ID NO 11
<211> LENGTH: 28
<212> TYPE: PRT
<213> ORGANISM: Homo Sapiens
```

-continued

<400> SEQUENCE: 11

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 12
<211> LENGTH: 36
<212> TYPE: PRT
<213> ORGANISM: Homo sapiens

<400> SEQUENCE: 12

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 13
<211> LENGTH: 36
<212> TYPE: PRT
<213> ORGANISM: Rattus norvegicus

<400> SEQUENCE: 13

Tyr Pro Ala Lys Pro Glu Ala Pro Gly Glu Asp Ala Ser Pro Glu Glu
1               5                   10                  15

Leu Ser Arg Tyr Tyr Ala Ser Leu Arg His Tyr Leu Asn Leu Val Thr
            20                  25                  30

Arg Gln Arg Tyr
        35

<210> SEQ ID NO 14
<211> LENGTH: 10
<212> TYPE: PRT
<213> ORGANISM: Homo sapiens

<400> SEQUENCE: 14

Gly Asn Leu Trp Ala Thr Gly His Phe Met
1               5                   10

<210> SEQ ID NO 15
<211> LENGTH: 20
<212> TYPE: PRT
<213> ORGANISM: Homo sapiens

<400> SEQUENCE: 15

Ser Phe Arg Asn Gly Val Gly Thr Gly Met Lys Lys Thr Ser Phe Gln
1               5                   10                  15

Arg Ala Lys Ser
            20

<210> SEQ ID NO 16
<211> LENGTH: 39
<212> TYPE: PRT
<213> ORGANISM: Homo sapiens

<400> SEQUENCE: 16

Gln Glu Asp Ala Glu Leu Gln Pro Arg Ala Leu Asp Ile Tyr Ser Ala
1               5                   10                  15

```
Val Asp Asp Ala Ser His Glu Lys Glu Leu Ile Glu Ala Leu Gln Glu
            20                  25                  30

Val Leu Lys Lys Leu Lys Ser
            35

<210> SEQ ID NO 17
<211> LENGTH: 32
<212> TYPE: PRT
<213> ORGANISM: Homo sapiens

<400> SEQUENCE: 17

Tyr Gly Gly Phe Leu Arg Arg Ile Arg Pro Lys Leu Lys Trp Asp Asn
1               5                   10                  15

Gln Lys Arg Tyr Gly Gly Phe Leu Arg Arg Gln Phe Lys Val Val Thr
            20                  25                  30

<210> SEQ ID NO 18
<211> LENGTH: 29
<212> TYPE: PRT
<213> ORGANISM: Homo sapiens

<400> SEQUENCE: 18

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 19
<211> LENGTH: 11
<212> TYPE: PRT
<213> ORGANISM: Homo sapiens

<400> SEQUENCE: 19

Arg Pro Lys Pro Gln Gln Phe Phe Gly Leu Met
1               5                   10

<210> SEQ ID NO 20
<211> LENGTH: 9
<212> TYPE: PRT
<213> ORGANISM: Homo sapiens

<400> SEQUENCE: 20

Arg Pro Pro Gly Phe Ser Pro Phe Arg
1               5

<210> SEQ ID NO 21
<211> LENGTH: 10
<212> TYPE: PRT
<213> ORGANISM: Caenorhabditis elegans

<400> SEQUENCE: 21

Ser Ala Glu Pro Phe Gly Thr Met Arg Phe
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: REPEAT
<222> LOCATION: (1)..(3)
<223> OTHER INFORMATION: repeat of 1, 2, 3, 4, 5, 6, 7, 8, 9, or 10
      times
```

```
<400> SEQUENCE: 22

Gly Ser Gly Gly Ser Gly
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 23

Gly Ser Gly Gly Ser Gly Gly Ser Gly
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 24

Gly Ser Gly Gly Ser Gly Gly Ser Gly Gly Ser Gly
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 25

Gly Ser Gly Gly Ser Gly Gly Ser Gly Gly Ser Gly Gly Ser Gly
1               5                   10                  15

<210> SEQ ID NO 26
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 26

Gly Ser Gly Gly Ser Gly Gly Ser Gly Gly Ser Gly Gly Ser Gly Gly
1               5                   10                  15

Ser Gly

<210> SEQ ID NO 27
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 27

Gly Ser Gly Gly Ser Gly Gly Ser Gly Gly Ser Gly Gly Ser Gly Gly
1               5                   10                  15

Ser Gly Gly Ser Gly
            20

<210> SEQ ID NO 28
<211> LENGTH: 24
```

```
<212> TYPE: PRT
<213> ORGANISM: Artificial Sequence
<220> FEATURE:
<223> OTHER INFORMATION: Synthetic Peptide

<400> SEQUENCE: 28

Gly Ser Gly Gly Ser Gly Gly Ser Gly Gly Ser Gly Gly Ser Gly Gly
1               5                   10                  15

Ser Gly Gly Ser Gly Gly Ser Gly
            20

<210> SEQ ID NO 29
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 29

Gly Ser Gly Gly Ser Gly Gly Ser Gly Gly Ser Gly Gly Ser Gly Gly
1               5                   10                  15

Ser Gly Gly Ser Gly Gly Ser Gly Gly Ser Gly
            20                  25

<210> SEQ ID NO 30
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 30

Gly Ser Gly Gly Ser Gly Gly Ser Gly Gly Ser Gly Gly Ser Gly Gly
1               5                   10                  15

Ser Gly Gly Ser Gly Gly Ser Gly Gly Ser Gly Gly Ser Gly
            20                  25                  30

<210> SEQ ID NO 31
<211> LENGTH: 22
<212> TYPE: PRT
<213> ORGANISM: Artificial Sequence
<220> FEATURE:
<223> OTHER INFORMATION: Synthetic Peptide
<220> FEATURE:
<221> NAME/KEY: Repeat
<222> LOCATION: (1)..(22)
<223> OTHER INFORMATION: Region may be present 1, 2, 3, 4, 5 or more
      times

<400> SEQUENCE: 31

Ala Ala Ala Asp Tyr Lys Asp Asp Asp Asp Lys Ile Asp Ala Ala Ala
1               5                   10                  15

Gly Gly Ala Leu Cys Asn
            20

<210> SEQ ID NO 32
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 32

Ala Ala Ala Asp Tyr Lys Asp Asp Asp Asp Lys Ile Asp Ala Ala Ala
1               5                   10                  15
```

Gly Gly Ala Leu Cys Asn
            20

<210> SEQ ID NO 33
<211> LENGTH: 44
<212> TYPE: PRT
<213> ORGANISM: Artificial Sequence
<220> FEATURE:
<223> OTHER INFORMATION: Synthetic Peptide

<400> SEQUENCE: 33

Ala Ala Ala Asp Tyr Lys Asp Asp Asp Lys Ile Asp Ala Ala Ala
1               5                   10                  15

Gly Gly Ala Leu Cys Asn Ala Ala Asp Tyr Lys Asp Asp Asp
            20                  25                  30

Lys Ile Asp Ala Ala Ala Gly Gly Ala Leu Cys Asn
        35                  40

<210> SEQ ID NO 34
<211> LENGTH: 66
<212> TYPE: PRT
<213> ORGANISM: Artificial Sequence
<220> FEATURE:
<223> OTHER INFORMATION: Synthetic Peptide

<400> SEQUENCE: 34

Ala Ala Ala Asp Tyr Lys Asp Asp Asp Lys Ile Asp Ala Ala Ala
1               5                   10                  15

Gly Gly Ala Leu Cys Asn Ala Ala Ala Asp Tyr Lys Asp Asp Asp
            20                  25                  30

Lys Ile Asp Ala Ala Ala Gly Gly Ala Leu Cys Asn Ala Ala Ala Asp
        35                  40                  45

Tyr Lys Asp Asp Asp Lys Ile Asp Ala Ala Ala Gly Gly Ala Leu
        50                  55                  60

Cys Asn
65

<210> SEQ ID NO 35
<211> LENGTH: 88
<212> TYPE: PRT
<213> ORGANISM: Artificial Sequence
<220> FEATURE:
<223> OTHER INFORMATION: Synthetic Peptide

<400> SEQUENCE: 35

Ala Ala Ala Asp Tyr Lys Asp Asp Asp Lys Ile Asp Ala Ala Ala
1               5                   10                  15

Gly Gly Ala Leu Cys Asn Ala Ala Ala Asp Tyr Lys Asp Asp Asp
            20                  25                  30

Lys Ile Asp Ala Ala Ala Gly Gly Ala Leu Cys Asn Ala Ala Ala Asp
        35                  40                  45

Tyr Lys Asp Asp Asp Lys Ile Asp Ala Ala Ala Gly Gly Ala Leu
        50                  55                  60

Cys Asn Ala Ala Ala Asp Tyr Lys Asp Asp Asp Lys Ile Asp Ala
65                  70                  75                  80

Ala Ala Gly Gly Ala Leu Cys Asn
            85

<210> SEQ ID NO 36
<211> LENGTH: 110
<212> TYPE: PRT

```
<213> ORGANISM: Artificial Sequence
<220> FEATURE:
<223> OTHER INFORMATION: Synthetic Peptide

<400> SEQUENCE: 36

Ala Ala Ala Asp Tyr Lys Asp Asp Asp Lys Ile Asp Ala Ala
1               5                   10                  15

Gly Gly Ala Leu Cys Asn Ala Ala Asp Tyr Lys Asp Asp Asp
            20                  25                  30

Lys Ile Asp Ala Ala Ala Gly Gly Ala Leu Cys Asn Ala Ala Asp
        35                  40                  45

Tyr Lys Asp Asp Asp Lys Ile Asp Ala Ala Ala Gly Gly Ala Leu
    50                  55                  60

Cys Asn Ala Ala Ala Asp Tyr Lys Asp Asp Asp Lys Ile Asp Ala
65                  70                  75                  80

Ala Ala Gly Gly Ala Leu Cys Asn Ala Ala Asp Tyr Lys Asp Asp
                85                  90                  95

Asp Lys Ile Asp Ala Ala Ala Gly Gly Ala Leu Cys Asn
            100                 105                 110

<210> SEQ ID NO 37
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: Repeat
<222> LOCATION: (2)..(6)
<223> OTHER INFORMATION: Region may be present 2, 3, 4, 5, or more
      times

<400> SEQUENCE: 37

Ala Glu Ala Ala Ala Lys Ala
1               5

<210> SEQ ID NO 38
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 38

Ala Glu Ala Ala Ala Lys Glu Ala Ala Ala Lys Ala
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 39

Ala Glu Ala Ala Ala Lys Glu Ala Ala Ala Lys Glu Ala Ala Ala Lys
1               5                   10                  15

Ala

<210> SEQ ID NO 40
<211> LENGTH: 22
<212> TYPE: PRT
<213> ORGANISM: Artificial Sequence
<220> FEATURE:
```

<223> OTHER INFORMATION: Synthetic Peptide

<400> SEQUENCE: 40

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 41
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 41

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 42
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 42

Pro Pro Pro Trp
1

<210> SEQ ID NO 43
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 43

Pro Pro Pro Pro Trp
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 44

Pro Pro Pro Pro Pro Trp
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 45

Pro Pro Pro Pro Pro Pro Trp
1               5

```
<210> SEQ ID NO 46
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 46

Pro Pro Pro Pro Pro Pro Pro Trp
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 47

Pro Pro Pro Pro Pro Pro Pro Pro Trp
1               5

<210> SEQ ID NO 48
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 48

Pro Pro Pro Pro Pro Pro Pro Pro Pro Trp
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 49

Pro Pro Pro Pro Pro Pro Pro Pro Pro Pro Trp
1               5                   10

<210> SEQ ID NO 50
<211> LENGTH: 143
<212> TYPE: PRT
<213> ORGANISM: Avena sativa

<400> SEQUENCE: 50

Leu Ala Thr Thr Leu Glu Arg Ile Glu Lys Asn Phe Val Ile Thr Asp
1               5                   10                  15

Pro Arg Leu Pro Asp Asn Pro Ile Ile Phe Ala Ser Asp Ser Phe Leu
                20                  25                  30

Gln Leu Thr Glu Tyr Ser Arg Glu Glu Ile Leu Gly Arg Asn Cys Arg
            35                  40                  45

Phe Leu Gln Gly Pro Glu Thr Asp Arg Ala Thr Val Arg Lys Ile Arg
        50                  55                  60

Asp Ala Ile Asp Asn Gln Thr Glu Val Thr Val Gln Leu Ile Asn Tyr
65                  70                  75                  80

Thr Lys Ser Gly Lys Lys Phe Trp Asn Leu Phe His Leu Gln Pro Met
                85                  90                  95

Arg Asp Gln Lys Gly Asp Val Gln Tyr Phe Ile Gly Val Gln Leu Asp
                100                 105                 110
```

```
Gly Thr Glu His Val Arg Asp Ala Glu Arg Glu Gly Val Met Leu
        115                 120                 125
Ile Lys Lys Thr Ala Glu Asn Ile Asp Glu Ala Ala Lys Glu Leu
    130                 135                 140
```

<210> SEQ ID NO 51
<211> LENGTH: 150
<212> TYPE: PRT
<213> ORGANISM: Artificial Sequence
<220> FEATURE:
<223> OTHER INFORMATION: Synthetic Peptide

<400> SEQUENCE: 51

```
Val Arg Asp Ala Ala Glu Arg Glu Gly Val Met Leu Ile Lys Lys Thr
1               5                   10                  15
Ala Glu Asn Ile Asp Glu Ala Ala Lys Glu Leu Gly Gly Gly Ser Gly
            20                  25                  30
Gly Gly Leu Ala Thr Thr Leu Glu Arg Ile Glu Lys Asn Phe Val Ile
        35                  40                  45
Thr Asp Pro Arg Leu Pro Asp Asn Pro Ile Ile Phe Ala Ser Asp Ser
    50                  55                  60
Phe Leu Gln Leu Thr Glu Tyr Ser Arg Glu Glu Ile Leu Gly Arg Asn
65                  70                  75                  80
Cys Arg Phe Leu Gln Gly Pro Glu Thr Asp Arg Ala Thr Val Arg Lys
                85                  90                  95
Ile Arg Asp Ala Ile Asp Asn Gln Thr Glu Val Thr Val Gln Leu Ile
            100                 105                 110
Asn Tyr Thr Lys Ser Gly Lys Lys Phe Trp Asn Leu Phe His Leu Gln
        115                 120                 125
Pro Met Arg Asp Gln Lys Gly Asp Val Gln Tyr Phe Ile Gly Val Gln
    130                 135                 140
Leu Asp Gly Thr Glu His
145                 150
```

<210> SEQ ID NO 52
<211> LENGTH: 110
<212> TYPE: PRT
<213> ORGANISM: Neurospora crassa

<400> SEQUENCE: 52

```
Leu Ile Leu Cys Asp Leu Lys Gln Lys Asp Thr Pro Ile Val Tyr Ala
1               5                   10                  15
Ser Glu Ala Phe Leu Tyr Met Thr Gly Tyr Ser Asn Ala Glu Val Leu
            20                  25                  30
Gly Arg Asn Cys Arg Phe Leu Gln Ser Pro Asp Gly Met Val Lys Pro
        35                  40                  45
Lys Ser Thr Arg Lys Tyr Val Asp Ser Asn Thr Ile Asn Thr Met Arg
    50                  55                  60
Lys Ala Ile Asp Arg Asn Ala Glu Val Gln Val Glu Val Val Asn Phe
65                  70                  75                  80
Lys Lys Asn Gly Gln Arg Phe Val Asn Phe Leu Thr Met Ile Pro Val
                85                  90                  95
Arg Asp Glu Thr Gly Glu Tyr Arg Tyr Ser Met Gly Phe Gln
            100                 105                 110
```

<210> SEQ ID NO 53
<211> LENGTH: 21

<212> TYPE: PRT
<213> ORGANISM: Artificial Sequence
<220> FEATURE:
<223> OTHER INFORMATION: Synthetic Peptide

<400> SEQUENCE: 53

Met Val Pro Cys Thr Leu Leu Leu Leu Ala Ala Ala Leu Ala Pro
1               5                   10                  15

Thr Gln Thr Arg Ala
            20

<210> SEQ ID NO 54
<211> LENGTH: 29
<212> TYPE: PRT
<213> ORGANISM: Artificial Sequence
<220> FEATURE:
<223> OTHER INFORMATION: Synthetic Peptide

<400> SEQUENCE: 54

Met Asp Ser Lys Gly Ser Ser Gln Lys Gly Ser Arg Leu Leu Leu
1               5                   10                  15

Leu Val Val Ser Asn Leu Leu Leu Cys Gln Val Val Ser
            20                  25

<210> SEQ ID NO 55
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 55

Met Arg Gly Thr Pro Leu Leu Leu Val Val Ser Leu Phe Ser Leu Leu
1               5                   10                  15

Gln Asp

<210> SEQ ID NO 56
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 56

Met Ser Ala Leu Leu Ile Leu Ala Leu Val Gly Ala Ala Val Ala Asp
1               5                   10                  15

Tyr Lys Asp Asp Asp Asp Lys Leu
            20

<210> SEQ ID NO 57
<211> LENGTH: 30
<212> TYPE: PRT
<213> ORGANISM: Homo sapiens

<400> SEQUENCE: 57

Arg Ile Lys Phe Ser Thr Gly Ser His Cys His Gly Ser Phe Ser Leu
1               5                   10                  15

Ile Phe Leu Ser Leu Trp Ala Val Ile Phe Val Leu Tyr Gln
            20                  25                  30

<210> SEQ ID NO 58
<211> LENGTH: 27
<212> TYPE: PRT
<213> ORGANISM: Torpedo californica

<400> SEQUENCE: 58

Gly Glu Leu Ser Ser Ser Gly Thr Ser Ser Lys Gly Ile Ile Phe
1               5                   10                  15

Tyr Val Leu Phe Ser Ile Leu Tyr Leu Ile Phe
            20                  25

<210> SEQ ID NO 59
<211> LENGTH: 27
<212> TYPE: PRT
<213> ORGANISM: Rattus norvegicus

<400> SEQUENCE: 59

Leu Ala Arg Ser Ser Gly Val His Trp Ile Ala Ala Trp Leu Val Val
1               5                   10                  15

Thr Leu Ser Ile Ile Pro Ser Ile Leu Leu Ala
            20                  25

<210> SEQ ID NO 60
<211> LENGTH: 33
<212> TYPE: PRT
<213> ORGANISM: Homo sapiens

<400> SEQUENCE: 60

Ser Gly Thr Thr Ser Gly Thr Thr Arg Leu Leu Ser Gly His Thr Cys
1               5                   10                  15

Phe Thr Leu Thr Gly Leu Leu Gly Thr Leu Val Thr Met Gly Leu Leu
            20                  25                  30

Thr

<210> SEQ ID NO 61
<211> LENGTH: 28
<212> TYPE: PRT
<213> ORGANISM: Mus musculus

<400> SEQUENCE: 61

Tyr Leu Cys Asn Gly Ala Gly Phe Ala Thr Pro Val Thr Leu Ala Leu
1               5                   10                  15

Val Pro Ala Leu Leu Ala Thr Phe Trp Ser Leu Leu
            20                  25

<210> SEQ ID NO 62
<211> LENGTH: 51
<212> TYPE: PRT
<213> ORGANISM: Homo sapiens

<400> SEQUENCE: 62

Arg Asn Ala Val Gly Gln Asp Thr Gln Glu Val Ile Val Val Pro His
1               5                   10                  15

Ser Leu Pro Phe Lys Val Val Val Ile Ser Ala Ile Leu Ala Leu Val
            20                  25                  30

Val Leu Thr Ile Ile Ser Leu Ile Leu Ile Met Leu Trp Gln Lys
        35                  40                  45

Lys Pro Arg
    50

<210> SEQ ID NO 63
<211> LENGTH: 72
<212> TYPE: PRT
<213> ORGANISM: Rattus norvegicus

```
<400> SEQUENCE: 63

Gln Asp Pro Ser Thr Asp Ser Asn Met Glu Thr Thr Val Ile Tyr Val
1               5                   10                  15

Ile Leu Gly Ala Val Ala Met Ile Gly Ala Val Ala Ile Ile Gly Ala
            20                  25                  30

Met Val Ala Val Val Arg Arg Arg Lys Arg Asn Thr Gly Gly Lys Gly
        35                  40                  45

Gly Asp Tyr Ala Pro Ala Pro Gly Arg Asp Ser Ser Gln Ser Ser Asp
    50                  55                  60

Val Ser Leu Pro Asp Cys Lys Ala
65              70

<210> SEQ ID NO 64
<211> LENGTH: 45
<212> TYPE: PRT
<213> ORGANISM: Homo sapiens

<400> SEQUENCE: 64

Gln Asp Ile Ile Leu Tyr Trp Arg Asn Pro Thr Ser Ile Gly Ser Ile
1               5                   10                  15

Val Leu Ala Ile Ile Val Pro Ser Leu Leu Leu Leu Cys Leu Ala
            20                  25                  30

Leu Trp Tyr Met Arg Arg Arg Ser Tyr Gln Asn Ile Pro
        35                  40                  45

<210> SEQ ID NO 65
<211> LENGTH: 44
<212> TYPE: PRT
<213> ORGANISM: Homo sapiens

<400> SEQUENCE: 65

Gln Asp Ile Ile Leu Tyr Trp Gly His His Phe Ser Met Asn Trp Ile
1               5                   10                  15

Ala Leu Val Val Ile Val Pro Leu Val Ile Leu Val Leu Val Leu
            20                  25                  30

Trp Phe Lys Lys His Cys Ser Tyr Gln Asp Ile Leu
        35                  40

<210> SEQ ID NO 66
<211> LENGTH: 37
<212> TYPE: PRT
<213> ORGANISM: Mesobuthus tamulus

<400> SEQUENCE: 66

Gln Phe Thr Asp Val Asp Cys Ser Val Ser Lys Glu Cys Trp Ser Val
1               5                   10                  15

Cys Lys Asp Leu Phe Gly Val Asp Arg Gly Lys Cys Met Gly Lys Lys
            20                  25                  30

Cys Arg Cys Tyr Gln
        35

<210> SEQ ID NO 67
<211> LENGTH: 72
<212> TYPE: DNA
<213> ORGANISM: Mus musculus

<400> SEQUENCE: 67
atgagcgccc tgctgatcct ggccctggtg ggcgccgccg tggccgacta caaggacgac    60
gacgacaagc tg                                                       72
```

<210> SEQ ID NO 68
<211> LENGTH: 177
<212> TYPE: DNA
<213> ORGANISM: Artificial Sequence
<220> FEATURE:
<223> OTHER INFORMATION: Synthetic oligonucleotide

<400> SEQUENCE: 68
cagcccagaa gaaagctgtg catcctgcac agaaacccccg gcagatgcta cgacaagatc    60
cccgccttct actacaacca gaagaagaag cagtgcgaga gattcgactg gagcggctgc   120
ggcggcaaca gcaacagatt caagaccatc gaggagtgca agaacctg catcggc        177

<210> SEQ ID NO 69
<211> LENGTH: 66
<212> TYPE: DNA
<213> ORGANISM: Artificial Sequence
<220> FEATURE:
<223> OTHER INFORMATION: Synthetic Oligonucleotide

<400> SEQUENCE: 69
gccgccgccg actacaagga cgacgacgac aagatcgacg ccgccgccgg cggcgccctg    60
tgcaac                                                                66

<210> SEQ ID NO 70
<211> LENGTH: 429
<212> TYPE: DNA
<213> ORGANISM: Artificial Sequence
<220> FEATURE:
<223> OTHER INFORMATION: Synthetic Oligonucleotide

<400> SEQUENCE: 70
ttggctacta cacttgaacg tattgagaag aactttgtca ttactgaccc aagattgcca    60
gataatccca ttatattcgc gtccgatagt ttcttgcagt tgacagaata tagccgtgaa   120
gaaattttgg aagaaactg caggtttcta caaggtcctg aaactgatcg cgcgacagtg    180
agaaaaatta gagatgccat agataaccaa acagaggtca ctgttcagct gattaattat   240
acaaagagtg gtaaaaagtt ctggaacctc tttcacttgc agcctatgcg agatcagaag   300
ggagatgtcc agtactttat tggggttcag ttggatggaa ctgagcatgt ccgagatgct   360
gccgagagag agggagtcat gctgattaag aaaactgcag aaaatattga tgaggcggca   420
aaagaactt                                                            429

<210> SEQ ID NO 71
<211> LENGTH: 290
<212> TYPE: PRT
<213> ORGANISM: Artificial Sequence
<220> FEATURE:
<223> OTHER INFORMATION: Synthetic Peptide

<400> SEQUENCE: 71

Arg Val Ala Val Gly Gln Asp Thr Gln Glu Val Ile Val Val Pro His
1               5                   10                  15

Ser Leu Pro Phe Lys Val Val Val Ile Ser Ala Ile Leu Ala Leu Val
            20                  25                  30

Val Leu Thr Ile Ile Ser Leu Ile Ile Leu Ile Met Leu Trp Gln Lys
        35                  40                  45

Lys Pro Arg Arg Ile Arg Met Val Ser Lys Gly Glu Glu Asp Asn Met
    50                  55                  60

```
Ala Ile Ile Lys Glu Phe Met Arg Phe Lys Val His Met Glu Gly Ser
 65                  70                  75                  80

Val Asn Gly His Glu Phe Glu Ile Glu Gly Glu Gly Glu Gly Arg Pro
                 85                  90                  95

Tyr Glu Gly Thr Gln Thr Ala Lys Leu Lys Val Thr Lys Gly Gly Pro
            100                 105                 110

Leu Pro Phe Ala Trp Asp Ile Leu Ser Pro Gln Phe Met Tyr Gly Ser
        115                 120                 125

Lys Ala Tyr Val Lys His Pro Ala Asp Ile Pro Asp Tyr Leu Lys Leu
    130                 135                 140

Ser Phe Pro Glu Gly Phe Lys Trp Glu Arg Val Met Asn Phe Glu Asp
145                 150                 155                 160

Gly Gly Val Val Thr Val Thr Gln Asp Ser Ser Leu Gln Asp Gly Glu
                165                 170                 175

Phe Ile Tyr Lys Val Lys Leu Arg Gly Thr Asn Phe Pro Ser Asp Gly
            180                 185                 190

Pro Val Met Gln Lys Lys Thr Met Gly Trp Glu Ala Ser Ser Glu Arg
        195                 200                 205

Met Tyr Pro Glu Asp Gly Ala Leu Lys Gly Glu Ile Lys Gln Arg Leu
    210                 215                 220

Lys Leu Lys Asp Gly Gly His Tyr Asp Ala Glu Val Lys Thr Thr Tyr
225                 230                 235                 240

Lys Ala Lys Lys Pro Val Gln Leu Pro Gly Ala Tyr Asn Val Asn Ile
                245                 250                 255

Lys Leu Asp Ile Thr Ser His Asn Glu Asp Tyr Thr Ile Val Glu Gln
            260                 265                 270

Tyr Glu Arg Ala Glu Gly Arg His Ser Thr Gly Gly Met Asp Glu Leu
        275                 280                 285

Tyr Lys
    290

<210> SEQ ID NO 72
<211> LENGTH: 873
<212> TYPE: DNA
<213> ORGANISM: Artificial Sequence
<220> FEATURE:
<223> OTHER INFORMATION: Synthetic Oligonucleotide

<400> SEQUENCE: 72
cgagttgctg tgggccagga cacgcaggag gtcatcgtgg tgccacactc cttgcccttt      60
aaggtggtgg tgatctcagc catcctggcc ctggtggtgc tcaccatcat ctcccttatc     120
atcctcatca tgctttggca gaagaaacca cgtaggattc gtatggtgag caagggcgag     180
gaggataaca tggccatcat caaggagttc atgcgcttca aggtgcacat ggagggctcc     240
gtgaacggcc acgagttcga gatcgagggc gagggcgagg gccgccccta cgagggcacc     300
cagaccgcca agctgaaggt gaccaagggt ggccccctgc ccttcgcctg ggacatcctg     360
tcccctcagt tcatgtacgg ctccaaggcc tacgtgaagc accccgccga catccccgac     420
tacttgaagc tgtccttccc cgagggcttc aagtgggagc gcgtgatgaa cttcgaggac     480
ggcggcgtgg tgaccgtgac ccaggactcc tccctgcagg acggcgagtt catctacaag     540
gtgaagctgc gcggcaccaa cttcccctcc gacggccccg taatgcagaa gaagaccatg     600
ggctgggagg cctcctccga gcggatgtac cccgaggacg gcgccctgaa gggcgagatc     660
aagcagaggc tgaagctgaa ggacggcggc cactacgacg ctgaggtcaa gaccacctac     720
```

```
aaggccaaga agcccgtgca gctgcccggc gcctacaacg tcaacatcaa gttggacatc    780
acctcccaca acgaggacta caccatcgtg aacagtacg aacgcgccga gggccgccac    840
tccaccggcg gcatggacga gctgtacaag taa                                 873
```

<210> SEQ ID NO 73
<211> LENGTH: 227
<212> TYPE: PRT
<213> ORGANISM: Homo sapiens

<400> SEQUENCE: 73

```
Met Gly Ala Val Met Gly Thr Phe Ser Ser Leu Gln Thr Lys Gln Arg
1               5                   10                  15

Arg Pro Ser Lys Asp Ile Ala Trp Trp Tyr Gln Tyr Gln Arg Asp
            20                  25                  30

Lys Ile Glu Asp Glu Leu Glu Met Thr Met Val Cys His Arg Pro Glu
        35                  40                  45

Gly Leu Glu Gln Leu Glu Ala Gln Thr Asn Phe Thr Lys Arg Glu Leu
    50                  55                  60

Gln Val Leu Tyr Arg Gly Phe Lys Asn Glu Cys Pro Ser Gly Val Val
65                  70                  75                  80

Asn Glu Asp Thr Phe Lys Gln Ile Tyr Ala Gln Phe Phe Pro His Gly
                85                  90                  95

Asp Ala Ser Thr Tyr Ala His Tyr Leu Phe Asn Ala Phe Asp Thr Thr
            100                 105                 110

Gln Thr Gly Ser Val Lys Phe Glu Asp Phe Val Thr Ala Leu Ser Ile
        115                 120                 125

Leu Leu Arg Gly Thr Val His Glu Lys Leu Arg Trp Thr Phe Asn Leu
    130                 135                 140

Tyr Asp Ile Asn Lys Asp Gly Tyr Ile Asn Lys Glu Glu Met Met Asp
145                 150                 155                 160

Ile Val Lys Ala Ile Tyr Asp Met Met Gly Lys Tyr Thr Tyr Pro Val
                165                 170                 175

Leu Lys Glu Asp Thr Pro Arg Gln His Val Asp Val Phe Phe Gln Lys
            180                 185                 190

Met Asp Lys Asn Lys Asp Gly Ile Val Thr Leu Asp Glu Phe Leu Glu
        195                 200                 205

Ser Cys Gln Glu Asp Asp Asn Ile Met Arg Ser Leu Gln Leu Phe Gln
    210                 215                 220

Asn Val Met
225
```

<210> SEQ ID NO 74
<211> LENGTH: 1236
<212> TYPE: PRT
<213> ORGANISM: Homo sapiens

<400> SEQUENCE: 74

```
Met Ala Asn Gly Gly Gly Gly Gly Gly Ser Gly Gly Gly Gly
1               5                   10                  15

Gly Gly Gly Gly Ser Ser Leu Arg Met Ser Ser Asn Ile His Ala Asn
            20                  25                  30

His Leu Ser Leu Asp Ala Ser Ser Ser Ser Ser Ser Ser Ser Ser Ser
        35                  40                  45

Ser Ser Ser Ser Ser Ser Ser Ser Ser Ser Val His Glu Pro
    50                  55                  60
```

```
Lys Met Asp Ala Leu Ile Ile Pro Val Thr Met Glu Val Pro Cys Asp
 65                  70                  75                  80

Ser Arg Gly Gln Arg Met Trp Trp Ala Phe Leu Ala Ser Ser Met Val
             85                  90                  95

Thr Phe Phe Gly Gly Leu Phe Ile Ile Leu Leu Trp Arg Thr Leu Lys
            100                 105                 110

Tyr Leu Trp Thr Val Cys Cys His Cys Gly Gly Lys Thr Lys Glu Ala
        115                 120                 125

Gln Lys Ile Asn Asn Gly Ser Ser Gln Ala Asp Gly Thr Leu Lys Pro
    130                 135                 140

Val Asp Glu Lys Glu Glu Ala Val Ala Ala Glu Val Gly Trp Met Thr
145                 150                 155                 160

Ser Val Lys Asp Trp Ala Gly Val Met Ile Ser Ala Gln Thr Leu Thr
                165                 170                 175

Gly Arg Val Leu Val Leu Val Phe Ala Leu Ser Ile Gly Ala Leu
            180                 185                 190

Val Ile Tyr Phe Ile Asp Ser Ser Asn Pro Ile Glu Ser Cys Gln Asn
        195                 200                 205

Phe Tyr Lys Asp Phe Thr Leu Gln Ile Asp Met Ala Phe Asn Val Phe
    210                 215                 220

Phe Leu Leu Tyr Phe Gly Leu Arg Phe Ile Ala Ala Asn Asp Lys Leu
225                 230                 235                 240

Trp Phe Trp Leu Glu Val Asn Ser Val Val Asp Phe Phe Thr Val Pro
                245                 250                 255

Pro Val Phe Val Ser Val Tyr Leu Asn Arg Ser Trp Leu Gly Leu Arg
            260                 265                 270

Phe Leu Arg Ala Leu Arg Leu Ile Gln Phe Ser Glu Ile Leu Gln Phe
        275                 280                 285

Leu Asn Ile Leu Lys Thr Ser Asn Ser Ile Lys Leu Val Asn Leu Leu
    290                 295                 300

Ser Ile Phe Ile Ser Thr Trp Leu Thr Ala Ala Gly Phe Ile His Leu
305                 310                 315                 320

Val Glu Asn Ser Gly Asp Pro Trp Glu Asn Phe Gln Asn Asn Gln Ala
                325                 330                 335

Leu Thr Tyr Trp Glu Cys Val Tyr Leu Leu Met Val Thr Met Ser Thr
            340                 345                 350

Val Gly Tyr Gly Asp Val Tyr Ala Lys Thr Thr Leu Gly Arg Leu Phe
        355                 360                 365

Met Val Phe Phe Ile Leu Gly Gly Leu Ala Met Phe Ala Ser Tyr Val
    370                 375                 380

Pro Glu Ile Ile Glu Leu Ile Gly Asn Arg Lys Lys Tyr Gly Gly Ser
385                 390                 395                 400

Tyr Ser Ala Val Ser Gly Arg Lys His Ile Val Val Cys Gly His Ile
                405                 410                 415

Thr Leu Glu Ser Val Ser Asn Phe Leu Lys Asp Phe Leu His Lys Asp
            420                 425                 430

Arg Asp Asp Val Asn Val Glu Ile Val Phe Leu His Asn Ile Ser Pro
        435                 440                 445

Asn Leu Glu Leu Glu Ala Leu Phe Lys Arg His Phe Thr Gln Val Glu
    450                 455                 460

Phe Tyr Gln Gly Ser Val Leu Asn Pro His Asp Leu Ala Arg Val Lys
465                 470                 475                 480

Ile Glu Ser Ala Asp Ala Cys Leu Ile Leu Ala Asn Lys Tyr Cys Ala
```

```
            485                 490                 495
Asp Pro Asp Ala Glu Asp Ala Ser Asn Ile Met Arg Val Ile Ser Ile
            500                 505                 510
Lys Asn Tyr His Pro Lys Ile Arg Ile Ile Thr Gln Met Leu Gln Tyr
            515                 520                 525
His Asn Lys Ala His Leu Leu Asn Ile Pro Ser Trp Asn Trp Lys Glu
            530                 535                 540
Gly Asp Ala Ile Cys Leu Ala Glu Leu Lys Leu Gly Phe Ile Ala
545                 550                 555                 560
Gln Ser Cys Leu Ala Gln Gly Leu Ser Thr Met Leu Ala Asn Leu Phe
                565                 570                 575
Ser Met Arg Ser Phe Ile Lys Ile Glu Glu Asp Thr Trp Gln Lys Tyr
                580                 585                 590
Tyr Leu Glu Gly Val Ser Asn Glu Met Tyr Thr Glu Tyr Leu Ser Ser
                595                 600                 605
Ala Phe Val Gly Leu Ser Phe Pro Thr Val Cys Glu Leu Cys Phe Val
                610                 615                 620
Lys Leu Lys Leu Leu Met Ile Ala Ile Glu Tyr Lys Ser Ala Asn Arg
625                 630                 635                 640
Glu Ser Arg Ile Leu Ile Asn Pro Gly Asn His Leu Lys Ile Gln Glu
                645                 650                 655
Gly Thr Leu Gly Phe Phe Ile Ala Ser Asp Ala Lys Glu Val Lys Arg
                660                 665                 670
Ala Phe Phe Tyr Cys Lys Ala Cys His Asp Asp Ile Thr Asp Pro Lys
                675                 680                 685
Arg Ile Lys Lys Cys Gly Cys Lys Arg Pro Lys Met Ser Ile Tyr Lys
                690                 695                 700
Arg Met Arg Arg Ala Cys Cys Phe Asp Cys Gly Arg Ser Glu Arg Asp
705                 710                 715                 720
Cys Ser Cys Met Ser Gly Arg Val Arg Gly Asn Val Asp Thr Leu Glu
                725                 730                 735
Arg Ala Phe Pro Leu Ser Ser Val Ser Val Asn Asp Cys Ser Thr Ser
                740                 745                 750
Phe Arg Ala Phe Glu Asp Glu Gln Pro Ser Thr Leu Ser Pro Lys Lys
                755                 760                 765
Lys Gln Arg Asn Gly Gly Met Arg Asn Ser Pro Asn Thr Ser Pro Lys
                770                 775                 780
Leu Met Arg His Asp Pro Leu Leu Ile Pro Gly Asn Asp Gln Ile Asp
785                 790                 795                 800
Asn Met Asp Ser Asn Val Lys Lys Tyr Asp Ser Thr Gly Met Phe His
                805                 810                 815
Trp Cys Ala Pro Lys Glu Ile Glu Lys Val Ile Leu Thr Arg Ser Glu
                820                 825                 830
Ala Ala Met Thr Val Leu Ser Gly His Val Val Cys Ile Phe Gly
                835                 840                 845
Asp Val Ser Ser Ala Leu Ile Gly Leu Arg Asn Leu Val Met Pro Leu
                850                 855                 860
Arg Ala Ser Asn Phe His Tyr His Glu Leu Lys His Ile Val Phe Val
865                 870                 875                 880
Gly Ser Ile Glu Tyr Leu Lys Arg Glu Trp Glu Thr Leu His Asn Phe
                885                 890                 895
Pro Lys Val Ser Ile Leu Pro Gly Thr Pro Leu Ser Arg Ala Asp Leu
                900                 905                 910
```

```
Arg Ala Val Asn Ile Asn Leu Cys Asp Met Cys Val Ile Leu Ser Ala
            915                 920                 925

Asn Gln Asn Asn Ile Asp Asp Thr Ser Leu Gln Asp Lys Glu Cys Ile
        930                 935                 940

Leu Ala Ser Leu Asn Ile Lys Ser Met Gln Phe Asp Asp Ser Ile Gly
945                 950                 955                 960

Val Leu Gln Ala Asn Ser Gln Gly Phe Thr Pro Pro Gly Met Asp Arg
            965                 970                 975

Ser Ser Pro Asp Asn Ser Pro Val His Gly Met Leu Arg Gln Pro Ser
            980                 985                 990

Ile Thr Thr Gly Val Asn Ile Pro Ile Ile Thr Glu Leu Val Asn Asp
            995                 1000                1005

Thr Asn Val Gln Phe Leu Asp Gln Asp Asp Asp Asp Pro Asp
        1010                1015                1020

Thr Glu Leu Tyr Leu Thr Gln Pro Phe Ala Cys Gly Thr Ala Phe
    1025                1030                1035

Ala Val Ser Val Leu Asp Ser Leu Met Ser Ala Thr Tyr Phe Asn
        1040                1045                1050

Asp Asn Ile Leu Thr Leu Ile Arg Thr Leu Val Thr Gly Gly Ala
        1055                1060                1065

Thr Pro Glu Leu Glu Ala Leu Ile Ala Glu Glu Asn Ala Leu Arg
        1070                1075                1080

Gly Gly Tyr Ser Thr Pro Gln Thr Leu Ala Asn Arg Asp Arg Cys
        1085                1090                1095

Arg Val Ala Gln Leu Ala Leu Leu Asp Gly Pro Phe Ala Asp Leu
        1100                1105                1110

Gly Asp Gly Gly Cys Tyr Gly Asp Leu Phe Cys Lys Ala Leu Lys
        1115                1120                1125

Thr Tyr Asn Met Leu Cys Phe Gly Ile Tyr Arg Leu Arg Asp Ala
        1130                1135                1140

His Leu Ser Thr Pro Ser Gln Cys Thr Lys Arg Tyr Val Ile Thr
        1145                1150                1155

Asn Pro Pro Tyr Glu Phe Glu Leu Val Pro Thr Asp Leu Ile Phe
        1160                1165                1170

Cys Leu Met Gln Phe Asp His Asn Ala Gly Gln Ser Arg Ala Ser
        1175                1180                1185

Leu Ser His Ser Ser His Ser Ser Gln Ser Ser Lys Lys Ser
        1190                1195                1200

Ser Ser Val His Ser Ile Pro Ser Thr Ala Asn Arg Gln Asn Arg
        1205                1210                1215

Pro Lys Ser Arg Glu Ser Arg Asp Lys Gln Lys Tyr Val Gln Glu
        1220                1225                1230

Glu Arg Leu
        1235

<210> SEQ ID NO 75
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 75

Arg Val Ala Val Gly Gln Asp Thr Gln Glu Val Ile Val Val Pro His
1               5                   10                  15
```

```
Ser Leu Pro Phe Lys Val Val Val Ile Ser Ala Ile Leu Ala Leu Val
                20              25              30

Val Leu Thr Ile Ile Ser Leu Ile Leu Ile Met Leu Trp Gln Lys
            35              40              45

Lys Pro Arg Arg Ile Arg
        50
```

LIGHT-ACTIVATED FUSION PROTEINS AND USES THEREFOR

RELATED APPLICATIONS

This application claims the benefit under 35 U.S.C. §119 (e) of U.S. Provisional application Ser. No. 61/539,480 filed Sep. 27, 2011, the disclosure of which is incorporated by reference herein in its entirety.

GOVERNMENT INTEREST

This invention was made with government support under Grant Nos. OD002002, MH088182, DA029639 and NS075421 awarded by the National Institutes of Health and under Contract No. HR0011-12-C-0068 awarded by the Defense Advanced Research Projects Agency. The United States government has certain rights in the invention.

FIELD OF THE INVENTION

The invention, in some aspects relates to light-activated fusion proteins and their encoding polynucleotide; methods of making the light-activated fusion proteins; and methods of using the light-activated fusion proteins in methods such as research and therapeutic applications.

BACKGROUND OF THE INVENTION

The recently emerged framework of optogenetic technology combines optical and genetic tools to use light for controlling the activity of electrically excitable cell in a cell-targeted, cell-autonomous with millisecond temporal resolution (Miesenböck, G., (2009) Science 326, 395-399). Some technologies rely on chemical means through direct targeting of endogenous channels and receptors with caged signaling molecules, such as glutamate that are biologically inert until they become uncaged by the application of a light pulse. (Zemelman et al., (2003) Proc Natl Acad Sci USA 100, 1352-1357; and Ellis-Davies, G. C. R., (2007) Nat Methods 4, 619-628). These reagents do not allow for consecutive stimulation, they have little cellular specificity and force the researcher to target the treated brain regions based on anatomical rather than function considerations. Several groups have pioneered the use of photoisomerizable groups and reverse-engineered ion channels as light-controlled switches for vastly improved specificity and cycling properties (Banghart, M. et al., (2004) Nat Neurosci 7, 1381-1386; and Volgraf, M. et al., (2006) Nat Chem Biol 2, 47-52). While promising, the need for access to chemical expertise has hindered the widespread adoption of these reagents. However, most optogenetic technology takes the form of genetically encoded photoreceptors, microbial opsins such as Channelrhodopsin and Halorhodopsin that conduct or pump ions in a light-dependent manner and can be used without exogenously added chemical. Microbial opsins are not ion selective; they can therefore not be used to modulate a cell's $K^+$ independently from $Na^+$ conductance. They also do not allow the modulation of endogenous channels with analog precision.

Peptide neurotoxins and endogenous neuropeptides work by binding with extraordinarily high affinity and specificity to receptors in animal targets, that most of the time are proteins critical in neuronal signaling and muscle contraction. Because of this high affinity and specificity, peptide toxins have been used to identify and purify various receptors and channels, and are useful in study signaling pathways. Venomous animals produce biomolecule libraries that have evolved to paralyze prey by perturbing ion channel homeostasis. One major constituent of animal venoms are small peptide ligands, which are instrumental in ion channel research and have allowed scientists to probe the function of one of the most complex biological machines, the brain (Olivera, B. M., (1997) Mol Biol Cell 8, 2101-2109; Harvey, A. L., (2001) Toxicon 39, 15-26; Blumenthal, K. M. and Seibert, A. L., (2003) Cell Biochem Biophys 38, 215-238; Corzo, G. and Escoubas, P., (2003) Cell Mol Life Sci 60, 2409-2426; Nirthanan, S., and Gwee, M. C. E., (2004) J. Pharmacol. Sci. 94, 1-17; Terlau, H. and Olivera, B. M., (2004) Physiol Rev 84, 41-68; Koh, D. C. I. et al., (2006) Cell. Mol. Life Sci. 63, 3030-3041; and Kini, R. M. and Doley, R., (2010) Toxicon 56, 855-867). Toxins that target ion channels block either ion conduction through the channel pore or allosterically affect the channel's gating properties; however, their activity cannot be controlled by light.

SUMMARY OF THE INVENTION

The invention, in part, relates to synthetic light-activated polypeptides (also referred to herein as Lighands) and methods of their preparation and use. The invention also includes isolated nucleic acid sequences that encode light-activated synthetic polypeptides of the invention as well as vectors and constructs that comprise such nucleic acid sequences. In addition, the invention in some aspects includes expression of light-activated polypeptides in cells, tissues, and organisms as well as methods for using the light-activated polypeptides to alter cell and tissue function and for use in diagnosis and treatment of disorders and for screening candidate therapeutic compounds.

In some embodiments of this invention, optogenetic (light-activated, genetically encoded) molecules block ion conductances and modulate the gating of specific ion channels and receptors in a temporally precise and reversible way. This allows the perturbation of ion channel and receptor function in a reversible way, making it possible to alter specific cellular pathways, and then study their effects on normal and pathological biological functions.

According to one aspect of the invention, fusion proteins that include a peptide ligand domain, a linker polypeptide domain, and a photoreceptor polypeptide domain are provided. In some embodiments, the fusion protein further includes a membrane-anchoring polypeptide domain. In certain embodiments, the membrane is a plasma membrane. In some embodiments, the fusion protein also includes a trafficking signal polypeptide domain. In some embodiments, the trafficking signal is a secretion signal. In some embodiments, the fusion protein also includes a membrane-anchoring polypeptide domain and a secretion signal polypeptide domain. In certain embodiments, the membrane is a plasma membrane. In some embodiments, the peptide ligand is a ligand for an ion channel. In some embodiments, the ion channel is a potassium channel, a sodium channel, a nicotinic acetylcholine receptor channel, a calcium channel, a transient receptor potential (Trp) channel, a chloride channel, or an NMDA receptor. In certain embodiments, the membrane-anchoring polypeptide domain includes a glycophosphatidylinositol (GPI) anchoring polypeptide, a one-pass transmembrane polypeptide, a channel complex-anchoring polypeptide, or a channel complex partner anchoring polypeptide. In some embodiments, the GPI anchoring polypeptide includes an amino acid sequence derived from a 5'-nucleotidase polypeptide, an acetylcholinesterase polypeptide, a CD48 polypeptide, a complement decay-accelerating factor polypeptide, or a lynx-1 polypeptide. In some embodiments, the GPI anchoring polypeptide includes an amino acid sequence set forth as SEQ ID NO:57, SEQ ID NO:58, SEQ ID NO:59, SEQ ID NO:60, or SEQ ID NO:61. In some embodiments, the one-pass transmembrane polypeptide includes an amino acid sequence derived from an amino acid sequence of a platelet-derived-growth factor (PDGF) receptor polypeptide, a major histocompatibility Complex I polypeptide, a CD1b polypeptide, or a CD1c polypeptide. In certain embodiments, the one-pass transmembrane polypeptide includes an amino acid sequence set forth as SEQ ID NO:62, SEQ ID NO:63, SEQ ID NO:64, or SEQ ID NO:65. In some embodiments, the channel complex-anchoring polypeptide includes an amino acid sequence derived from an amino acid sequence of a BKCA α polypeptide. In some embodiments, the BKCα polypeptide includes an amino acid sequence set forth as SEQ ID NO:74. In some embodiments, the channel complex partner anchoring polypeptide includes an amino acid sequence derived from an amino acid sequence of a KChip1 polypeptide. In certain embodiments, the KChip1 polypeptide includes an amino acid sequence set forth as SEQ ID NO:73. In some embodiments, the secretion signal polypeptide domain includes a polypeptide derived from a truncated MHC I antigen (ss) polypeptide, a prolactin (pr1) polypeptide, an achR beta subunit (acr) polypeptide, or a serine protease I (sr1) polypeptide. In some embodiments, the truncated MHC I antigen (ss) signal polypeptide includes the amino acid sequence set forth as SEQ ID NO:53, the prolactin (pr1) signal polypeptide includes the amino acid sequence set forth as SEQ ID NO:54; the achR beta subunit (acr) polypeptide includes the amino acid sequence set forth as SEQ ID NO:55; and the serine protease I (sr1) secretion signal polypeptide includes the amino acid sequence set forth as SEQ ID NO:56. In certain embodiments, the photoreceptor polypeptide domain includes an amino acid sequence derived from an amino acid sequence of a plant photoreceptor polypeptide. In some embodiments, the photoreceptor polypeptide domain includes an amino acid sequence derived from the amino acid sequence of an AsLOV2 polypeptide, a circular permutation of an AsLOV2 polypeptide; or a VIVID polypeptide. In some embodiments, the AsLOV2 polypeptide includes the amino acid sequence set forth as SEQ ID NO:50; the circular permutation of an AsLOV2 polypeptide includes the amino acid sequence set forth as SEQ ID NO:51; and the VIVID polypeptide includes the amino acid sequence set forth as SEQ ID NO:52. In some embodiments, the linker polypeptide domain includes a flexible linker. In certain embodiments, the flexible linker includes $(GSG)_n$ wherein n is equal to 1, 2, 3, 4, 5, 6, 7, 8, 9, or 10. In some embodiments, the linker polypeptide domain includes a linker that includes a FLAG tag, a helical-type linker, or a Type II polyproline helix linker. In some embodiments, the linker that includes a FLAG tag includes the amino acid sequence set forth as $(AAADYKDDDDKIDAAAGGALCN)_n$ wherein n is equal to 1, 2, 3, 4, or 5 (SEQ ID NO:31). In some embodiments, the helical-type linker includes the amino acid sequence $A(EAAAK)_nA$ wherein n is equal to 1, 2, 3, 4, or 5 (SEQ ID NO:37). In certain embodiments, the Type II polyproline helix linker includes the amino acid sequence $[Proline (P)]_n$-Tryptophan (W), wherein n is equal to 1, 2, 3, 4, 5, 6, 7, 8, 9, or 10. In some embodiments, the fusion protein also includes a reporter molecule polypeptide domain. In some embodiments, the reporter molecule polypeptide domain includes a fluorescent reporter polypeptide.

According to an aspect of the invention, compositions that include any fusion protein of the foregoing embodiments of the above-mentioned aspect of the invention are provided.

According to an aspect of the invention, cells that include any embodiment of a fusion protein of the above-mentioned aspect of the invention are provided. In some embodiments, the cell is in a subject. In certain embodiments, the cell is in culture. In some embodiments, the cell is an in vitro cell. In some embodiments, the cell is an excitable cell. In certain embodiments, the cell is a neuronal cell, a cardiac cell, a lymphocyte, a leukocyte; a glial cell, a neuroglial cell, a macroglial cell, an astrocyte, an oligodendrocyte, a Schwann cell, a microglial cell, an immortal cell, or a tumor cell.

According to an aspect of the invention, pharmaceutical compositions that include any embodiment of a fusion protein of an above-mentioned aspect of the invention are provided.

According to an aspect of the invention, an isolated membrane that includes any embodiment of a fusion protein of an above-mentioned aspect of the invention is provided.

According to an aspect of the invention, polynucleotides that encode any embodiment of a fusion protein of an above-mentioned aspect of the invention are provided.

According to an aspect of the invention, an expression vector that includes any embodiment of a polynucleotide of an above-mentioned aspect of the invention is provided.

According to an aspect of the invention, a cell that includes any embodiment of an expression vector of an above-mentioned aspect of the invention is provided. In some embodiments, the cell is in a subject. In some embodiments, the cell is in culture. In some embodiments, the cell is an in vitro cell. In certain embodiments, the cell is an excitable cell. In some embodiments, the cell is a neuronal cell, a cardiac cell, a lymphocyte, a leukocyte; a glial cell, a neuroglial cell, a macroglial cell, an astrocyte, an oligodendrocyte, a Schwann cell, a microglial cell, an immortal cell, or a tumor cell. In some embodiments, According to an aspect of the invention, a pharmaceutical composition that includes any embodiment of polynucleotide of an above-mentioned aspect of the invention is provided.

According to another aspect of the invention, methods of manufacturing a cell that includes a synthetic, light-modulated protein are provided. The methods include delivering to a cell a polynucleotide molecule that encodes a fusion protein that includes a polypeptide ligand domain, a linker polypeptide domain, and a photoreceptor polypeptide domain; and expressing in the cell the fusion protein encoded by the polynucleotide, wherein the expressed fusion protein includes a synthetic, light-modulated protein. In some embodiments, the polynucleotide molecule further encodes a membrane-anchoring polypeptide domain. In certain embodiments, the membrane-anchoring polypeptide domain is a plasma membrane-anchoring polypeptide domain. In some embodiments, the polynucleotide molecule further encodes a trafficking signal polypeptide domain. In some embodiments, the trafficking signal is a secretion signal. In certain embodiments, the polynucleotide molecule further includes a membrane-anchoring polypeptide domain and a secretion signal polypeptide domain. In some embodiments, the membrane-anchoring polypeptide domain is a plasma membrane-anchoring polypeptide domain. In some embodiments, the expressed polypeptide is anchored to a cell membrane. In some embodiments, the polynucleotide molecule also includes a membrane-anchoring polypeptide domain and a secretion signal polypeptide domain. In some embodiments, the synthetic, light-modulated protein is anchored to the external cell membrane. In certain embodiments, the cell is in a subject. In some embodiments, the cell is in culture. In some embodiments, the cell is an in vitro cell. In certain embodiments, the cell is an excitable cell. In some embodiments, the cell is a neuronal cell, a cardiac cell, a lymphocyte, a leukocyte; a glial cell, a neuroglial cell, a macroglial cell, an astrocyte, an oligodendrocyte, a Schwann cell, a microglial cell, an immortal cell, or a tumor cell. In some embodiments, the polynucleotide molecule that encodes the fusion protein is delivered to the cell by means of pharmaceutical composition that includes the polynucleotide molecule. In some embodiments, the subject has a neurological disease or condition, an immune system disease or condition, or a cardiovascular disease or condition. In certain embodiments, the disease or condition is Epilepsy, Drug-resistant Depression, Schizophrenia, Tachycardia, Bradycardia, Atrial fibrillation, LongQT syndrome, Glioblastoma, Medullablastoma, Neuroblastoma, Leukemia, or Lymphoma.

According to another aspect of the invention, methods of modulating a functional state of an ion channel in a cell membrane are provided. The methods include delivering to a cell that includes a cell membrane ion channel, a polynucleotide molecule that encodes a fusion protein that includes a polypeptide ligand domain, a linker polypeptide domain, and a photoreceptor polypeptide domain, wherein the ligand is a ligand for the ion channel; expressing in the cell the fusion protein encoded by the polynucleotide, wherein the resulting polypeptide includes a light-modulated synthetic polypeptide; and contacting the expressed light-modulated synthetic polypeptide with an effective dose of a light to modulate a conformation of the fusion protein, wherein the modulation of the conformation of the fusion protein alters a functional state of the ion channel in the membrane. In some embodiments, the polynucleotide molecule further encodes a membrane-anchoring polypeptide domain. In some embodiments, the membrane-anchoring polypeptide domain is a plasma membrane-anchoring polypeptide domain. In some embodiments, the polynucleotide molecule further encodes a trafficking signal polypeptide domain. In certain embodiments, the trafficking signal is a secretion signal. In some embodiments, the ion channel is in the plasma membrane of the cell. In some embodiments, the polynucleotide molecule further includes a membrane-anchoring polypeptide domain and a secretion signal polypeptide domain. In some embodiments, the membrane-anchoring polypeptide domain is a plasma membrane-anchoring polypeptide domain. In some embodiments, the expressed polypeptide is anchored to a cell membrane. In certain embodiments, the expressed synthetic, light-modulated protein is anchored to the plasma membrane. In some embodiments, the cell is in a subject. In some embodiments, the cell is in culture. In certain embodiments, the cell is an in vitro cell. In some embodiments, the cell is an excitable cell. In some embodiments, the cell is a neuronal cell, a cardiac cell, a lymphocyte, a leukocyte; a glial cell, a neuroglial cell, a macroglial cell, an astrocyte, an oligodendrocyte, a Schwann cell, a microglial cell, an immortal cell, or a tumor cell. In some embodiments, the polynucleotide molecule that encodes the fusion protein is delivered to the cell in a pharmaceutical composition. In certain embodiments, the subject has a neurological disease or condition, an immune system disease or condition, or a cardiovascular disease or condition. In some embodiments, the disease or condition is Epilepsy, Drug-resistant Depression, Schizophrenia, Tachycardia, Bradycardia, Atrial fibrillation, LongQT syndrome, Glioblastoma, Medullablastoma, Neuroblastoma, Leukemia, or Lymphoma. In some embodiments, altering a functional state of the ion channel includes increasing a conductive state of the channel. In certain embodiments, altering a functional state of the ion channel includes decreasing a conductive state of the channel. In some embodiments, the functional state of the channel is a conductive state. In some embodiments, the conductive state is from 0.1 up to 10%, 20%, 30%, 40%, 50%, 60%, 70%, 80%, 90%, to 100% of a maximum conductance for the channel. In certain embodiments, the functional state of the channel is a non-conductive state. In some embodiments, According to another aspect of the invention, methods of determining the effect of a candidate therapeutic compound on a functional state of an ion channel of a membrane are provided. The methods include delivering to a cell that includes a cell membrane ion channel, a polynucleotide molecule that encodes a fusion protein that includes a polypeptide ligand domain, a linker polypeptide domain, and a photoreceptor polypeptide domain, wherein the polypeptide ligand is a ligand for the ion channel; expressing in the cell the fusion protein encoded by the polynucleotide; contacting the cell with a candidate therapeutic compound; contacting the expressed fusion protein with a dose of a light effective to modulate a conformation of the fusion protein; determining the functional state of the ion channel; and comparing the determined functional state of the ion channel with a control functional state of the ion channel, wherein a difference between the determined functional state and the control functional state indicates an effect of the candidate therapeutic compound on the functional state of the ion channel. In some embodiments, the polynucleotide molecule further encodes a membrane-anchoring polypeptide domain. In some embodiments, the membrane-anchoring polypeptide domain is a plasma membrane-anchoring polypeptide domain. In certain embodiments, the polynucleotide molecule further encodes a trafficking signal polypeptide domain. In some embodiments, the trafficking signal is a secretion signal. In some embodiments, the ion channel is in the plasma membrane of the cell. In some embodiments, the polynucleotide molecule also includes a membrane-anchoring polypeptide domain and a secretion signal polypeptide domain. In some embodiments, the membrane-anchoring polypeptide domain is a plasma membrane-anchoring polypeptide domain. In certain embodiments, the expressed fusion protein is anchored to a cell membrane. In some embodiments, the expressed fusion protein is anchored to the plasma membrane. In some embodiments, the control functional state of the ion channel is the functional state of the ion channel not contacted with the candidate therapeutic compound. In certain embodiments, the control functional state of the ion channel is the functional state of the ion channel contacted with an effective dose of light but not contacted with the candidate therapeutic compound. In some embodiments, the therapeutic compound is a candidate for treatment of a neurological disease or condition, an immune system disease or condition, or a cardiovascular disease or condition. In some embodiments, the disease or condition is Epilepsy, Drug-resistant Depression, Schizophrenia, Tachycardia, Bradycardia, Atrial fibrillation, LongQT syndrome, Glioblastoma, Medullablastoma, Neuroblastoma, Leukemia, or Lymphoma. In some embodiments, the cell is in a subject. In certain embodiments, the cell is in culture. In some embodiments, the cell is an in vitro cell. In some embodiments, the cell is an excitable cell. In some embodiments, the cell is a neuronal cell, a cardiac cell, a lymphocyte, a leukocyte; a glial cell, a neuroglial cell, a macroglial cell, an astrocyte, an oligodendrocyte, a Schwann cell, a microglial cell, an immortal cell, or a tumor cell. In certain embodiments, the functional state of the channel is a conductive state. In some embodiments, the conductive state is from 0.1 up to 10%, 20%, 30%, 40%, 50%, 60%, 70%, 80%, 90%, to 100% of a maximum conductance for the channel. In some embodiments, the functional state of the channel is a non-conductive state. In certain embodiments, the effect of the candidate therapeutic compound on the functional state of the ion channel includes increasing a conductive state of the channel or maintaining a conductive state of the channel. In some embodiments, the effect of the candidate therapeutic compound on the functional state of the ion channel includes decreasing a conductive state of the channel.

BRIEF DESCRIPTION OF THE DRAWINGS

FIG. 1 provides schematic diagrams of two Lighands. FIG. 1A shows a schematic overview of Lighand fusion protein designs. Two different implementations are show with each having a secretion signal, peptide ligand, linker, photoreceptor switch, and membrane anchor. FIG. 1B shows a diagram depicting topology of expressed Lighands interacting with an ion channel or receptor target.

FIG. 2A provides recording traces showing that somatic current injection elicits one action potential. FIG. 2B and FIG. 2C show results after illumination with blue (455 nm) light demonstrating that the same somatic current injection elicits multiple action potentials; illustrating that the neuron is more excitable. FIG. 2D and FIG. 2E show that illumination with blue light decreases the firing threshold in neurons expressing the αDTX Lighand.

FIG. 3A is a photomicrograph showing PC12 cells express fusion proteins containing AsLOV2 and αDTX to the cell surface. FIG. 3B are traces showing whole cell K+ currents before (left traces), during (middle traces) and after (right traces) illumination with 500 µW/mm² blue (455 nm) light. The holding voltage −80 mV, and depolarization voltages ΔV 10 mV to +50 mV. FIG. 3C provides a graph showing normalized whole cell K+ currents in response to blue light illumination (bar) recorded in PC12 cells co-expressing αDTX Lighand with rKv1.2 or Shaker Kv. Error bars s.e.m., n=3. FIG. 3D is a graph of results illustrating that Lighands are responsive to blue (455 nm), but not green (565 nm) light. FIG. 3E shows graphs showing the dependence of apparent $\tau_{on}$ (left) and apparent $\tau_{off}$ (right) of whole cell K+ current modulation on illumination light power. Error bars s.e.m of fitted coefficient. FIG. 3F is a graph of whole cell current illustrating results of repeated modulation of whole cell K+ current with saturating illumination (indicated bars).

FIG. 4A is a graph showing results indicating the average ratio of whole cell K+ current before and during illumination with 500 µW/mm² for αDTX variants as a function of reported toxin affinity. Error bars s.e.m., n=7-20. Solid are simulated ratios assuming mutations affect solely the toxin association rate constant α (downward sloping line) or dissociation rate constant (upward sloping line). FIG. 4B shows mutated residues (darker residues) mapped on the αDTX crystal structure (1DTX).

FIG. 5A are traces showing action potentials elicited in cultured neurons under current clamp to −20 pA (black), +10 pA (red) and +50 pA (blue) before (left panel), during illumination (middle panel) and after cessation of illumination (right panel). FIG. 5B is a graph of results indicating normalized number of action potentials at rheobase current injection before, during and after illumination. Error bars s.e.m., n=11. FIG. 5C is a graph showing firing frequency under current clamp before, during and after illumination. Error bars s.e.m., n=15. FIG. 5D is a graph showing resting potential of cultured neurons mock transfected (black) and expressing αDTX lighand. Error bars s.e,m., n=6-15. FIG. 5E is a diagram showing results indicating that action potentials (dots) elicited during 1 sec current clamp to +55 pA were suppressed during illumination (vertical bar) and recovered after cessation of illumination. Irradiance set to 500 µW/mm² for all experiments.

FIG. 6A illustrates an overall domain structure of an embodiment of a Lighand. FIG. 6B shows the function principle: in the dart state the Jα helix is folded and bound to the LOV2 domain core. The movement of the toxin (ligand) is restricted. After illumination with blue light, the Jα helix unfolds and relieves conformation restriction, thus allowing the anchored (also referred to as tethered) toxin to bind to its binding site on its cognate channel or receptor.

DETAILED DESCRIPTION

Figure 2:
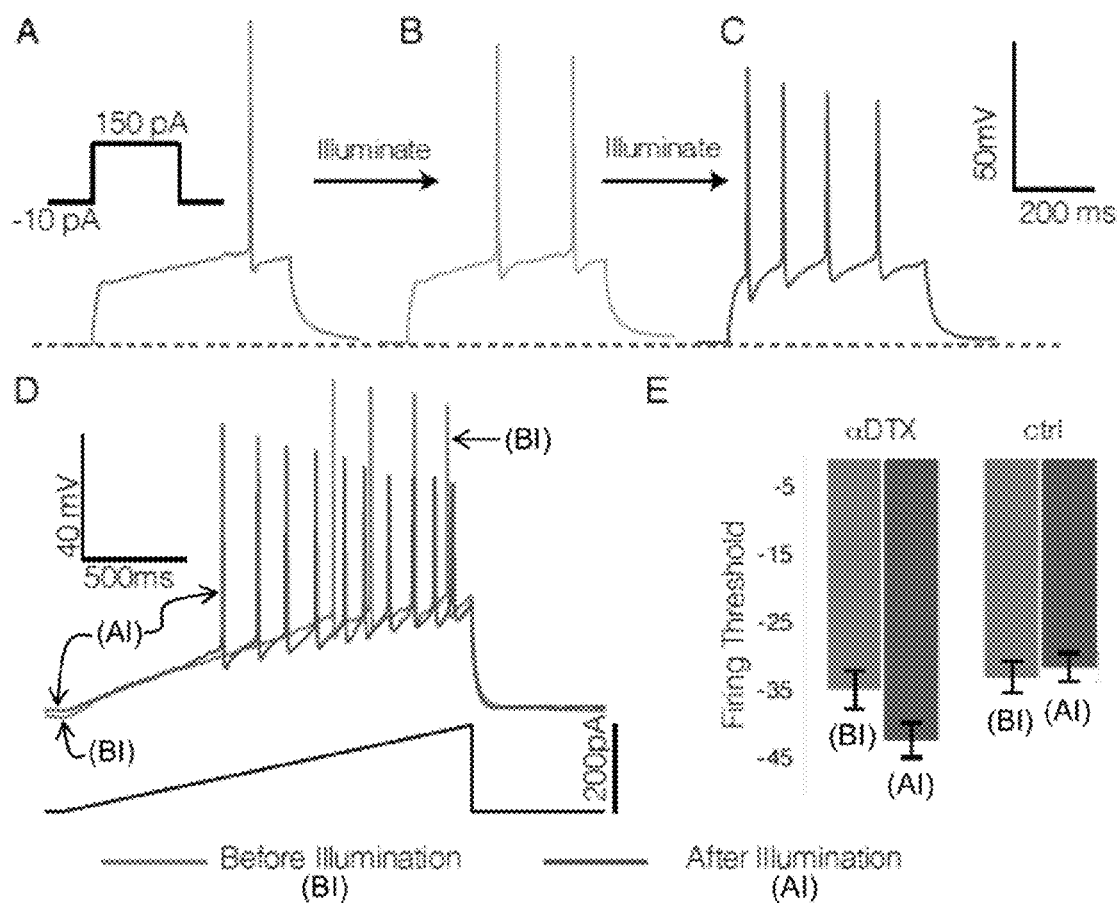
FIG. 2 shows recording traces and a graph illustrating control of neuronal excitability with light.

It has now been identified that fusion proteins that comprise a photoreceptor and a tethered peptide ligand can be prepared and used in a manner that permits the binding of the ligand at its cognate receptor or channel to be modulated by light, thus allowing the specific modulation of ion channels in cells with temporal and spatial control heretofore not used in biotechnology. Different subclasses of ion channels can be probed using different encoded peptide ligands without changes in methodology. Similarly, other polypeptide domains of a fusion protein of the invention can also be exchanged with different domains thus permitting more flexibility in their use. For example, a photoreceptor polypeptide that is modulated by contact with a particular wavelength of light may be substituted in a fusion protein of the invention with another photoreceptor polypeptide that is modulated by a different wavelength of light. This flexible aspect of fusion proteins of the invention is particularly promising for studying complex tissues such as the brain and other excitable tissues such as cardiac tissue, muscle, etc. The ability to optically perturb, modify, and/or control cellular function offers many advantages over physical manipulation mechanisms, such as speed, non-invasiveness, and the ability to easily span vast spatial scales from the nanoscale to macroscale.

The performance of synthetic light-modulated fusion proteins of the invention can be tuned for optimal use, particularly in context of their use in conjunction with other molecules or optical apparatus. For example, to study the perturbation of ion channels/receptors on different time scales, mutations can be introduced into light-modulated fusion protein of the invention that alter the intrinsic folding/unfolding kinetics and equilibrium of the linker polypeptides of the invention, and/or that alter the peptide toxin or ligand affinity to its binding site on its cognate channel or receptor.

Synthetic light-modulated fusion proteins of the invention, which are also referred to herein as "Lighands" can be used in a wide variety of applications. In a non-limiting example, Lighands of the invention can be used in drug discovery methods. The ability to block and/or modulate ion channels and receptor of cells, thus activating endogenous signaling pathways (such as calcium-dependent signaling, etc.), and then applying drugs that modulate the response of the cell (for example, using a calcium or voltage-sensitive dye), can be performed based on compositions and methods disclosed herein. Methods of the invention permit also new approaches and methods of drug screening and testing of candidate therapeutic compounds using light to 'stage' specific ion channel dysfunctions, and using just light to read out the effects of a candidate therapeutic compound one or more channels or receptors of interest. In another non-limiting example, Lighands of the invention can be used in prosthetic devices. For example, polynucleotides that express a Lighand of the invention can be delivered to a cell and/or subject and can be used in treatment applications in which the expressed ligand can be contacted with a dose of light effective to alter ion conductance in an excitable cell (for example, a heart cell, a brain cell, a neuron, etc.). Thus, methods of using Lighands of the invention permit ion channel conductance to be modulated (increased or decreased) to treat a disease or condition in which the ion conductance is abnormal and/or a disease or condition for which it is desirable to modulate (increase or decrease) ion conduction as a basis of a treatment.

Lighands of the invention represent a novel class of optogenetics tools that has now been created. These novel molecular reagents function in a cell-autonomous manner and permit study of the role and activities of ion channels and receptors with exquisite specificity, temporal resolution, and spatial resolution. In addition to the use of the now-identified light-modulated fusion proteins of the invention in cells to assess numerous types of naturally occurring ion channels, light-modulated fusion proteins of the invention may also be used to assess lab-generated ion channels and pumps that include, for example, microbial opsins such as Channelrhodopsin 2 (ChR2) and Halorhodopsin (Halo) or Archearhodopsin (Arch), as part of encoded light-dependent non-selective cation channels that are effective depolarizers or light-driven chloride/proton pumps that are potent hyperpolarizers. Thus, novel light-modulated fusion proteins of the invention (Lighands) provide powerful sets of genetically-encoded reagents for the precision control of neuronal activity that may be utilized for activity assays, drug discovery, and therapeutic applications.

Lighand compositions and methods of the invention can be used to assess various questions relating to ion conductivity and disease. Lighands of the invention can be used to assess types of ion channels and receptors are present in a neuron or other cell. Lighands can also be used in combination with other Lighands that include different polypeptide domains and can be used to perturb ion conduction of two or more ion channels and/or receptors independently from each other. Many channel and receptors are multigene products, that, through heteromeric assemblies, can give rise to functionally distinct ionic conductances (Lai, H. C. and Jan, L. Y., (2006) Nat Rev Neurosci 7, 548-562). Lighands of the invention are useful to overcome problems that limited the usefulness of prior optogenetic reagents, such as their lack of ability to target individual channels and receptors in a genetically encoded fashion, and drawbacks from overexpressing microbial opsins such as the alteration of alter ion-homeostasis (see for example, Raimondo, J. V. et al., (2012) Nat Neurosci 15, 1102-1104) and, related, changes in signaling characteristic such as increased rebound firing.

Light-modulated fusion proteins of the invention (Lighands) are designed in a manner to include (1) genetically encoded peptide ligands (e.g., toxins, etc.) that bind with high specificity to ion channels and alter the ion channel's functional properties and (2) photoreceptors that couple the absorption of photons to a conformational change (see for example, Harper, S. M., (2003) Science 301, 1541-1544; and Yao, X. et al., (2008) Nat Chem Biol 4, 491-497). In the resulting fusion protein, the photoreceptor's light-dependent conformation change can be used to modulate the activity of the peptide ligand. As used herein the term "ligand" refers to a polypeptide that binds to a cognate channel or receptor. A ligand may in some embodiments be a toxin.

A Lighand of the invention comprises three or more polypeptide domains. Three domains that are present in a Lighand of the invention are (1) a photoreceptor polypeptide domain; (2) a ligand polypeptide domain; and (3) a linker polypeptide domain that connects the photoreceptor polypeptide to the ligand polypeptide. Additional domains that may be included in a Lighand of the invention include, but are not limited to a trafficking signal polypeptide domain, a membrane-anchoring domain; a reporter polypeptide domain, etc.

In some embodiments a Lighand is expressed in a cell and remains in the cell. In certain embodiments the Lighand in a cell is localized to a membrane in the cell, for example a mitochondrial membrane, a nuclear membrane, etc. A signal polypeptide domain included in the Lighand may determine the localization of the Lighand in the cell. In certain embodiments of the invention, the Lighand may include a signal polypeptide domain that is a secretion domain and the resulting Lighand may be expressed in a cell and then secreted from the cell. In some embodiments of the invention, a Lighand may comprise a photoreceptor polypeptide domain, a linker polypeptide domain, a ligand polypeptide domain, a secretion polypeptide domain, and a membrane-anchoring domain and when expressed in a cell the Lighand may be secreted from the cell and anchored or tethered to the external side of the plasma membrane of the cell.

The ability to tailor a Lighand to include particular domains types and domain sequences permits the expression of a Lighand that comprises a ligand in a cell wherein the cell also includes the ligand's cognate channel or receptor. By contacting the photoreceptor of the Lighand with a dose of light effective to alter the conformation or folded state of the photoreceptor, it is possible to block (e.g., reduce) or activate (e.g., increase) conductance of ions across the channel or receptor. Lighands of the invention react to effective illumination with reasonably fast response times (seconds), thus allowing repeated activation/deactivation cycles, i.e. is reversible. The magnitude of light-induced block/activation in embodiments of the invention, i.e. the dynamic range, can be adjusted by increasing or decreasing Lighand characteristics such as relative ratios of ion channel/ligand polypeptide, association and dissociation rate constants of the ligand polypeptide, and the folding/unfolding kinetics of the photoreceptor domain, each of which can be readily determined using art-known methods. Ligands can be tailored to include polypeptide domains and sequences suitable for use in a variety of applications and the design of Lighands of the invention permits them to function with specific ligand-cognate interactions, with available light sources, etc. thus making them a flexible took for drug discovery and treatment methods.

The sequential order of the domains in a fusion protein of the invention as described, illustrated, or set forth herein is not intended to be limiting. The polypeptide domains of a fusion protein of the invention may be arranged in the order presented herein, or in another order that yields a fusion protein suitable for use in compositions and methods of the invention. Routine methods are known in the art to determine an order of domains and to prepare the resulting fusion protein. In addition, in certain embodiments of the invention, the number and amino acid sequence of each polypeptide domain type may be one, two, three, or more, depending on the type of domain and the desired function of the Lighand. For example, in some embodiments, there may be one, two, or more photoreceptor domains in a Lighand, and/or one, two, or more ligand polypeptide domains in a Lighand. Similarly, in some embodiments, there may be one, two, or more reporter molecule polypeptide domains, trafficking signal polypeptide domains, ligand domains and/or linker polypeptide domains in a Lighand of the invention. Routine methods known in the art may be used to prepare a fusion protein of the invention that includes a desired number of each domain type and the desired amino acid sequence for each domain polypeptide.

Polypeptide Ligand Domain

A fusion protein of the invention comprises a polypeptide ligand domain. The ligand may be a ligand that binds to an ion channel or receptor, for example to an ionotropic receptor.

As described herein, the polypeptide ligand domain is attached to the photoreceptor via a linker polypeptide domain and a change in conformation of the photoreceptor results in a change in proximity of the ligand to its cognate channel or receptor. In some embodiments, a ligand may become closer to its cognate ion channel or receptor due to the conformational change in the photoreceptor and in certain embodiments a ligand may be moved further from its cognate ion channel or receptor by a conformational change in the photoreceptor. In certain embodiments of the invention, a ligand (that is a domain of a Lighand of the invention) binds to its cognate ion channel or receptor when a conformational change in the photoreceptor increases the proximity of the ligand to its cognate ion channel or receptor. In certain embodiments of the invention, a ligand (that is a domain of a Lighand of the invention) does not bind to its cognate ion channel or receptor when a conformational change in the photoreceptor decreases the proximity of the ligand to its cognate ion channel or receptor. It will be understood that a conformational change may be a difference in the conformation of the photoreceptor when exposed to light as compared to the conformation of the photoreceptor when not exposed to the light. Thus, in some embodiments of the invention, a Lighand may be exposed to light and the resulting conformational change can alter the position and proximity of the ligand with respect to its cognate channel or receptor, resulting in binding of the ligand to its cognate channel or receptor or preventing binding of the ligand to its cognate channel or receptor, thereby altering the function (e.g., conductance of ions through) of the channel and/or receptor.

A ligand polypeptide that may be included in a fusion protein of the invention includes, but is not limited to, a ligand for a potassium channel, a sodium channel, a nicotinic acetylcholine receptor channel, a calcium channel, a transient receptor potential (Trp) channel, a chloride channel, a NMDA receptor, or a G-protein coupled receptor (GPCR).

Examples of polypeptide ligands for potassium channels that may be included in a fusion protein of the invention include, but are not limited to an AgTx2 sequence or derivative thereof; a CTX sequence or a derivative thereof; an αDTX sequence, a non-limiting example of which is a Dendroaspis angusticeps αDTX polypeptide comprising the amino acid sequence set forth as: QPRRKLCILHRNPGR-CYDKIPAFYYNQKKKQCERFDWSGCGGN-SNRFKTIEECR RTCIG (SEQ ID NO:1), or a derivative thereof; an Ergtx sequence, a non-limiting example of which is a Centruroides noxious Ergtx polypeptide comprising the amino acid sequence set forth as MKVLILIMI-IASLMIMGVEMDRDSCVDKSR-CAKYGYYQECQDCCKNAGHNGGT CMFFKCKCA (SEQ ID NO:2), or a derivative thereof; or a Bekm1 sequence, a non-limiting example of which is a Buthus eupeus Bekm1 polypeptide comprising the amino acid sequence set forth as MKISFVLLLTLFICSIGWSEARPTDIKC-SESYQCFPVCKSRFGKTNGRCVNGFCDC F (SEQ ID NO:3), or a derivative thereof.

Examples of polypeptide ligands for sodium channels that may be included in a fusion protein of the invention include, but are not limited to a μ-KIIIA AgTx2 sequence or derivative thereof μ-MrVIa sequence or derivative thereof, or an ATxII sequence or derivative thereof.

An example of a polypeptide ligand for nicotinic acetylcholine receptors that may be included in a fusion protein of the invention includes, but is not limited to an αBgtx sequence, a non-limiting example of which is a Bungarus multicinctus αBgtx polypeptide comprising the amino acid sequence set forth as MKTLLLTLVVVTIVCLDLGY-TIVCHTTATSPISAVTCPPGENLCYRKMWCDAFCS SRGKVVELGCAATCPSKKPYEEVTCCST-DKCNPHPKQRPG (SEQ ID NO:4), or a derivative thereof.

Examples of polypeptide ligands for calcium channels that may be included in a fusion protein of the invention include, but are not limited to a ω-AgaIIIA sequence, a non-limiting example of which is an Agelenopsis aperta ω-AgaIIIA polypeptide comprising the amino acid sequence set forth as SCIDIGGDCDGEKDDCQCCRRNGYCS-CYSLFGYLKSGCKCVVGTSAEFQGICRR KARQCYN-SDPDKCESHNKPKRR (SEQ ID NO:5), or a derivative thereof; or a w-AgaIVA sequence a non-limiting example of which is an Agelenopsis aperta ω-AgaIVA polypeptide comprising the amino acid sequence set forth as KKK-CIAKDYGRCKWGGTPCCRGRGCIC-SIMGTNCECKPRLIMEGLGLA (SEQ ID NO:6), or a derivative thereof.

Examples of polypeptide ligands for Transient Receptor Potential (Trp) channels that may be included in a fusion protein of the invention include, but are not limited to a VaTx1 sequence, a non-limiting example of which is a Psalmopoeus cambridgei VaTx1 polypeptide comprising the amino acid sequence set forth as SECRWFMGGCDSTLDCCKHLSCK-MGLYYCAWDGTF (SEQ ID NO:7), or a derivative thereof; a VaTx3 sequence, a non-limiting example of which is a Psalmopoeus cambridgei VaTx3 polypeptide comprising the amino acid sequence set forth as ECRWYLGGCKEDSEC-CEHLQCHSYWEWCLWDGSF (SEQ ID NO:8), or a derivative thereof.

Examples of polypeptide ligands for chloride channels that may be included in a fusion protein of the invention include, but are not limited to a Chlorotoxin sequence, a non-limiting example of which is a Leiurus quinquestriatus chlorotoxin polypeptide comprising the amino acid sequence set forth as MCMPCFTTDHQMARKCDDCCGGKGRGK-CYGPQCLCR (SEQ ID NO:9), or a derivative thereof.

Examples of polypeptide ligands for NMDA receptors that may be included in a fusion protein of the invention include, but are not limited to a GLYX-13 polypeptide or a derivative thereof. GLYX-13 is an antibody-derived tetrapeptide a so known as TPPT (see for example Moskal J. et al., (2005) Neuropharmacology December; 49(7):1077-87).

Examples of polypeptide ligands for GPCRs that may be included in a fusion protein of the invention include, but are not limited to a Pituitary adenylate cyclase activating polypeptides such as a PACAP27 polypeptide; a vasoactive intestinal peptide; a Neuropeptide Y polypeptide; a Neuropeptide YY polypeptide; a Neuromedin B polypeptide; a Neuropeptide S polypeptide; a Cocaine and amphetamine regulated transcript (CART) polypeptide; a Dynorphin polypeptide; a Glucagon polypeptide; a Substance P polypeptide a Bradykinin polypeptide; or a flp-class derivative polypeptide.

In some embodiments of the invention a fusion protein may comprise ligand polypeptide domain that includes a PACAP27 polypeptide. A non-limiting example of a PACAP27 signal polypeptide is set forth herein as HSDG-IFTDSYSRYRKQMAVKKYLAAVL (SEQ ID NO:10), or a derivative thereof.

In some embodiments of the invention a fusion protein may comprise ligand polypeptide domain that includes a Vasoactive intestinal peptide. A non-limiting example of a Vasoactive intestinal peptide signal polypeptide is set forth herein as HSDAVFTDNYTRLRKQMAVKKYLNSILN (SEQ ID NO:11), or a derivative thereof.

In some embodiments of the invention a fusion protein may comprise ligand polypeptide domain that includes a Neuropeptide Y polypeptide. A non-limiting example of a Neuropeptide Y signal polypeptide is set forth herein as YPSKPDNPGEDAPAEDMARYYSALRHYINLITRQRY (SEQ ID NO:12), or a derivative thereof.

In some embodiments of the invention a fusion protein may comprise ligand polypeptide domain that includes a Neuropeptide YY polypeptide. A non-limiting example of a Neuropeptide YY signal polypeptide is set forth herein as YPAKPEAPGEDASPEELSRYYASLRHYLNLVTRQRY (SEQ ID NO:13), or a derivative thereof.

In some embodiments of the invention a fusion protein may comprise ligand polypeptide domain that includes a Neuromedin B polypeptide. A non-limiting example of a Neuromedin B signal polypeptide is set forth herein as GNLWATGHFM (SEQ ID NO:14), or a derivative thereof.

In some embodiments of the invention a fusion protein may comprise ligand polypeptide domain that includes a Neuropeptide S polypeptide. A non-limiting example of a Neuropeptide S signal polypeptide is set forth herein as SFRNGVGTGMKKTSFQRAKS (SEQ ID NO:15), or a derivative thereof.

In some embodiments of the invention a fusion protein may comprise ligand polypeptide domain that includes a CART polypeptide. A non-limiting example of a CART signal polypeptide is set forth herein as QEDAELQPRALDIYSAVDDASHEK-ELIEALQEVLKKLKS (SEQ ID NO:16), or a derivative thereof.

In some embodiments of the invention a fusion protein may comprise ligand polypeptide domain that includes a Dynorphin polypeptide. A non-limiting example of a Dynorphin signal polypeptide is set forth herein as YGGFLRRIRPKLKWDNQKRYGGFLRRQFKVVT (SEQ ID NO:17), or a derivative thereof.

In some embodiments of the invention a fusion protein may comprise ligand polypeptide domain that includes a Glucagon polypeptide. A non-limiting example of a Glucagon signal polypeptide is set forth herein as HSQGTFTSDYSKYLDSRRAQDFVQWLMNT (SEQ ID NO:18), or a derivative thereof.

In some embodiments of the invention a fusion protein may comprise ligand polypeptide domain that includes a Substance P polypeptide. A non-limiting example of a Substance P signal polypeptide is set forth herein as RPKPQQFFGLM (SEQ ID NO:19), or a derivative thereof.

In some embodiments of the invention a fusion protein may comprise ligand polypeptide domain that includes a Bradykinin polypeptide. A non-limiting example of a Bradykinin signal polypeptide is set forth herein as RPPGFSPFR (SEQ ID NO:20), or a derivative thereof.

In some embodiments of the invention a fusion protein may comprise ligand polypeptide domain that includes an flp-class derivative polypeptide. A non-limiting example of a flp-class derivative signal polypeptide is set forth herein as SAEPFGTMRF (SEQ ID NO:21), or a derivative thereof.

It will be understood that the channels, receptors, and their ligand polypeptides listed herein are not intended to be limiting and that additional channel types can be modulated by a using a fusion protein of the invention that comprises a ligand polypeptide for the channel or receptor. In addition, the organism sources listed for the ligand sequences set forth herein are not intended to be limiting and ligand polypeptide sequences that are the same as or are derived from ligand sequences originating from the listed or other organisms may be used in compositions and methods of the invention. Additional channels and their polypeptide ligands (and sequences thereof) are well known in the art and may be included in a fusion protein of the invention [see for example U.S. Patent Application Publication No. US 2006/0057614; Ibanez-Tallon, I. et al., (2004) Neuron 43, 305-311; Holford, M. et al., (2009) Front Mol Neurosci 2, 21; Fortin, J. P. et al., (2009) Proc Natl Acad Sci USA 106, 8049-8054; Auer, S. et al., (2010) Nat Methods 7, 229-236; Stürzebecher, A. S. et al., (2010) J Physiol (Lond) 588, 1695-1707; He, Q. Y. et al. (2007) Nucleic Acids Res 36, D293-D297; Lim, E. et al., (2009) Nucleic Acids Res 38, D781-D786; Zamyatnin, A. A., (2006) Nucleic Acids Res, D261-D266, each of which is incorporated herein by reference]. Additional information regarding sequences for toxins and their cognate channels and receptors can be found at the Queensland Facility for Advanced Bioinformatics, Australia, (see: arachno-server.org); the Animal Toxin Database College of Life Sciences, Hunan Normal University, ChangSha, China (see pro-tchem.hunnu.edu.cn/toxin); and the Bioactive Peptide Database of the Data Analysis & Modeling Group at Hasselt University and Functional Genomics and Proteomics Unit at K.U. Leuven, Belgium, (see peptides.be).

Channels and Receptors

A ligand polypeptide included in a fusion protein of the invention may be selected to bind to and permit modulation of the conductivity across a particular channel or receptor, such as an ionotropic receptor. Thus, a ligand for a potassium channel may be selected for inclusion in a fusion protein to be expressed in a cell or tissue that includes potassium channels. The selection thus may be based on knowledge of the presence of a particular type of channel or receptor in a cell or membrane in which a fusion protein of the invention is to be expressed. Thus, the domain nature of fusion proteins of the invention permits flexibility in their use to assess different channels and receptors. Types of channels and receptors that may be assessed using a fusion protein of the invention include, but are not limited to, a potassium channel, a sodium channel, a nicotinic acetylcholine receptor channel, a calcium channel, a transient receptor potential (Trp) channel, a chloride channel, and an NMDA receptor. It is contemplated that fusion proteins of the invention may also be constructed to include a ligand domain to additional types of channels and/or receptors than those listed herein and that a skilled artisan will be able to selected and use a ligand for a channel or receptor in addition to those listed herein using routine procedures in conjunction with the teaching provided herein (see for example, Zamyatnin A. A., (2006) Nucleic Acids Res, 34 D261-D266; Rashid, M. et al., (2009) BMC Genomics 10(1): 307; and Vanhee, P. et al., (2009) Nucleic Acids Res 38 D545-51) For additional information on channel and receptor sequences see also the PepBank database maintained by Massachusetts General Hospital, Boston, Mass. and Harvard University, Cambridge, Mass. (see pepbank.mgh.harvard.edu/search/basic) and the Bioactive Peptide Database of the Data Analysis & Modeling Group at Hasselt University and Functional Genomics and Proteomics Unit at K.U. Leuven, Belgium, (see peptides.be).

Activity of a channel or receptor may be altered by a Lighand of the invention by the binding or lack of binding of a ligand to its cognate channel or receptor. Thus, using methods and fusion proteins of the invention, ion flow (e.g., conductance of ions) through a channel may be altered. For example, though not intended to be limiting, is an alternation in a functional state of a potassium channel by the binding to the potassium channel by a αDTX polypeptide linker of a fusion protein of the invention. As used herein, a fusion protein of the invention containing a ligand may be used in methods of altering a functional state of the ligand's cognate ion channel or receptor. In some embodiments, the term "altering" a functional state of an ion channel or receptor means increasing or decreasing conduction of ions through the channel or receptor. Thus, in some embodiments of the invention, altering a functional state of an ion channel or receptor includes decreasing a conductive state of the channel and may include decreasing ion passage through the channel. In certain embodiments of the invention, a conductive state of a channel or receptor is a state in which there is no ion conduction, thus, a non-conductive state. In certain embodiments, conduction across a channel or receptor (e.g., the conductive state of the channel or receptor) may be reduced but not eliminated entirely by a ligand of a fusion protein of the invention. Thus, in certain embodiments of the invention, the conductive state, or conduction of ions through the channel or receptor may be from 0.1% up to 10%, 20%, 30%, 40%, 50%, 60%, 70%, 80%, 90%, to 100% of a maximum possible conductance for the channel. In certain embodiments of the invention the functional state of a channel or receptor is a non-conductive state in which there is no significant conduction of ions across the channel or membrane.

In some embodiments of the inventions, a Lighand may be used to alter conductance through a channel or receptor and thereby alter the movement of ions into or out of a cell in which the Lighand is expressed, thus altering the cell's membrane potential. A non-limiting example of an ion conductance that can be altered by the activity of a Lighand of the invention is a chloride ion, potassium ion, a sodium ion, a calcium ion, etc.

Effects of light induced modulation a Lighand of the invention on conductance through a channel or receptor can be assessed using routine electrophysiological and imaging methods. For example, changes in conductance can be determined and measured using single cell recording in vitro [see for example, Sakmann, B. and Neher, E., (1984) Annu Rev Physiol 46, 455-472] and in vivo [see for example, Kodandaramaiah, S. B. et al., (2012) Nat Methods 9, 585-587], use of voltage-sensitive dyes [see for example Huang, C. J. et al., (2006) Nat Biotechnol 24, 439-446], and voltage-sensitive proteins [see for example, Akemann, W. et al., (2010) Nat Methods; and Kralj, J. M. et al., (2012) Nat Methods 9, 90-95]. In addition, downstream effects generated by altering (increasing or decreasing) ion conductance through channels or receptors may also be determined and/or measured as an indication of the effect of a Lighand on a function of an ion channel or receptor. Examples of downstream effects may include cell growth [see for example, Kleger, A. et al., (2010) Circulation 122, 1823], cell migration [see for example, Komuro, H. et al., (1996) Neuron 17, 275-285; and Soroceanu, L. et al., (1999) J Neurosci 19, 5942-5954], neurotransmitter release [see for example, Olivera, B. M. et al., (1994) Annu Rev Biochem 63, 823-867], cell death [see for example, Ishiuchi, S. et al., (2002) Nat Med 8, 971-978], and changes in gene expression [see for example, Desai, N. S. et al., (1999) Nat Neurosci 2, 515-520; Grubb, M. S. and Burrone, (2010) J. Nature 465, 1070-1074; and Grosse, G. et al., (2000) J Neurosci 20, 1869-1882].

Linker Polypeptide Domain

A fusion protein of the invention comprises a linker polypeptide domain that connects the ligand polypeptide domain to the photoreceptor polypeptide domain. A linker polypeptide of the invention may be flexible of a length that results in a desired alternation in the position of the ligand polypeptide with respect to a channel as a result of contacting the photoreceptor polypeptide with a dose of light. Thus, a conformational change in the fusion protein occurs upon contact of the photoreceptor polypeptide with an effective dose of light. Conformation change includes a change in the position of the ligand relative to the photoreceptor and/or channel or receptor.

Linker length and flexibility can be determined by the skilled artisan based, in part, on the desired function of the fusion protein. For example, in some embodiments, linker length and flexibility in the linker polypeptide domain result in a fusion protein that in the dark state. As used herein the term "dark state" refers to a state in which the photoreceptor of the fusion protein is not contacted with a dose of light effective to alter the conductivity of a channel or receptor by the fusion protein ligand. In such embodiments, the linker length and flexibility are such that in the dark state the ligand polypeptide is positioned to bind to its binding site on its cognate channel or receptor and thus alter the conductance of the channel or receptor. In certain embodiments, linker length and flexibility are such that in the dark state the ligand polypeptide is positioned such that it cannot bind to its binding site on its cognate ion channel or receptor and thus does not alter the conductance of the channel or receptor.

Although the binding kinetics and specificity of the ligand are independent of the photoreceptor polypeptide domain and the linker length, the conformational change (unfolding) of the photoreceptor polypeptide is induced by contact with an effective dose of light alters the proximity of the attached ligand to an ion channel or receptor present in the cell or membrane that includes the fusion protein. The linker polypeptide links the photoreceptor polypeptide with the ligand polypeptide, and the linker polypeptide and the attached ligand are affected by the folded or unfolded conformation of the photoreceptor. Thus, the light-induced folding or unfolding of the photoreceptor polypeptide modulates the ligand's position relative to the position of an ion channel or receptor that is present in the cell or membrane.

In some aspects of the invention a linker polypeptide domain may comprise a flexible linker. Examples of a flexible linker that may be used in fusion proteins of the invention include, but are not limited to $(GSG)_n$ where n=1, 2, 3, 4, 5, 6, 7, 8, 9, or 10. For example, GSGGSG (SEQ ID NO:22), GSGGSGGSG (SEQ ID NO:23), GSGGSGGSGGSG (SEQ ID NO:24), GSGGSGGSGGSGGSG (SEQ ID NO:25); GSGGSGGSGGSGGSGGSG (SEQ ID NO:26); GSGGSGGSGGSGGSGGSGGSG (SEQ ID NO:27); GSGGSGGSGGSGGSGGSGGSGGSG (SEQ ID NO:28); GSGGSGGSGGSGGSGGSGGSGGSGGSG (SEQ ID NO:29); or GSGGSGGSGGSGGSGGSGGSGGSGGSGGSG (SEQ ID NO:30).

In some embodiments of the invention a fusion protein may comprise linker polypeptide domain that includes a FLAG tag. An example of a linker that includes a flag tag and that may be used in a fusion protein of the invention includes, but is not limited to $(AAADYKDDDDKIDAAAGGALCN)_n$ (SEQ ID NO:31) where n=1, 2, 3, 4, or 5. For example, AAADYKDDDDKIDAAAGGALCN (SEQ ID NO:32);

AAADYKDDDDKIDAAAGGAL-
CNAAADYKDDDDKIDAAAGGALCN (SEQ ID NO:33);
AAADYKDDDDKIDAAAGGAL-
CNAAADYKDDDDKIDAAAGGALCNAAADYKD
DDDKIDAAAGGALCN (SEQ ID NO:34); AAADYKD-
DDDKIDAAAGGALCNAAADYKD-
DDDKIDAAAGGALCNAAADYKD DDDKIDAAAG-
GALCN (SEQ ID NO:35); or
AAADYKDDDDKIDAAAGGAL-
CNAAADYKDDDDKIDAAAGGALCNAAADYKD
DDDKIDAAAGGALCNAAADYKD-
DDDKIDAAAGGALCNAAADYKDDDDKIDA AAG-
GALCN (SEQ ID NO:36).

In certain embodiments of the invention a fusion protein may comprise a linker polypeptide domain that is a helical-type linker polypeptide. An example of a helical-type linker polypeptide that may be used in a fusion protein of the invention includes, but is not limited to A(EAAAK)$_n$A (SEQ ID NO:37) where n=2, 3, 4 or 5. For Example: AEAAAKEAAAKA (SEQ ID NO:38); AEAAAKEAAAKEAAAKA (SEQ ID NO:39); AEAAAKEAAAKEAAAKEAAAKA (SEQ ID NO:40); or AEAAAKEAAAKEAAAKEAAAKEAAAKA (SEQ ID NO:41).

In certain embodiments of the invention a fusion protein may comprise a linker polypeptide domain that is a Type II polyproline helix linker polypeptide. An example of a Type II polyproline helix linker polypeptide that may be used in a fusion protein of the invention includes but is not limited to (P)$_n$—W where n is 1, 2, 3, 4, 5, 6, 7, 8, 9, or 10. For example, PW, PPW, PPPW (SEQ ID NO:42); PPPPW (SEQ ID NO:43), PPPPPW (SEQ ID NO:44); PPPPPPW (SEQ ID NO:45); PPPPPPPW (SEQ ID NO:46), PPPPPPPPW (SEQ ID NO:47); PPPPPPPPPW (SEQ ID NO:48); or PPPPPPP-PPPW (SEQ ID NO:49).

It will be understood that the linker polypeptides listed herein are not intended to be limiting and that additional linker sequences may be included in a fusion protein of the invention. Additional linker polypeptides (and sequences thereof) are well known in the art and may be included in a fusion protein of the invention [see for example U.S. Patent Application Publication No. US 2006/0057614; Ibanez-Tallon, I. et al., (2004) Neuron 43, 305-311; Holford, M. et al., (2009) Front Mol Neurosci 2, 21; Fortin, J. P. et al. (2009) Proc Natl Acad Sci USA 106, 8049-8054; Auer, S. et al., (2010) Nat Methods 7, 229-236; Stürzebecher, A. S. et al., (2010) J Physiol (Lond) 588, 1695-1707; and Best, R. B. et al., (2007) Proc Natl Acad Sci USA 104, 18964-18969, each of which is incorporated in its entirety herein by reference]. Routine methods of selecting and optimizing linker based on length, flexibility, etc. are described in George, R. A. and Heringa, J., (2002) Protein Engineering 15, 871-879 and at the Linker Database at the Centre for Integrative Bioinformatics VU, University of Amsterdam, NL (see, ibi.vu.nl/programs/linkerdbwww/).

Photoreceptor Polypeptide Domain

A light-modulated fusion protein of the invention includes a photoreceptor polypeptide domain and when contacted with one or more pulses of light, a conformational change in the fusion protein results. When a fusion protein of the invention is expressed in a cell or membrane, light-induced conformational change in the fusion protein may alter a functional state of an ion channel that is also expressed in the cell or membrane. A light-activated fusion protein of the invention, also referred to herein as a "Lighand" can be expressed in specific cells, membranes, tissues, and/or organisms and used to alter the state of one or more ion channels in vivo, ex vivo, and in vitro in response to contacting the Lighand with a dose of suitable light.

When expressed in a cell or membrane, a Lighand of the invention can be activated by contacting the Lighand with a light having a pulse length, irradiance level, and wavelength suitable to activate the photoreceptor polypeptide domain. Selection of the wavelength can be based in part, on the identity of the photoreceptor polypeptide domain included in the Lighand. For example, engineered or naturally occurring photoreceptors that absorb photons and have a resulting conformational change are known in the art and can be used in compositions and methods of the invention. Examples of a variety of natural and engineered photoreceptors are described by Harper, S. M., (2003) Science 301, 1541-1544; Yao, X. et al., (2008) Nat Chem Biol 4, 491-497; Möglich, A. and Moffat, K., (2010) Photochem Photobiol Sci. October 28; 9(10):1286-300; Salomon, M. et al., (2000) Biochem 39, 9401-9410; Christie, J. M. et al., (2007) Biochem 46, 9310-9319; Zoltowski, BD et al., (2009) Nat Chem Biol November; 5(11):827-34; Miesenböck, G., (2011) Annu Rev Cell Dev Biol 27, 731-758; Losi, A. and Gartner, W., (2012) Annu Rev Plant Biol 63, 49-72; and Losi, A. and Gartner, W., (2011) Photochem Photobiol 87, 491-510.

Non-limiting examples photoreceptor domains that may be used in compositions and methods of the invention include photoreceptors such as an LOV2 receptor, including but not limited to AsLOV2 polypeptides, a circular permutation of an AsLOV2 polypeptide, and a VIVID polypeptide. Non-limiting examples of an AsLOV2 sequence, a circular permutation of an AsLOV2 sequence, and a VIVID sequence that may be used in a light-modulated fusion protein of the invention are set forth herein as SEQ ID NO:50, SEQ ID NO:51, and SEQ ID NO:52, respectively. Each of these polypeptide domains is a members of the LOV2 family and is extremely light sensitive, and may be activated by contact with little as 10 $\mu W/mm^2$. AsLOV2 polypeptide, circular permutation of an AsLOV2 polypeptide, or a VIVID polypeptide photoreceptors may be modulated by contacting the photoreceptor polypeptide with blue light having a wavelength of least 380 nm, 385 nm, 390 nm, 395 nm, 400 nm, 405 nm, 410 nm, 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, or 500 nm, including all wavelengths in the range. In some embodiments of the invention the wavelength of light used to modulate a photoreceptor that is a LOV2 family member or derivative thereof is at least 400 nm, 440 nm, 445 nm, 450 nm, 455 nm, 460 nm, or 465 nm.

It will be understood that a wavelength of light suitable to modulate a photoreceptor in a fusion protein of the invention, wherein the photoreceptor is not a LOV2-related photoreceptor, may be any wavelength that is determined to modulate that photoreceptor. Various means to determine a suitable wavelength with which to modulate a photoreceptor, as well as suitable wavelengths for use with specific photoreceptors are known in the art and can be used in conjunction with the teaching provided herein to select and confirm a wavelength of light for use in methods of the invention.

Parameters of a dose of light with which a fusion protein of the invention is contacted may also include the light's irradiance and pulse frequency in addition to the light's wavelength. In certain embodiments of the invention the irradiance in a dose of light with which a Lighand of the invention is contacted to modulate the Lighand is between 2 and 500 microwatts/mm$^2$ including every value within the listed range. In certain embodiments of the invention a dose of light with which a Lighand of the invention is contacted to modulate the Lighand may be a delivered as continuous pulse or at pulse frequency from 1 Hz-20 kHz including every value within the range. In some embodiments at least 1, 2, 3, 4, 5, 6, 7, 8, 9, 10, 15, 20, 30, 50, 100, 200, 300, 400, 500, 600, 700, 800, 900, 1000, or more pulses of light (including all numbers within the listed range) may be included in a dose of light that is applied to a photoreceptor domain of a fusion protein of the invention.

It will be understood that the photoreceptor polypeptides listed herein are not intended to be limiting and that alternative photoreceptor polypeptide sequences may be included in a fusion protein of the invention. Additional photoreceptor polypeptides (and sequences thereof) are known in the art and may be included in a fusion protein of the invention.

Signal Polypeptide Domains

In some embodiments of the invention, a light-modulated fusion protein of the invention (e.g., a Lighand) may include a signal polypeptide domain. A signal polypeptide domain may be a polypeptide comprising a trafficking signal that assists in the direction and/or delivery of a fusion protein of the invention to a particular location within or external to a cell in which it is expressed. In some embodiments of the invention a trafficking signal is a polypeptide sequence that assists in locating or directing a fusion protein of the invention to an internal cell structure such as the interior surface of the plasma membrane or to an internal cell membrane such as, but not limited to a mitochondrial membrane, an endoplasmic reticular membrane, a nuclear membrane, etc. a secretion signal. Thus, in some embodiments, a trafficking sequence may be a mitochondrial targeting sequence (MTS), an ER targeting sequence, etc. Internal cell membrane targeting sequences and their use in fusion proteins are well known in the art.

In certain embodiments of the invention, a trafficking signal that is included in a fusion protein of the invention is a secretion signal. In some embodiments of the invention, a secretion signal polypeptide domain comprises a polypeptide derived from a truncated MHC I antigen (ss) polypeptide, a prolactin (pr1) polypeptide, an achR beta subunit (acr) polypeptide, or a serine protease I (sr1) polypeptide.

In some embodiments of the invention a fusion protein may comprise secretion signal polypeptide domain that includes a truncated MHC I antigen polypeptide. A non-limiting example of a truncated MHC I antigen secretion signal polypeptide referred to as "ss" is set forth herein as MVPCTLLLLLAAALAPTQTRA (SEQ ID NO:53), or a derivative thereof.

In some embodiments of the invention a fusion protein may comprise secretion signal polypeptide domain that includes a prolactin polypeptide. A non-limiting example of a prolactin secretion signal polypeptide also referred to herein as "pr1" is set forth herein as MDSKGSSQKGSRLLLLLVVSNLLLCQVVS (SEQ ID NO:54), or a derivative thereof.

In some embodiments of the invention a fusion protein may comprise secretion signal polypeptide domain that includes an AchR beta subunit polypeptide. A non-limiting example of a AchR beta subunit secretion signal polypeptide, which is also referred to herein as "acr" is set forth herein as MRGTPLLLVVSLFSLLQD (SEQ ID NO:55), or a derivative thereof.

In some embodiments of the invention a fusion protein may comprise secretion signal polypeptide domain that includes a Serine protease I polypetpide with FLAG tag. A non-limiting example of a Serine protease I with FLAG tag secretion signal polypeptide, which is also referred to herein as "sr1" is set forth herein as MSALLILALVGAAVADYKDDDDKL (SEQ ID NO:56), or a derivative thereof.

It will be understood that the trafficking signal sequences, including intracellular and secretion signal polypeptides listed herein are not intended to be limiting and that additional trafficking signal sequences, such as intracellular and secretion signal polypeptides (and sequences thereof), etc. are well known in the art and may be included in a fusion protein of the invention [see for example U.S. Patent Application Publication No. US 2006/0057614; Ibanez-Tallon, I. et al., (2004) Neuron 43, 305-311; Holford, M. et al., (2009) Front Mol Neurosci 2, 21; Fortin, J. P. et al., (2009) Proc Natl Acad Sci USA 106, 8049-8054; Auer, S. et al., (2010) Nat Methods 7, 229-236; and Stürzebecher, A. S. et al., (2010) J Physiol (Lond) 588, 1695-1707]. Additional signal polypeptides (and sequences thereof) are known in the art and may be included in a fusion protein of the invention.

Methods of selecting and optimizing trafficking signal sequences for localization of polypeptide sequences in a cell, membrane, etc. are routine in the art, for example, see Emanuelsson, O., et al., (2000) J. Mol. Biol., 300: 1005-1016, and the TargetP 1.1 server of the Center for Biological Sequence Analysis (CBS), Dept of Systems Biology, Technical University of Denmark, Lyngby, Denmark (cbs.dtu.dk/services/TargetP/).

Membrane Tethering Signal

In some embodiments of the invention, a light-modulated fusion protein of the invention (e.g., a Lighand) may include a membrane-anchoring signal polypeptide domain. In some embodiments of the invention a membrane-anchoring polypeptide domain anchors other fusion protein domains to a plasma membrane. The plasma membrane may be the plasma membrane in a cell in which the fusion protein has been expressed. In some embodiments of the invention, a membrane-anchoring polypeptide domain may comprise a glycophosphatidylinositol (GPI) anchoring polypeptide, a one-pass transmembrane polypeptide, a channel complex-anchoring polypeptide, or a channel complex partner anchoring polypeptide.

A number of different GPI anchoring polypeptides are known in the art and may be used in a fusion protein of the invention. Non-limiting examples of amino acid sequences that in some embodiments of the invention may be added at the c-terminus of a fusion protein resulting in cleavage of the underlined residues and modification of the bold residue with the membrane anchor glycophosphatidylinositol, are provided. For example, a GPI anchoring polypeptide may comprise an amino acid sequence derived from a 5'-nucleotidase polypeptide, an acetylcholinesterase polypeptide, a CD48 polypeptide, a complement decay-accelerating factor polypeptide, or a lynx-1 polypeptide.

In some embodiments of the invention a fusion protein may comprise membrane-anchoring polypeptide domain that includes a 5'-nucleotidase polypeptide. A non-limiting example of a homo sapiens 5'-nucleotidase membrane-anchor polypeptide is set forth herein as RIKFS TGSHCHGSFSLIFLSLWAVIFVLYQ (SEQ ID NO:57), or a derivative thereof.

In some embodiments of the invention a fusion protein may comprise membrane-anchoring polypeptide domain that includes an acetylcholinesterase polypeptide. A non-limiting example of a Pacific electric ray acetylcholinesterase membrane-anchor polypeptide is set forth herein as GELSS SGTSSSKGIIFYVLFSILYLIF (SEQ ID NO:58), or a derivative thereof.

In some embodiments of the invention a fusion protein may comprise membrane-anchoring polypeptide domain that includes a CD48 polypeptide. A non-limiting example of a rattus norvegicus CD48 membrane-anchor polypeptide is set forth herein as LARSS<u>GVHWIAAWLVVTLSIIPSILLA</u> (SEQ ID NO:59), or a derivative thereof.

In some embodiments of the invention a fusion protein may comprise membrane-anchoring polypeptide domain that includes a Complement decay-accelerating factor polypeptide. A non-limiting example of a homo sapiens Complement decay-accelerating factor membrane-anchor polypeptide is set forth herein as SGTTS<u>GTTRLLSGHTCFTLTGLLGTLVTMGLLT</u> (SEQ ID NO:60), or a derivative thereof.

In some embodiments of the invention a fusion protein may comprise membrane-anchoring polypeptide domain that includes a lynx-1 polypeptide. A non-limiting example of a mus musculus lynx-1 membrane-anchor polypeptide is set forth herein as YLCNG<u>AGFATPVTLALVPALLATFWSLL</u> (SEQ ID NO:61), or a derivative thereof. As a non-limiting example, in some embodiments of the invention the amino acid sequence YLCNGAGFATPVTLALVPALLATFWSLL (SEQ ID NO:61), which is derived from lynx-1 was added to the c-terminus of the LOV2 domain (ending in DEAAKEL) for the fusion protein to be GPI anchored to a membrane.

In some embodiments of the invention, a GPI anchoring amino acid sequence such as those set forth as SEQ ID NO:57, SEQ ID NO:58, SEQ ID NO:59, SEQ ID NO:60, or SEQ ID NO:61, may be included at the c-terminus of the expressed fusion protein resulting in cleavage of the underlined residues and modification of the bold residue with the membrane anchor glycophosphatidylinositol. Other sequences for GPI anchoring are known in the art and may be used in fusion proteins and methods of the invention.

In some embodiments of the invention, a fusion protein of the invention includes a membrane-anchoring polypeptide domain that is a one-pass transmembrane polypeptide. Non-limiting examples of one-pass transmembrane polypeptides that may be used in fusion proteins and methods of the invention, include an amino acid sequence derived from an amino acid sequence of a platelet-derived-growth factor (PDGF) receptor polypeptide, a major histocompatibility Complex I polypeptide, a CD1b polypeptide, or a CD1c polypeptide.

Transmembrane domains such as one-pass transmembrane polypeptides disclosed herein can be added at the c terminus of the other domains in a fusion protein of the invention, which results in membrane localization of the fusion protein. In some embodiments of the invention a transmembrane domain may be used to express a Lighand at a cell location, examples of which include, but are not limited to the cell surface (for example on the external or internal surface of the plasma membrane), the nuclear membrane, a mitochondrial membrane, an organelle membrane, etc.). A transmembrane domain sequence that is used in fusion proteins and methods of the invention may further comprise a fluorescent protein marker. A protein marker, (also referred to herein as a reporter molecule), may be used for tracking the position and location of a fusion protein of the invention.

In some embodiments of the invention a fusion protein may comprise a trans-membrane-anchoring polypeptide domain that includes a Beta Platelet-derived-growth factor receptor polypeptide. A non-limiting example Homo sapiens Beta Platelet-derived-growth factor receptor transmembrane-anchor polypeptide, is set forth herein as RNAVGQDTQEVIVVPHSLPFKVVVISAILALVVLTIISLIILIMLWQKKPR (SEQ ID NO:62), or a derivative thereof. Another example of an artificial Beta Platelet-derived-growth factor receptor transmembrane-anchor polypeptide is set forth herein as RVAVGQDTQEVIVVPHSLPFKVVVI-SAILALVVLTIISLIILIMLWQKKPRRIR (SEQ ID NO:75).

In some embodiments of the invention a fusion protein may comprise a trans-membrane-anchoring polypeptide domain that includes a Major Histocompatibility Complex I polypeptide. A non-limiting example of a Rattus norvegicus Major Histocompatibility Complex I transmembrane-anchor polypeptide is set forth herein as QDPSTDSN-METTVIYVILGAVAMIGAVAIIGAMVAV-VRRRKRNTGGKGGDYAPA PGRDSSQSSDVSLPDCKA (SEQ ID NO:63), or a derivative thereof.

In some embodiments of the invention a fusion protein may comprise a trans-membrane-anchoring polypeptide domain that includes a CD1b polypeptide. A non-limiting example of a Homo sapiens CD1b transmembrane-anchor polypeptide is set forth herein as QDIILYWRNPTSIGSIVLAI-IVPSLLLLLCLALWYMRRRSYQNIP (SEQ ID NO:64), or a derivative thereof.

In some embodiments of the invention a fusion protein may comprise a trans-membrane-anchoring polypeptide domain that includes a CD1c polypeptide. A non-limiting example of a Homo sapiens CD1c transmembrane-anchor polypeptide is set forth herein as QDIILYWGHHFSMNWIALVVIV-PLVILIVLVLWFKKHCSYQDIL (SEQ ID NO:65), or a derivative thereof.

In some embodiments of the invention, a fusion protein of the invention includes a membrane-anchoring polypeptide domain that is a channel complex-anchoring polypeptide. A non-limiting example of a channel complex-anchoring polypeptide that may be used in fusion proteins and methods of the invention comprises an amino acid sequence derived from an amino acid sequence of a BKCA α polypeptide.

Inclusion of a channel complex-anchoring polypeptide in a fusion protein of the invention permits the fusion protein to be attached to the cognate channel or receptor of the ligand included in the fusion protein. Thus, in some embodiments of the invention, a fusion protein is anchored to the target channel or receptor. A non-limiting example of domains in such a fusion protein include: (1) Secretion Signal; (2) Iberiotoxin QFTDVDCSVSKECWSVCKDLFGVDRGKC-MGKKCRCYQ (SEQ ID NO:66); (3) a Linker for example, (GSG)$_n$ where n=1, 2, 3, 4, 5, 6, 7, 8, 9, or 10; (4) AsLOV2 sequence; and (5) a BKCA alpha sequence, (for example, derived from a KCMA1_HUMAN, Uniprot Q12791 polypeptide).

In some embodiments of the invention a fusion protein may comprise a channel complex-anchoring polypeptide domain that includes a BKCA alpha polypeptide. A non-limiting example of a Homo sapiens BKCA alpha polypeptide is set forth as KCMA1_HUMAN, Uniprot Q12791 sequence or a derivative thereof. A non-limiting example of an amino acid sequence of a BKCA alpha polypeptide is provided as SEQ ID NO:74. A BKCA polypeptide (a non-limiting example of which may be a fragment of SEQ ID NO:74) may be included in a Lighand of the invention.

In some embodiments of the invention, a Lighand of the invention includes a membrane-anchoring polypeptide domain that is a channel complex partner anchoring polypeptide. A non-limiting example of a channel complex partner anchoring polypeptide that may be used in fusion proteins and methods of the invention comprises an amino acid sequence derived from an amino acid sequence of a KChip1 polypeptide. A non-limiting example of an amino acid sequence of a KChip1 polypeptide is provided as SEQ ID NO:73. A KChip1 polypeptide (a non-limiting example of which may be a fragment of SEQ ID NO:73) can be selected for use in a Lighand of the invention.

Inclusion of a channel complex partner anchoring polypeptide in a fusion protein of the invention permits the fusion protein to be attached to an interaction partner of the cognate channel or receptor of the ligand included in the fusion protein. Thus, in some embodiments of the invention, a fusion protein is anchored to an interaction partner of the target channel or receptor. A non-limiting example of domains in such a fusion protein include (1) secretion signal; (2) a αDTX sequence (see sequence example provided elsewhere herein); (3) a linker, for example, (GSG)$_n$ where n=1, 2, 3, 4, 5, 6, 7, 8, 9, or 10; (GSG)n; (4) a AsLOV2 sequence; and (5) a KChip1 sequence (KCIP1_HUMAN, Uniprot Q9NZI2).

In some embodiments of the invention a fusion protein may comprise a channel complex-anchoring polypeptide domain that includes a KCIP1 polypeptide. A non-limiting example of a *Homo sapiens* KCIP1 polypeptide is set forth as a KCIP1_HUMAN, Uniprot Q9NZI2 sequence or a derivative thereof. A non-limiting example of an amino acid sequence of a KChip1 polypeptide is provided as SEQ ID NO:73. A KChip1 polypeptide (a non-limiting example of which may be a fragment of SEQ ID NO:73) can included in a Lighand of the invention.

It will be understood that membrane anchoring signal sequences disclosed herein are not intended to be limiting and that additional membrane anchoring polypeptides (and sequences thereof), etc. are well known in the art and may be included in a fusion protein of the invention [see for example U.S. Patent Application Publication No. US 2006/0057614; Ibanez-Tallon, I. et al., (2004) Neuron 43, 305-311; Holford, M. et al., (2009) Front Mol Neurosci 2, 21; Fortin, J. P. et al., (2009) Proc Natl Acad Sci USA 106, 8049-8054; Auer, S. et al., (2010) Nat Methods 7, 229-236; Stürzebecher, A. S. et al., (2010) J Physiol (Lond) 588, 1695-1707; Mercanti, V. et al., (2010) J Cell Sci 123, 3329-3335; and Glomset, J. A. et al., (1990) Trends Biochem Sci 15, 139-142]. Membrane anchoring sequences that may be used to attach or tether a fusion protein to a membrane or cell are known in the art and can be used to select and optimize use of membrane anchoring sequences in fusion protein and methods of the invention.

Reporter Molecule Polypeptides

In some embodiments, a Lighand of the invention may include a reporter molecule. In certain embodiments the reporter molecule is a reporter molecule polypeptide domain. Thus, a reporter molecule may be domain of an expressed Lighand or may be a molecule that is added to an expressed Lighand. In some embodiments of the invention, a reporter molecule polypeptide domain comprises a fluorescent reporter polypeptide. In some embodiments of the invention, a reporter molecule polypeptide domain compromises an enzymatic reporter polypeptide. Non-limiting examples of reporter molecules include mcherry, tdTomato, mPlum, Katushka, Neptune, green fluorescent protein (GFP), Yellow fluorescent protein (YFP) [see for example, Shaner, N. C. et al., (2005) Nat Methods 2, 905-909], miniSOG [see for example, Shu, X. et al., (2011) PLoS Biol 9, e1001041], KillerRed [see for example, Bulina, M. E. et al., (2006) Nat Biotechnol 24, 95-99], Luciferase [see for example, promega.com/resources/product-guides-and-selectors/protocols-and-applications-guide/bioluminescent-reporters/], β-lactamase [see for example, Qureshi, S. A., (2007) BioTechniques 42, 91], etc. Inclusion and use of reporter molecules with fusion proteins is well known in the art. Methods of including and/or encoding a reporter molecule, such as a reporter polypeptide in a Lighand of the invention, and methods of monitoring and imaging such a reporter molecule can be performed using routine methods known in the art.

Polynucleotides, Vectors, and Expression

Certain aspects of the invention include methods for preparing and using polynucleotides encoding Lighands the invention. The invention, in part, also includes polynucleotides that encode Lighands of the invention as well as vectors and constructs that comprise such polynucleotide sequences. Thus, in some embodiments of the invention, a vector may be prepared that comprises a polynucleotide sequence that encodes a Lighand's polypeptide domains. In some embodiments the invention includes expression of a Lighand encoded by the polynucleotide sequences, in cells, tissues, and organisms. Also included in some aspects of the invention are methods of combinatorial optimization of polynucleotides encoding Lighands through targeted polypeptide site-directed mutagenesis, potent protein trafficking sequences, wavelength-specific photoreceptor sequences, etc. The resultant polynucleotide products, when expressed in genetically targeted cells, allow the alternation of channel and receptor activity in response to one or more pulses of light. The Lighand fusion proteins of the invention may be genetically expressed in specific cells (e.g., using a virus or other vector) and then used to control cells in intact organisms (including humans) as well as in vitro and ex vivo cells in response to pulses of light.

Sequences

The present invention includes, in part, the expression and use of a novel class of fusion proteins, termed Lighands, to alter channel function in cells and membranes. In some embodiments of the invention one or more Lighands may be expressed in cells that are in culture, in a subject, or isolated cells. Lighands of the invention may include polypeptide domains comprising amino acid sequences derived from any organism. For example, a Lighand of the invention may include polypeptide domains derived from a human polypeptide, a rat polypeptide, a plant polypeptide, a mouse polypeptide, etc. It will be understood that each polypeptide domains in a single Lighand need not be derived from the same organism. As used herein with respect to amino acid and nucleic acid sequences, the term "derived from" includes a sequence that is the same as a sequence identified in an organism and also includes a sequence that has been modified from a sequence identified in an organism. For example, although not intended to be limiting is a derived photoreceptor polypeptide may include amino acid residues 404-546 of a phototropin I polypeptide from Avena sativa or may include amino acid residues 404-546 of the phototropin I polypeptide from Avena sativa, but with one or more amino acid deletions, additions, or substitutions.

Lighand polypeptide domain sequences having one or more substitutions or other modifications can be identified and tested for characteristics including, but not limited to: expression, cell localization, ligand access to cognate (also referred to as the ligand's "target") channel or receptor in dark and light conditions, channel block in response to light or dark conditions, etc. and silencing in response to contact with light using methods disclosed herein.

A Lighand domain polypeptide of the invention may include amino acid variants (e.g., polypeptides having a modified sequence) of the sequences as set forth herein. Modified Lighand domain sequences may have at least about 75%, 80%, 85%, 90%, 95%, 96%, 97%, 98%, 99%, or 100% identity with the polypeptide sequence of a Lighand domain sequence disclosed herein. Identity in this context means sequence similarity. Such sequence identity can be determined using standard techniques known in the art. Lighands of the present invention include the Lighand polypeptide and polynucleotide domain sequences provided herein and variants that have more than about 50%, 55%, 60%, 65%, 70%, 75%, 80%, 85%, 90%, 95%, 96%, 97%, 98%, or 99% identity to a provided domain sequence.

Lighand polypeptide domains of the invention may be shorter or longer than the Lighand polypeptide domain sequences set forth herein. Thus, a composition of the invention may include a Lighand polypeptide domain that is the same length as a Lighand polypeptide domain set forth herein, or may include a functional fragment thereof.

Sequence modifications can be in one or more of three classes: substitutions, insertions or deletions. These modified sequences, (which may also be referred to herein as variants or derivatives) ordinarily are prepared by site specific mutagenesis of nucleic acids in the DNA encoding a Lighand polypeptide domain, using cassette or PCR mutagenesis or other techniques known in the art, to produce DNA encoding the modified Lighand domain. Amino acid sequence variants are characterized by the predetermined nature of the variation, thus, a variant may be designed and selected based on knowledge of a Lighand domain sequence of the invention. Modified Lighand polypeptide domains may exhibit the same qualitative biological activity as the originating Lighand polypeptide domain from which they are derived or may be designed and selected to have one or more modified characteristics.

A site or region for introducing an amino acid sequence modification in a domain may be predetermined, and the mutation per se need not be predetermined. For example, to optimize the performance of a mutation at a given site, random mutagenesis may be conducted at the target codon or region and the expressed modified Lighand domain screened for the optimal combination of desired activity. Techniques for making substitution mutations at predetermined sites in DNA having a known sequence are well known, for example, M13 primer mutagenesis and PCR mutagenesis.

Amino acid substitutions may be made for 1, 2, 3, 4, 5, 6, 7, 8, 9, 10, 11, 12, 13, 14, 15, 16, 17, 18, 19, 20, or more residues in a domain; and insertions may made for 1, 2, 3, 4, 5, 6, 7, 8, 9, 10, 11, 12, 13, 14, 15, 16, 17, 18, 19, 20 or more amino acids in a domain. Deletions may range from about 1, 2, 3, 4, 5, 6, 7, 8, 9, 10, 11, 12, 13, 14, 15, 16, 17, 18, 19, 20 residues in a domain, although in some cases deletions may be larger.

Substitutions, deletions, insertions or any combination thereof may be used to arrive at a one or more modified domains in a Lighand of the invention. Generally these changes are done on a few amino acids to minimize the alteration of the molecule. However, larger changes may be tolerated in certain circumstances.

Variants of Lighand domains set forth herein, may exhibit the same qualitative light-modulated activity as one or more of the Lighand sequences set forth herein, but may show some altered characteristics such as altered stability, speed, reversibility, compatibility, or toxicity, or a combination thereof. For example, a Lighand polypeptide can be modified such that it has an increased effect of the function of an ion channel or receptor, or may be modified to have a decreased effect on the function of the ion channel or receptor as compared to an effect of another Lighand polypeptide on the ion channel or receptor.

A Lighand polypeptide of the invention can incorporate unnatural amino acids as well as natural amino acids. An unnatural amino acid can be included in a Lighand of the invention to enhance a characteristic such as altered photocurrent, stability, speed, reversibility, compatibility, or to lower toxicity, etc.

One skilled in the art will be able to identify additional polypeptide sequences that may be used in polypeptide domains of Lighands of the invention. For example, sequences with sufficient amino acid sequence homology to sequences provided herein, sequences modified from sequences provided herein, etc. A skilled artisan can also select one or more polypeptide sequences in addition to those disclosed herein that may be included in a Lighand. For example, an alternative ligand to one disclosed herein may be selected and included such that the resulting Lighand of the invention functions in a desired manner. Thus, in some embodiments of the invention, an artisan may select and include in a Lighand of the invention a photoreceptor polypeptide sequence, a ligand polypeptide sequence, a linker polypeptide sequence, a trafficking polypeptide sequence, a membrane-anchoring polypeptide sequence, and/or a reporter polypeptide sequence that differs from a sequence disclosed herein, but is suitable to function in a Lighand of the invention.

Another aspect of the invention provides polynucleotide sequences that code for a Lighand polypeptide of the invention. It would be understood by a person of skill in the art that the Lighand polypeptides of the present invention can be coded for by various nucleic acids. Each amino acid in the protein is represented by one or more sets of three nucleic acids (codons). Because many amino acids are represented by more than one codon, there is not a unique polynucleotide sequence that codes for a given protein. It is well understood by those of skill in the art how to make a polynucleotide that can code for a Lighand polypeptide of the invention by knowing the amino acid sequence of the protein. A polynucleotide sequence that codes for a polypeptide or protein is the "gene" of that polypeptide or protein. A gene can be RNA, DNA, or other nucleic acid than will code for the polypeptide or protein.

Delivery of Lighands

Delivery of a Lighand polypeptide to a cell and/or expression of a Lighand in a cell can be done using art-known delivery means [see for example: Kingston, R. E. et al., (2003) Current Protocols in Cell Biology, Unit 20, John Wiley & Sons, Inc., Hoboken, N.J., USA; Zeitelhofer, M. et al., (2009) Current Protocols in Neuroscience, Unit 4, John Wiley & Sons, Inc., Hoboken, N.J., USA,; Hawley-Nelson, P. et al., (2008) Current Protocols in Molecular Biology, Unit 9, John Wiley & Sons, Inc., Hoboken, N.J., USA; Mueller, C. et al., (2005) Current Protocols in Microbiology, John Wiley & Sons, Inc., Hoboken, N.J., USA; Southgate, T. et al., (2008) Current Protocols in Neuroscience, Unit 4.23, John Wiley & Sons, Inc., Hoboken, N.J., USA; and Ramezani, A. et al., (2002) Current Protocols in Molecular Biology, Unit 16, John Wiley & Sons, Inc., Hoboken, N.J., USA].

In some embodiments of the invention a Lighand polypeptide may be delivered to a cell in the form of a polynucleotide that encodes the fusion protein. It is well known in the art how to prepare encoding sequences for, express, and utilize fusion proteins that comprise polypeptide sequence domains [see for example: Snapp, E., (2005) Current Protocols in Cell Biology, Unit 21, John Wiley & Sons, Inc., Hoboken, N.J., USA; and Hollenbaugh, D. et al., (2002) Current Protocols in Immunology, Unit 10, John Wiley & Sons, Inc., Hoboken, N.J., USA]. Delivery of a Lighand-encoding polynucleotide molecule to a desired cell, tissue or region can be performed using art-known procedures. It is an aspect of the invention to provide a Lighand polypeptide of the invention that is non-toxic, or substantially non-toxic in cells in which it is expressed. In certain embodiments of the invention, in the absence of light, a Lighand of the invention may not significantly alter cell health or ongoing electrical activity in the cell in which it is expressed. In certain embodiments of the invention, in the absence of light, a Lighand of the invention does significantly alter cell health or ongoing electrical activity in the cell in which it is expressed.

In some embodiments of the invention, a Lighand polypeptide of the invention is genetically introduced into a cellular membrane, (for example via delivery of a polynucleotide that encodes the Lighand) and reagents and methods are provided for genetically targeted expression of Lighand polypeptides. Genetic targeting can be used to deliver Lighand polypeptides to specific cell types, to specific cell subtypes, to specific spatial regions within an organism, and to sub-cellular regions within a cell. Genetic targeting also relates to the control of the amount of Lighand polypeptide expressed, and the timing of the expression.

Some embodiments of the invention include a reagent for genetically targeted expression of a Lighand polypeptide, wherein the reagent comprises a vector that contains the gene for the Lighand polypeptide. As used herein, the term "vector" refers to a nucleic acid molecule capable of transporting between different genetic environments another nucleic acid (e.g., polynucleotide) to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert Lighand polypeptides into dividing and non-dividing cells and can insert Lighand polypeptides to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein.

In certain embodiments of the invention, a vector may be a lentivirus comprising the gene for a Lighand of the invention, or a variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a Lighand polypeptide in a wide variety of cell types—thus a promoter for a gene that is widely expressed in a variety of cell types, for example a "housekeeping gene" can be used to express a Lighand polypeptide in a variety of cell types. Non-limiting examples of general promoters are provided elsewhere herein and suitable alternative promoters are well known in the art.

In certain embodiments of the invention, a promoter may be an inducible promoter, examples of which include, but are not limited to tetracycline-on or tetracycline-off, or tamoxifen-inducible Cre-ER, etc. [see for example: Neve, R. L. & Neve, K. A., (2001) Overview of Neural Gene Expression, Current Protocols in Neuroscience, Unit 4, John Wiley & Sons, Inc., Hoboken, N.J., USA; Riggs, P. et al., (2001) Introduction to Expression by Fusion Protein Vectors, Current Protocols in Molecular Biology, Unit 16, John Wiley & Sons, Inc., Hoboken, N.J., USA; Qin, J. Y. et al., (2010) PLoS ONE 5(5): e10611].

Methods of Use of Lighands of the Invention

In some aspects of the invention, methods of preparing a Lighand of the invention are provided. Such methods, which are also referred to herein as methods of manufacturing, may include delivering to a cell a polynucleotide molecule that encodes a fusion protein comprising a polypeptide ligand domain, a linker polypeptide domain, and a photoreceptor polypeptide domain; and expressing in the cell the fusion protein encoded by the polynucleotide, wherein the expressed fusion protein, a Lighand, comprises a synthetic, light-modulated protein. In some embodiments, methods of preparing a Lighand include expressing in a cell a polynucleotide molecule that, in addition to encoding a ligand domain, a photoreceptor domain, and a linker domain, also encodes a membrane-anchoring polypeptide domain. A membrane-anchoring polypeptide domain may be a domain that anchors the Lighand to a plasma membrane, either on the internal surface in some embodiments of the invention, or on the external surface in certain embodiments of the invention. In some embodiments, methods of preparing a Lighand include expressing in a cell a polynucleotide molecule that, in addition to encoding a ligand domain, a photoreceptor domain, and a linker domain, and optionally a membrane-anchoring polypeptide domain, also encodes a trafficking signal polypeptide domain. A trafficking signal may, as described elsewhere herein, be a signal that directs or positions an encoded polypeptide to a specific location or placement inside or outside the cell in which it was expressed. In some embodiments of the invention, methods of making a Lighand include methods of making a Lighand that comprises a ligand domain, a photoreceptor domain, and a linker domain, and that also includes membrane-anchoring polypeptide domain and a secretion signal polypeptide domain.

Methods of making a Lighand of the invention may also comprise expressing the Lighand in an isolated cell, a cell in culture, a cell in a subject, a cell in solution, etc. A cell may be an in vivo cell, an in vitro cell, or an ex-vivo cell. Non-limiting examples of cell types in which a Lighand of the invention can be prepared are neuronal cells, cardiac cells, lymphocytes, leukocytes, glial cells, neuroglial cells, macroglial cells, astrocytes, oligodendrocytes, Schwann cells, and microglial cells. A cell in which a Lighand of the invention is expressed, may in some embodiments be an immortal cell or a tumor cell.

In some embodiments of the invention, the polynucleotide molecule that encodes the fusion protein may be delivered to the cell in which it is to be expressed by means of pharmaceutical composition comprising the polynucleotide molecule. Thus, a pharmaceutical composition that includes the polynucleotide can be prepared and delivered to a cell and the Lighand expressed in the cell.

In some embodiments, the invention also includes methods of modulating a functional state of an ion channel in a cell membrane. The methods may include delivering to a cell that includes a cell membrane ion channel, a polynucleotide molecule that encodes a fusion protein comprising a polypeptide ligand domain, a linker polypeptide domain, and a photoreceptor polypeptide domain, wherein the ligand is a ligand for the ion channel; expressing in the cell the fusion protein encoded by the polynucleotide, wherein the resulting polypeptide comprises a light-modulated synthetic polypeptide; and contacting the expressed light-modulated synthetic polypeptide with an effective dose of a light to modulate a conformation of the fusion protein, wherein the modulation of the conformation of the fusion protein alters a functional state of the ion channel in the membrane.

In some embodiments of the method, the cell is in vitro, and in certain embodiments the cell is in a subject. In some embodiments, the subject may have been diagnosed with, or expected to have, neurological, immune system, or cardiac disease or condition.

In some embodiments, the invention also includes methods of determining the effect of a candidate therapeutic compound on a functional state of an ion channel of a membrane. As used herein the term "determining" in the context of the method may include measuring or assessing whether or not there is an effect. The methods of determining the effect of a candidate therapeutic compound may include delivering to a cell comprising a cell membrane ion channel, a polynucleotide molecule that encodes a fusion protein comprising a polypeptide ligand domain, a linker polypeptide domain, and a photoreceptor polypeptide domain, wherein the polypeptide ligand is a ligand for the ion channel; expressing in the cell the fusion protein encoded by the polynucleotide; contacting the cell with a candidate therapeutic compound; contacting the expressed fusion protein with a dose of a light effective to modulate a conformation of the fusion protein; determining the functional state of the ion channel; and comparing the determined functional state of the ion channel with a control functional state of the ion channel, wherein a difference between the determined functional state and the control functional state indicates an effect of the candidate therapeutic compound on the functional state of the ion channel.

Methods of illuminating Lighands of the invention for modulating channel activity and/or for testing of channel modulation activity of Lighands of the invention may include methods known in the art for optical triggering and activation. Examples of methods of illumination and measurement of ion conductance that may be used in methods of the invention are described references such as Boyden, E. S., et al., (2005). Nat Neurosci 8, 1263-1268; Chow, B. Y., et al. (2010). Nature 463, 98-102; and Han, X., and Boyden, E. S. (2007). PLoS ONE 2, e299.

Cells and Subjects

A cell used in methods and with sequences of the invention may be an excitable cell or a non-excitable cell. A cell in which a Lighand of the invention may be expressed and may be used in methods of the invention may be a prokaryotic or a eukaryotic cell. Useful cells include but are not limited to mammalian cells. Examples of cells in which a Lighand of the invention may be expressed are excitable cells, which include cells able to produce and respond to electrical signals. Lighands of the invention may also be expressed in non-excitable cells and may function therein, for example, when activated by suitable light to alter the function of ion channels or receptors located in internal membranes of the non-excitable cells. For example, a Lighand of the invention may alter ion passage through a channel located on a mitochondrial membrane of an excitable or a non-excitable cell in which it is expressed. Lighands and methods of the invention may include use of excitable or non-excitable cells in methods of candidate compound assessment, diagnosis, and treatment. Examples of non-excitable cells to which Lighands of the invention and methods using Lighands of the invention include, but are not limited to cells of the lung, pancreas, liver, muscle, intestine, skin, etc.

Examples of cell types that may be used in methods of the invention include, but are not limited to neuronal cells, muscle cells, cardiac cells, secretory cells (such as pancreatic cells, adrenal medulla cells, pituitary cells, etc.), lymphocytes, leukocytes; glial cells, neuroglial cells, macroglial cells, astrocyte cells, oligodendrocyte cells, Schwann cells, and microglial cells. In some embodiments of the invention, a cell may be an immortal cell or may be a tumor cell.

In some embodiments, a cell used in conjunction with the invention may be a healthy normal cell, which is not known to have a disease, disorder or abnormal condition. In some embodiments, a cell used in conjunction with methods and Lighands of the invention may be an abnormal cell, for example, a cell that has been diagnosed as having a disorder, disease, or condition, including, but not limited to a neurological disease or condition, a cardiac disease or condition, including but not limited to: epilepsy, drug-resistant depression, schizophrenia, tachycardia, bradycardia, atrial fibrillation, LongQT syndrome, glioblastoma, medullablastoma, neuroblastoma, leukemia, or lymphoma, an injured cell, etc. In some embodiments of the invention, a cell may be a control cell. Additional diseases and conditions that may be characterized by abnormal ion conductance across channels or receptors (e.g., higher or lower levels of ion conductance as compared to a level of ion conductance in a control not having the disease or condition) are known in the art and may also be treated using methods of the invention, and candidate therapeutic compounds to treat such diseases and/or conditions may also be tested using methods and Lighands of the invention.

Lighands of the invention may be expressed in cells from culture, cells in solution, cells obtained from subjects, and/or cells in a subject (in vivo cells), ex-vivo cells, in-vitro cells, etc. Lighands may be expressed and activated in cultured cells, cultured tissues (e.g., brain slice preparations, etc.), and in living subjects, etc. As used herein, a the term "subject" may refer to a human, non-human primate, cow, horse, pig, sheep, goat, dog, cat, rodent, bird, reptile, insect, fish, fly or any other vertebrate or invertebrate organism.

Controls and Candidate Compound Testing

Lighands of the invention and methods using Lighands of the invention can be utilized to assess changes in cells, tissues, and subjects in which they are expressed. Some embodiments of the invention include use of Lighands of the invention to identify effects of candidate compounds on cells, tissues, and subjects. Results of testing a Lighands of the invention can be advantageously compared to a control.

As used herein a control may be a predetermined value, which can take a variety of forms. It can be a single cut-off value, such as a median or mean. It can be established based upon comparative groups, such as cells or tissues that include the Lighand and are contacted with light, but are not contacted with the candidate compound and the same type of cells or tissues that under the same testing condition are contacted with the candidate compound. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

As a non-limiting example of use of a Lighand to identify a candidate therapeutic agent or compound, a Lighand of the invention may be expressed in an excitable cell in culture or in a subject and the excitable cell may be contacted with a light that modulates the Lighand and with a candidate therapeutic compound. In one embodiment, a test cell that includes a Lighand of the invention can be contacted with a light that modulates the photoreceptor polypeptide of the Lighand thereby reducing conductance of a channel in the cell, and the test cell is also contacted with a candidate compound. The cell, tissue, and/or subject that include the cell can be monitored for the presence or absence of a change that occurs in the test conditions versus the control conditions. For example, in a cell, a change may be a change in the conductance of the channel in the test cell versus a control cell, and a change in the conductance of the channel in the test cell compared to the control may indicate that the candidate compound has an effect on the test cell or tissue that includes the cell.

Candidate-compound identification methods of the invention that are performed in a subject, may include expressing a Lighand in the subject, contacting the subject with a light under suitable conditions to activate the Lighand and hyperpolarize the cell, and administering to the subject a candidate compound. The subject is then monitored to determine whether any change occurs that differs from a control effect in a subject. Thus, for example, function of channels in a brain region may be altered (increased or decreased) using a Lighand of the invention and a candidate compound may be administered to the brain and the effect of the compound determined by comparing the results with those of a control.

Methods of identifying effects of candidate therapeutic compounds using Lighands of the invention may also include additional steps and assays to further characterizing an identified change in the cell, tissue, or subject when the cell is contacted with the candidate compound. In some embodiments, testing in a cell, tissue, or subject can also include one or more cells that has a Lighand of the invention that is contacted with a dose of light effective to modulate the conformation of the photoreceptor in the Lighand and alter the ion conductivity of a channel or receptor. In some embodiments of the invention, test methods using a Lighand enable new kinds of drug screening using light to alter ion conductance of a channel or receptor, contacting the channel or receptor (or the cell) with a candidate therapeutic compound and determining the presence or absence and amount of an effect of the compound on the ion channel conductance.

In some embodiments, Lighand polypeptides of the invention can be used in test systems and assays for assessing effects of candidate therapeutic agents, effect of expression of modified channels or receptors, etc. Lighands of the invention can be used test compounds to treat diseases or conditions such as a neurological disease or condition, a cardiac disease or condition, including but not limited to: epilepsy, drug-resistant depression, schizophrenia, tachycardia, bradycardia, atrial fibrillation, LongQT syndrome, glioblastoma, medullablastoma, neuroblastoma, leukemia, or lymphoma, an injured cell, etc.

Methods of Treating

Some aspects of the invention include methods of treating a disorder or condition in a cell, tissue, or subject using one or more Lighands of the invention. Treatment methods of the invention may include administering to a subject in need of such treatment, a therapeutically effective amount of a Lighand of the invention to treat the disorder. It will be understood that a treatment may be a prophylactic treatment or may be a treatment administered following the diagnosis of a disease or condition. A treatment of the invention may reduce or eliminate a symptom or characteristic of a disorder, disease, or condition or may eliminate the disorder, disease, or condition itself. It will be understood that a treatment of the invention may reduce or eliminate progression of a disease, disorder or condition and may in some instances result in the regression of the disease, disorder, or condition. A treatment need to entirely eliminate the disease, disorder, or condition to be effective.

Administration of a Lighand of the invention may include administration pharmaceutical composition that includes a cell, wherein the cell expresses the Lighand. Administration of a Lighand of the invention may include administration of a pharmaceutical composition that includes a vector, wherein the vector comprises a polynucleotide sequence encoding the Lighand and the administration of the vector results in expression of the Lighand in one or more cells in the subject.

An effective amount of a Lighand is an amount that increases the level of the Lighand in a cell, tissue or subject to a level that is beneficial for the subject. An effective amount may also be determined by assessing physiological effects of administration on a cell or subject, such as a decrease in symptoms following administration. Other assays will be known to one of ordinary skill in the art and can be employed for measuring the level of the response to a treatment. The amount of a treatment may be varied for example by increasing or decreasing the amount of the Lighand administered, by changing the therapeutic composition in which the Lighand is administered, by changing the route of administration, by changing the dosage timing and so on. The effective amount will vary with the particular condition being treated, the age and physical condition of the subject being treated; the severity of the condition, the duration of the treatment, the nature of the concurrent therapy (if any), the specific route of administration, and the like factors within the knowledge and expertise of the health practitioner. For example, an effective amount may depend upon the location and number of cells in the subject in which the Lighand is to be expressed. An effective amount may also depend on the location of the tissue to be treated.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of a composition to increase the level of a Lighand (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

A Lighand of the invention may be administered using art-known methods. The manner and dosage administered may be adjusted by the individual physician or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compositions that deliver Lighands of the invention may be administered alone, in combination with each other, and/or in combination with other drug therapies, or other treatment regimens that are administered to subjects. A pharmaceutical composition used in the foregoing methods preferably contain an effective amount of a therapeutic compound that will increase the level of a Lighand polypeptide to a level that produces the desired response in a unit of weight or volume suitable for administration to a subject.

The dose of a pharmaceutical composition that is administered to a subject to increase the level of Lighand in cells of the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The amount and timing of activation of a Lighand of the invention (e.g., light wavelength, length of light contact, etc.) that has been administered to a subject can also be adjusted based on efficacy of the treatment in a particular subject. Parameters for illumination and activation of Lighands that have been administered to a subject can be determined using art-known methods and without requiring undue experimentation.

Various modes of administration will be known to one of ordinary skill in the art that can be used to effectively deliver a pharmaceutical composition to increase the level of Lighand in a desired cell, tissue or body region of a subject. Methods for administering such a composition or other pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., Remington's Pharmaceutical Sciences, 18th edition, 1990) provide modes of administration and formulations for delivery of various pharmaceutical preparations and formulations in pharmaceutical carriers. Other protocols which are useful for the administration of a therapeutic compound of the invention will be known to one of ordinary skill in the art, in which the dose amount, schedule of administration, sites of administration, mode of administration (e.g., intra-organ) and the like vary from those presented herein.

Administration of a cell or vector to increase a Lighand level in a mammal other than a human; and administration and use of Lighands of the invention, e.g. for testing purposes or veterinary therapeutic purposes, may be carried out under substantially the same conditions as described above. It will be understood by one of ordinary skill in the art that this invention is applicable to both human and animals. Thus this invention is intended to be used in husbandry and veterinary medicine as well as in human therapeutics.

In some aspects of the invention, methods of treatment using a Lighand of the invention are applied to cells including but not limited to a nervous system cell, a neuron, a cardiovascular system cell, a circulatory system cell, a visual system cell, an auditory system cell, a muscle cell, an endocrine cell, a secretor cell (such as pancreatic cells, adrenal medulla cells, pituitary cells, etc.), an immune system cells, (e.g., lymphocytes, leukocytes, etc.). Examples of nervous system cells to which a treatment of the invention can be applied include, but are not limited to: glial cells, neuroglial cells, macroglial cells, astrocyte cells, oligodendrocyte cells, Schwann cells, and microglial cells.

Disorders and conditions that may be treated using methods of the invention include, injury, brain damage, degenerative neurological conditions, cardiovascular conditions, and may include treatment of diseases and conditions such as neurological or cardiac disease including, but not limited to Epilepsy, drug-resistant depression, schizophrenia, tachycardia, bradycardia, atrial fibrillation, LongQT syndrome, glioblastoma, medullablastoma, neuroblastoma, leukemia, lymphoma, etc. Methods of treatment that utilize light activated pumps and channels are known in the art. [See, for example, Busskamp, V. et al., (2010) Science July 23; 329(5990):413-7].

The present invention in some aspects, includes preparing nucleic acid sequences and polynucleotide sequences; expressing in cells Lighand polypeptides encoded by the prepared nucleic acid and polynucleotide sequences; illuminating the cells with suitable light, and determining the presence, absence, and/or level of alteration of ion conductance in a channel or receptor that is in the environment of the Lighand, in response to light or dark. The ability to alter ion channel conductance using Lighands of the invention has been demonstrated. The present invention enables light-control of cellular functions in vivo, ex vivo, and in vitro, and the Lighands of the invention and their use, have broad-ranging applications for drug screening, treatments, and research applications, some of which are describe herein.

EXAMPLES

Example 1

Introduction

Light-modulated fusion proteins were designed to include (1) genetically encoded, peptide ligands (e.g., toxins, etc.), some of which were membrane-tethered that bind with high specificity to ion channels and altered their functional properties and (2) photoreceptors that couple the absorption of photons to a conformational change [for photoreceptor information, see for example, Harper, S. M., (2003) Science 301, 1541-1544; and Yao, X. et al., (2008) Nat Chem Biol 4, 491-497]. In the resulting fusion protein, the photoreceptor's light-dependent conformation change was used to modulate the activity of the peptide toxin. The resulting molecular reagents that were produced are light-modulating fusion proteins, which are also referred to herein as "Lighands".

Figure 1:
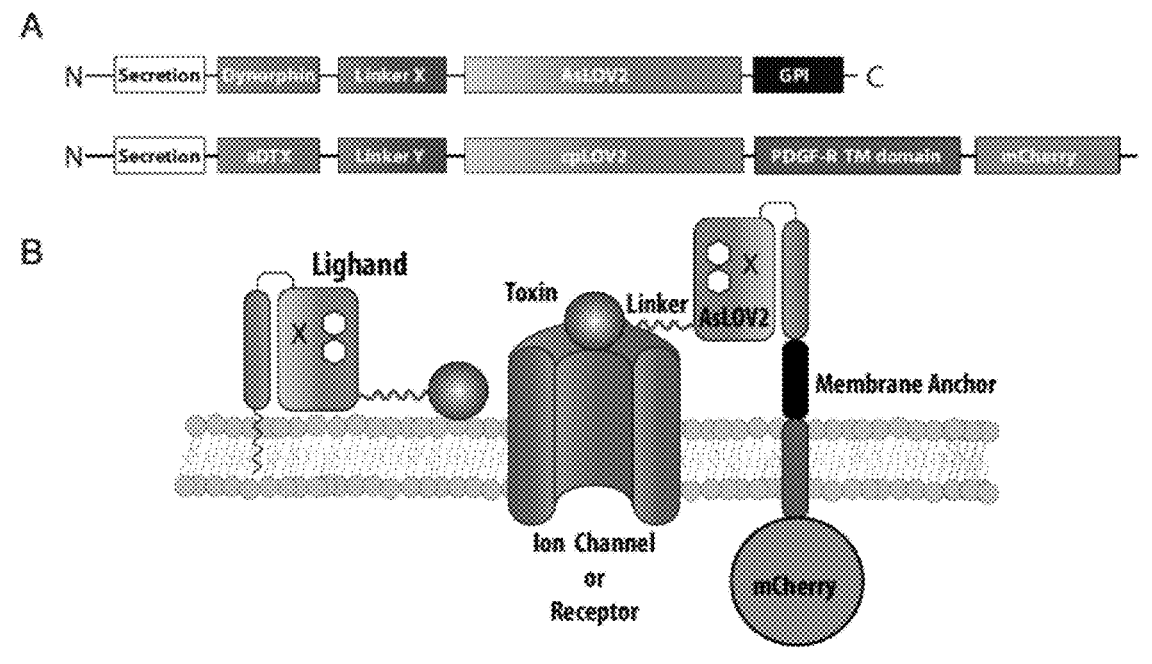

Materials and Methods
(Additional Materials are Also Disclosed in Procedures Sections Below)
Molecular Biology/Construct Generation Genes encoding for the fusion protein, termed Lighands, were assembled as a multicomponent cloning cassette from annealed oligonucleotides (IDT DNA) containing these elements (in order, see FIG. 1A): BglII or NheI or BamHI-Secretion Signal/FLAG tag-HindIII-αDTX-KpnI-Linker-LOV2(404-546)-NotI-PDGFR-mCherry-XbaI or EcoRI.

```
Secretion Signal/FLAG tag amino acid sequence
[MSALL ILALV GAAVA DYKDD DDKL (SEQ ID NO: 56)];

DNA sequence
[atg agc gcc ctg ctg atc ctg gcc ctg gtg ggc gcc gcc gtg gcc gac tac aag gac gac gac gac aag ctg (SEQ ID NO: 67)];
```

-continued

αDTX amino acid sequence
[QPRRK LCILH RNPGR CYDKI PAFYY NQKKK

QCERF DWSGC GGNSN RFKTI EECRR TCIG (SEQ ID NO: 1)];

DNA sequence
[cag ccc aga aga aag ctg tgc atc ctg cac aga aac ccc ggc aga tgc tac gac aag atc ccc gcc ttc tac tac aac cag aag aag aag cag tgc gag aga ttc gac tgg agc ggc tgc ggc ggc aac agc aac aga ttc aag acc atc gag gag tgc aga aga acc tgc atc ggc (SEQ ID NO: 68)];

Linker, amino acid sequence
[AAADY KDDDD KIDAA AGGAL CN (SEQ ID NO: 32)],;

DNA sequence
[gcc gcc gcc gac tac aag gac gac gac gac aag atc gac gcc gcc gcc ggc ggc gcc ctg tgc aac (SEQ ID NO: 69)];

AsLOV2, amino acid
[LATTL ERIEK NFVIT DPRLP DNPII FASDS FLQLT EYSRE

EILGR NCRFL QGPET DRATV RKIRD AIDNQ TEVTV QLINY TKSGK KFWNL

FHLQP MRDQK GDVQY FIGVQ LDGTE HVRDA AEREG VMLIK KTAEN IDEA

AKEL (SEQ ID NO: 50)];

DNA sequence
[ttg gct act aca ctt gaa cgt att gag aag aac ttt gtc att act gac cca aga ttg cca gat aat ccc att ata ttc gcg tcc gat agt ttc ttg cag ttg aca gaa tat agc cgt gaa gaa att ttg gga aga aac tgc agg ttt cta caa ggt cct gaa act gat cgc gcg aca gtg aga aaa att aga gat gcc ata gat aac caa aca gag gtc act gtt cag ctg att aat tat aca aag agt ggt aaa aag ttc tgg aac ctc ttt cac ttg cag cct atg cga gat cag aag gga gat gtc cag tac ttt att ggg gtt cag ttg gat gga act gag cat gtc cga gat gct gcc gag aga gag gga gtc atg ctg att aag aaa act gca gaa aat att gat gag gcg gca aaa gaa ctt (SEQ ID NO: 70)];

PDGFR-mcherry, amino acid sequence
[RVAVG QDTQE VIVVP HSLPF KVVVI

SAILA LVVLT IISLI ILIML WQKKP RRIRM VSKGE EDNMA IIKEF MRFKV

HMEGS VNGHE FEIEG EGEGR PYEGT QTAKL KVTKG GPLPF AWDIL SPQFM

YGSKA YVKHP ADIPD YLKLS FPEGF KWERV MNFED GGVVT VTQDS SLQDG

EFIYK VKLRG TNFPS DGPVM QKKTM GWEAS SERMY PEDGA LKGEIK

QRLKL KDGGH YDAEV KTTYK AKKPV QLPGA YNVNI KLDIT SHNED YTIVE

QYERA EGRHS TGGMD ELYK* (SEQ ID NO: 71)];

DNA sequence
[cga gtt gct gtg ggc cag gac acg cag gag gtc atc gtg gtg cca cac tcc ttg ccc ttt aag gtg gtg gtg atc tca gcc atc ctg gcc ctg gtg gtg ctc acc atc atc tcc ctt atc atc ctc atc atg ctt tgg cag aag aaa cca cgt agg att cgt atg gtg agc aag ggc gag gag gat aac atg gcc atc atc aag gag ttc atg cgc ttc aag gtg cac atg gag ggc tcc gtg aac ggc cac gag ttc gag atc gag ggc gag ggc gag ggc cgc ccc tac gag ggc acc cag acc gcc aag ctg aag gtg acc aag ggt ggc ccc ctg ccc ttc gcc tgg gac atc ctg tcc cct cag ttc atg tac ggc tcc aag gcc tac gtg aag cac ccc gcc gac atc ccc gac tac ttg aag ctg tcc ttc ccc gag ggc ttc aag tgg gag cgc gtg atg aac ttc gag gac ggc ggc gtg gtg acc gtg acc cag gac tcc tcc ctg cag gac ggc gag ttc atc tac aag gtg aag ctg cgc ggc acc aac ttc ccc tcc gac ggc ccc gta atg cag aag aag acc atg ggc tgg gag gcc tcc tcc gag cgg atg tac ccc gag gac ggc gcc ctg aag ggc gag atc aag cag agg ctg aag -continued
```
ctg aag gac ggc ggc cac tac gac gct gag gtc aag acc acc tac aag gcc aag aag ccc gtg cag ctg ccc ggc gcc tac aac gtc aac atc aag ttg gac atc acc tcc cac aac gag gac tac acc atc gtg gaa cag tac gaa cgc gcc gag ggc cgc cac tcc acc ggc ggc atg gac gag ctg tac aag taa (SEQ ID NO: 72)]
(derived from pFU-MrVIA-PC, Addgene [Stürzebecher, A.S. et al., (2010).
J Physiol (Lond) 588, 1695-1707].
```

This cassette was inserted into the mammalian expression vector pcDNA3.1 (Invitrogen) using NheI/Xba restriction sites or a lentiviral vector containing the CAMKII promoter [Han, X. et al., (2009) Neuron 62, 191-198] using BamHI/EcoRI sites. The gene coding for rat Kv1.2 (rKv1.2) was amplified from Kv1.2-pBluescript and inserted into pcDNA3.1 using BamHI/EcoRI. Both Lighand and channel cassette were also inserted into the bidirectional expression vector pBI-CMV1 using BglII/XbaI and BamHI/NotI sites respectively, to drive expression from the same plasmid. All construct were sequence verified.

Cell Culture PC12

PC12 cells were maintained in DMEM (Cellgro), 10% fetal bovine serume (Invitrogen), 5% Donor Horse Serum (Invitrogen), 1% Penicillin/streptomycin (Cellgro) and 1% sodium pyruvate (Biowhittaker). For electrophysiological recordings and imaging cells were plated in glass coverslip treated with Matrigel (BD Bioscience). Adherent cells were transfected using Lipofectamime LTX (Invitrogen) following manufacturer's instructions, with either equimolar amount of Lighand-pcDNA3.1 and rKV 1.2-pcDNA3.1 or rKv1.2-Lighand-pBI-CMV and recorded 36-48 hours later. For confocal microscopy, cell were fixed with 4% formaldehyde, permeabilized with 0.4% saponin and stained with anti-FLAG M2 peptide antibody (Sigma) followed by anti-mouse-Alexa488 secondary antibody staining (Invitrogen).

Cell Culture Neuron

All procedures involving animals were in accordance with the National Institute of Health Guide for the care and use of laboratory animals and approved by the Massachusetts Institute of Technology Animal Care and Use Committee. Hippocampal regions from C57 mice postnatal day 0-1 were isolated and digested with papain (100 units in Hank's balanced salt solution supplemented with 35 mM glucose, 1 mM Kynurenic acid, 0.3 mg/ml L-Cysteine and 10 mM $MgCl_2$) for 6-8 minutes. The reaction was stopped by washing and addition of 10 mg/ml bovine serum albumin and 10 mg/ml ovomucoid inhibitor. The tissue was then mechanically dissociated by titruating through P1000 plastic pipette tips and settled by gravitation. Dissociated neurons in the supernatant were plated on Matrigel-coated glass coverslip (BD Bioscience) and maintained in plating medium (MEM, 10% fetal bovine serum, 0.5% glucose, 10 mM HEPES, 2 mM L-glutamine, 0.5 mg/ml holo-transferrin, 25 ug/ml insulin, B27 supplement, buffered to pH 7.4 with NaOH. Neurons were transfected at 5 days in vitro using calcium-phosphate (Invitrogen) and recorded from 9-14 days in vitro.

Electrophysiology and Illumination $K^+$ current were recorded from PC12 cells 36-48 posttransfection using whole cell voltage clamp. Hippocampal neurons 9-14 days in vitro were characterized using whole cell current clamp. Analog signal were filtered (1-5 kHz) using the built-in 4-pole Bessel filter of an Axopatch 200B patch clamp amplifier (Molecular Devices), digitized at 10 kHz (Digidata 1440A, Molecular Devices) and stored on a computer hard disk. The bath solution contained (mM): 125 NaCl, 2 KCl, 3 $CaCl_2$, 1 $MgCl_2$, 10 HEPES, 30 glucose, adjusted to pH 7.3 with NaOH. For recordings from hippocampal neurons the bath solution was supplemented with (mM): 0.01 NQBX, 0.01 gabazine, 0.01 AP-5. The pipette solution contained (mM): 125 K-Gluconate, 8 NaCl, 0.1 $CaCl_2$, 0.6 $MgCl_2$, 1 EGTA, 10 HEPES, 4 Mg-ATP, 0.4 Na-GTP, adjusted to pH 7.3 with KOH. Osmolarity was adjusted to 295-300 mOsm with sucrose. Electrodes were drawn from borosilicate patch glass (Warner Instruments) to a resistance of 5-10 MOhm. Patches with access resistance of >50 MOhm were discarded from the data analysis. Cells were screened for mCherry expression using a 565 nm high-power LED (Thorlabs) filtered by a 560±40 nm bandpass filter (Semrock) through a 40× lens. Lighands were stimulated with a 455 nm high-power LED (Thorlabs).

Procedures and Results

First-Generation Lighands

A first generation of Lighands was designed to include different lengths linkers (8, 21, 37 residues, $(GSG)_n$, and $(AAADYKDDDDKIDAAAGGALCN)_n$ type (SEQ ID NO:31) that connected a LOV2 domain derived from residues 404-546 of Avena sativa phototropin I and the peptide toxin and anchored these to the membrane using a glycophosphatidylinositol (GPI) anchor processing of a c-terminal signal sequence (FIG. 1B). The peptide toxins that were used were against voltage-dependent $K^+$ (Kv) and $Na^+$ (Nav) channels (for example, Agitoxin2, αDTX, MrVIa, ATXII, KIIIA). DNA encoding for the resulting fusion proteins was packaged into a lentiviral expression vector, driving protein expression from the CAMKII promotoer (see for example, Han et al., 2009).

The resulting set of molecular reagents was characterized in cultured primary neurons and their use in nervous tissue was validated. Ion channels of the Kv1 family colocalize with Nav channels in the axonal initial segment and juxtaparanodes, and control the neuron's somatoaxonal excitability and fidelity of action potentials generated by Nav channels. Of all the peptide modulators tested, αDTX with the 21 & 37 residue linkers had a light-dependent effect on neuronal signalling. Previous experiments had shown that the peptide toxin αDTX increases excitability [Halliwell, J. V. et al., (1986) Proc Natl Acad Sci; and Bekkers, J. M. and Delaney, A. J., (2001) J Neurosci 21, 6553-6560].

The results of the study showed that the prepared genetically encoded, virally delivered light-activated Kv1 channel blocker (tethered αDTX Lighand) was also able to modulate the excitability of cultured mouse hippocampal neurons. As shown in FIG. 2, before illumination of the channel and expressed fusion protein, somatic current injection elicited one action potential (FIG. 2A). The same current injection lead to regenerative firing after illumination with 455 nm blue light (FIG. 2B,C). The firing threshold was shifted to more negative voltages after illumination (FIG. 2E, left panel) in neurons expressing the tethered toxins but not control neurons (FIG. 2E, right panel), consistent with blockade of sub-threshold Kv1 channels. Taken together, this first generation of Lighand suggested that light-dependent modulation of membrane-tethered ion channel toxins had been achieved.

Second-Generation Lighands

Figure 3:
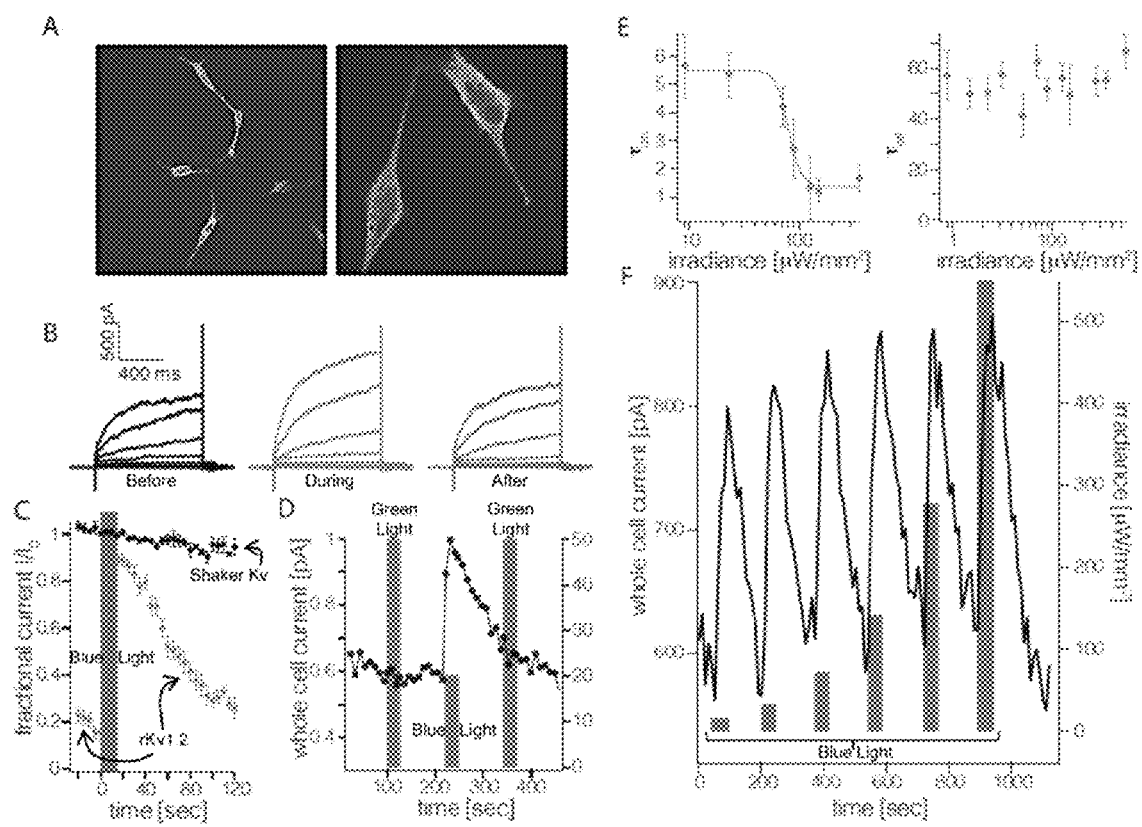
FIG. 3 shows photomicrographs, graphs and recording traces illustrating that Lighands modulate whole cell K+ currents in PC12 cells.

In results obtained testing of the first generation of Lighands the light-induced Kv1 channel block did not appear to be reversible. In addition, the lack of fluorescent expression markers made the electrophysiological characterization tedious and time-intensive as cells had to be patched blindly and randomly. In addition, due to the challenging nature of preparing good cultured primary neurons and glia, they are non-ideal reductionist expression systems and expression in HEK cell was poor for many constructs tested. To address these issues, Lighands were produced in which the GPI membrane anchor was replaced with a one-pass transmembrane domain taken from the beta platelet-derived growth factor receptor (PDGF-R). This transmembrane domain carries the fluorescent protein mCherry on the intracellular side and facilitates monitoring of expression. Several cell replicating lines (CH0, U2-OS, and PC-12) were also tested for their suitability as test beds for larger sets of Lighands. PC-12 cells were identified as a promising cell line; they expressed the Lighands to the membrane with reduced intracellular aggregation (FIG. 3A). PC-12 cells were a good alternative to studies in primary neuron culture, because they can be differentiated into a neuronal phenotype by the addition of nerve growth factor to the culture media [Gunning, P. W. et al., (1981) J Neurosci 1, 368-379].

Expressing tethered αDTX together with the Kv1.2 channel in cultured PC-12 cells allowed for detailed characterization and overcame several issues that had been observed in testing of earlier Lighand versions.

It was noted that by switching from the GPI anchor to the PDGF-R anchor the tethered αDTX Lighand was converted from a light-dependent channel blocker into a light-dependent channel activator. After illumination with 455 nm light, the amount of whole-cell current carried by K+ was increased by 60% (FIG. 3B). The PDGF-R domain contained a structured stretch of 26 extracellular amino acids, and thus likely extended the linker connection to the LOV2 in a way that allowed for the peptide toxin to bind the channel in the dark state. Illumination unfolded the LOV2 domain and increased the tether length further, thus lowering the local concentration and decreasing toxin block of Kv1.2. Altering linker length and membrane anchor was identified as a strategy for optimizing use of the Lighands and for selecting positive and negative regulators of channel and receptor function.

Examination of the activation and deactivation kinetics showed that the modulation of potassium ion ($K^+$) current was compatible with a model that assumed a channel-bound peptide toxin in the dark state, both in qualitative and quantitative terms. Unlike the GPI-anchored αDTX reversibility of the activated current was observed (FIG. 3B,F), allowing for the dynamic regulation of whole cell $K^+$ conductance.

The tethered αDTX maintained channel specificity. Drosophila Kv1.1 (Shaker) and rat Kv1.2 are closely related channels but differ in their sensitivity to αDTX (Kv1.1: >1 µM, Kv1.2: 2 nM (see Gasparini et al., (1998) J Biol Chem 273, 25393-25403). Results of studies performed using various channels demonstrated that illumination with blue light only increased whole cell $K^+$ currents in PC-12 expressing Kv1.2, but not Kv1.1 (FIG. 3C).

In additional studies, Lighands were found to be compatible with other optogenetic methods such as green and orange light-activated silencers, as illumination with orange (535 nm) light did not modulate Lighand activity (FIG. 3D). The $\tau_{on}$ after illumination was light power-dependent and on the order of 1-4 sec. LOV2 domains are supremely light sensitive and as little as 10 µW/mm² yielded robust activation (FIG. 3E, left panel). It was instructive to compare this to "traditional" optogenetic tools such as Channelrhodopsin 2, which is routinely driven by 5000 µW/mm². The mean value of $\tau_{off}$ for reverting to the dark state, 50 sec, does not vary with light power (FIG. 3E, right panel). Both $\tau_{on}$ and $\tau_{off}$ were very similar to those of the isolated LOV2 [Salomon, M. et al., (2000) Biochem 39, 9401-9410; and Christie, J. M. et al., (2007) Biochem 46, 9310-9319], and the dynamics of the LOV2 may have been rate limiting for the kinetics of the tethered peptide toxin. Lighands of the invention may be further engineered using extensive research on LOV-related plant photoreceptors, to produced additional optimized Lighand [see for example LOV information set forth in Moglich, A. and Moffat, K., (2010) Photochem Photobiol Sci. October 28; 9(10):1286-300].

Figure 4:
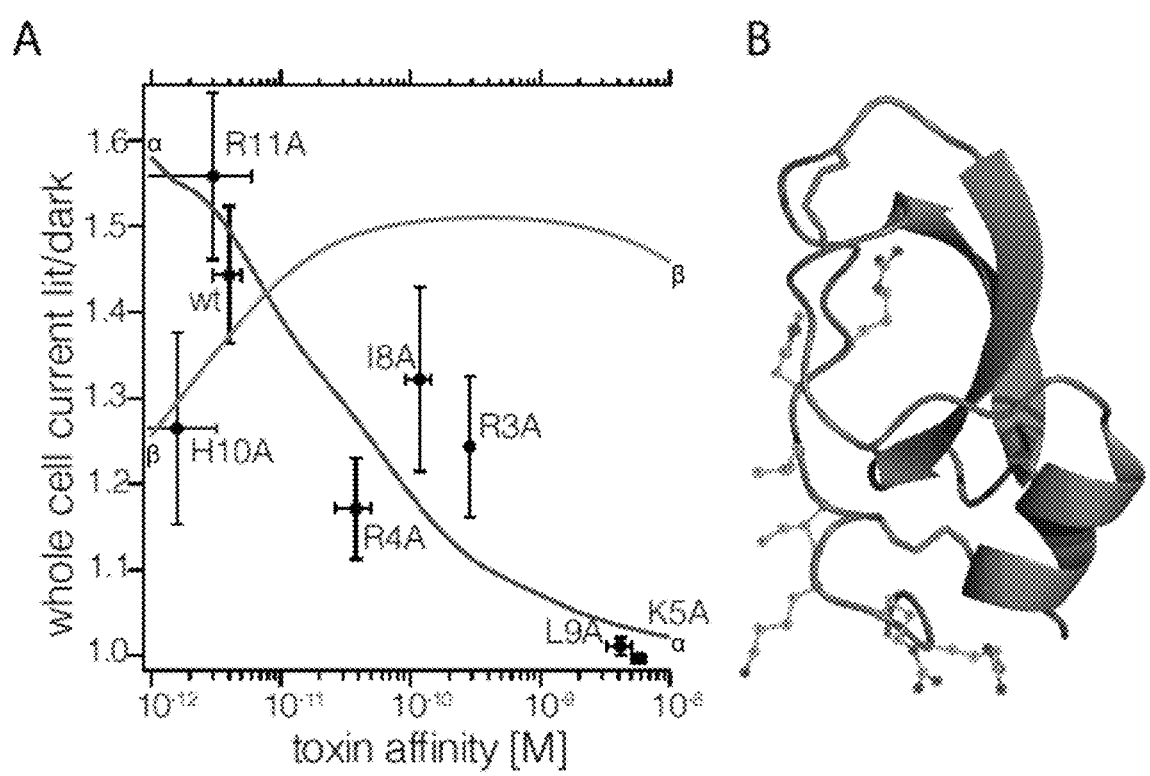
FIG. 4 provides a graph and a drawing of a protein structure illustrating that Lighand efficacy is tunable by rational protein design.

Further investigations were performed to determine whether mutation in αDTX known to alter the affinity toward the target channel Kv1.2 could be used to tune the response of Lighands in a predictive manner. High-affinity binding of αDTX depends crucially on the residues K5 and L9, and changing these residues to alanine decreases the KD by three orders of magnitude [see Gasparini, S. et al., (1998) J Biol Chem 273, 25393-25403]. In the context of Lighand-encoded αDTX blocking Kv1.2 in the dark (off) state, the effect of these two corresponding mutations was examined. Testing of the mutated Lighands showed that in the presence of the mutations the baseline of $K^+$ current increased, because fewer channels were blocked. In addition, the activation ratio (Ilit/Idark) decreased as fewer channels were now primed to become unmasked. Results are shown in FIG. 4A. It was determined that both baseline current and activation ratio monotonically depended on apparent toxin affinity, which had been determined with free, (non-tethered) toxin. Results showed that the Lighand-encoded peptide toxins maintained their activity when part of a synthetic fusion protein.

The second generation of tethered αDTX Lighands were also characterized in cultured primary neurons to confirm whether the Ligand's basic properties transferred from PC-12 cells to nervous tissue.

Figure 5:
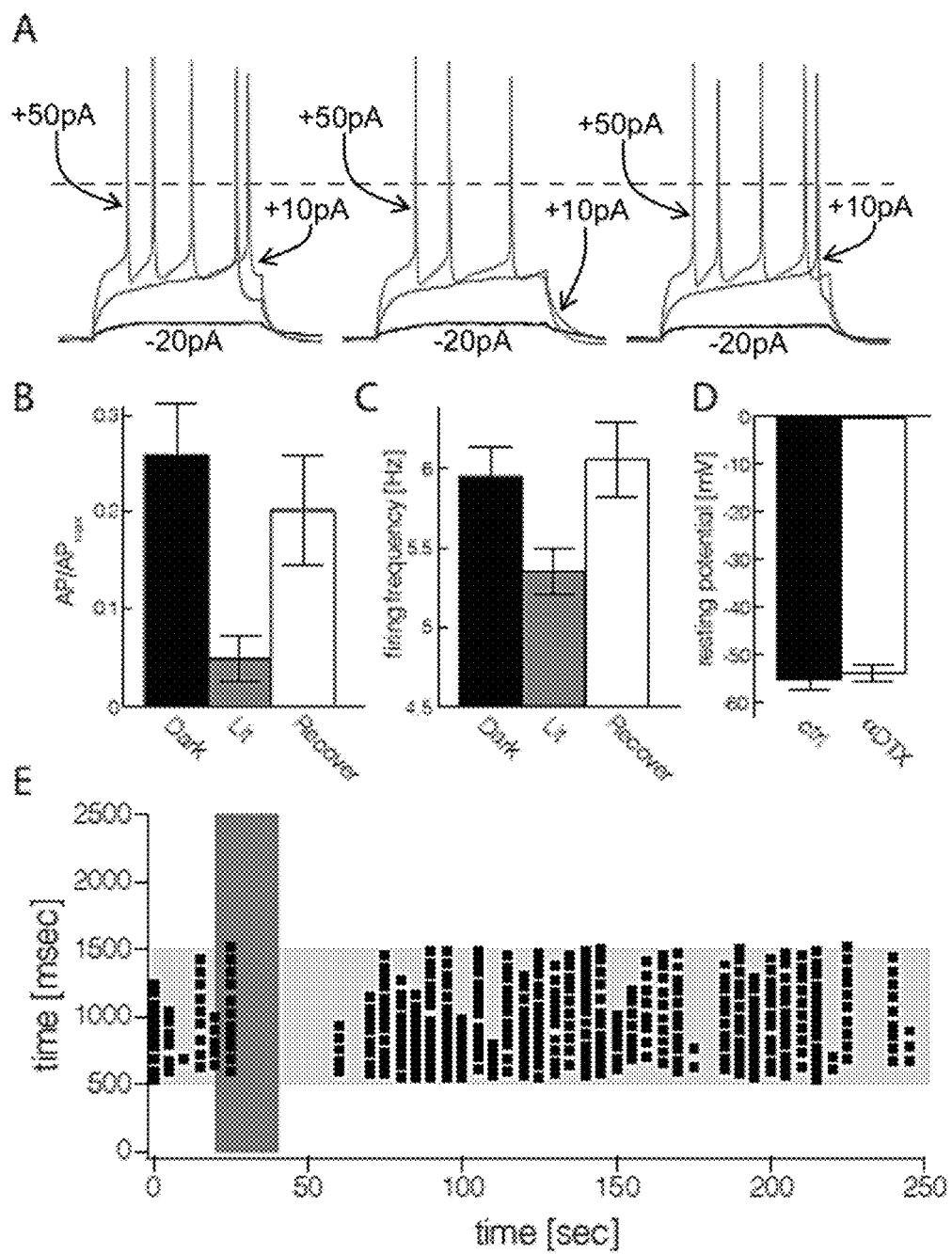
FIG. 5 provides traces and graphs illustrating results showing that αDTX Lighand modulated excitability in cultured primary neurons.

In the context of a neuron firing action potentials after injection of somatic current, an increase in Kv1 mediated $K^+$ current will lead to a decrease in excitability. It was observed that illumination with 455 nm light transiently abolished action potentials in response to somatic current injection (FIG. 5A,E). After the illumination stopped, the neuron reverted to dark state firing patterns and increased excitability. Spike frequency was decreased during illumination and recovered to pre-illumination levels shortly after cessation of light exposure (FIG. 5B,C). Importantly, expressing Ligands in cultured neurons did not impair cell health as evidenced by an unchanged resting potential compared to mock transfected neurons (FIG. 5D).

Results

The studies demonstrated the implementation of a modular system of reagents, termed Lighands, that are genetically encoded, cell autonomous, light-switchable modulators of cellular ion channels and receptors. The Lighands, or light-modulated fusion proteins based on a combination of three components including (1) a peptide ligand that modulates ion channels and receptors, (2) a linker, and (3) a photoreceptor that undergoes a well understood and reversible conformational change when illumined, thereby changing the peptide ligands local concentration, and two optional components (4) a membrane anchor that ensures cell autonomous function, and (5) a secretions signal that targets a synthetic fusion protein to the secretory pathway.

An example implementation that included the five components was able to modulate whole cell $K^+$ current with a co-expressed ion channel, rat Kv1.2 but not Shaker Kv1.1, which demonstrated that under the test conditions, the peptide toxins, when part of a membrane-tether fusion protein, retained their activity and most importantly their specificity. Peptide toxins' specificity has made them an invaluable tool for neuroscience of the last several decades. Because the Lighand reagents are modular by design, they can be used in conjunction with the rich foundation of toxin knowledge and, by swapping out peptide ligands, it was found that it is possible to rationally engineer novel molecular Lighand reagents toward specific cellular targets as well as finely tune their function.

It was determined that Lighands containing the AsLOV2 photoreceptor could be switched by very small, $\mu W/mm^2$, light powers allowing for large volumes of tissue to be affected. In addition, the relatively narrow action spectrum (430-470 nm) of modulating light makes Lighands compatible with other optogenetic control techniques such as opsin-based silencers of cellular signaling. The Lighands were able to be expressed in cultured neurons their excitability modulated by affecting endogenous Kv1 channels. There are many advantages to modulate endogenous ion channels. The methods allow for more naturalistic perturbation without the associated side-effects of current optogenetic technology (rebound firing, shifts in ion homeostasis [see Raimondo, J. V. et al., (2012) Neurosci 15, 1102-1104].

Lighands also offer more precision when compared to other fully genetically encoded optogenetic reagent that broadly affect many ionic conductances [see Ferenczi, E. and Deisseroth, K., (2012) Nat Neurosci 15, 1058-1060]. Signaling patterns of many cells, especially neurons, are governed by a specific and localized complement of ion channels and receptors. The light-modulated fusion proteins of the invention can be targeted to a very specific part of that channel and receptor complement, and for Lighands tools permit, for the first time, study of the reliance of cellular signaling on this part in a dynamic fashion. The Lighands can be used to accelerate biological and biomedical research, to open up new frontiers on understanding the causal processes that drive health problems, and for development and treatment of disease.

Example 2

A fusion protein that comprises the following components is expressed in a cell and tested to determine the effect of the resulting Lighand on a channel or receptor itself for which iberiotoxin is a ligand.
Domains of the Fusion Protein
1. a secretion Signal
2. Iberiotoxin QFTDVDCSVSKECWSVCKDLF-GVDRGKCMGKKCRCYQ (SEQ ID NO:66)
3. a Linker(GSG)n (where n=1, 2, 3, 4, 5, 6, 7, 8, 9, or 10)
4. an AsLOV2 polypeptide
5. a BKCA alpha polypeptide (e.g., derived from KCMA1_HUMAN, Uniprot Q12791)
The expressed Lighand is contacted with light and the ion conductance in the cell in which the Lighand is expressed is measured. Results show the Lighand alters ion conductance activity of the channel in response to contact with light.

Example 3

A fusion protein that comprises the following components is expressed in a cell and tested to determine the effect of the resulting Lighand on a channel or receptor itself for which αDTX is a ligand.
Domains of the Fusion Protein (the Lighand)
1. A secretion Signal
2. An αDTX (see sequence provided above)
3. A linker (GSG)n (where n-=1, 2, 3, 4, 5, 6, 7, 8, 9, or 10)
4. An AsLOV2 polypeptide
5. A KChip1 polypeptide (e.g., derived from KCIP1_HUMAN, Uniprot Q9NZI2)
The expressed Lighand is contacted with light and the ion conductance in the cell in which the Lighand is expressed is measured. Results show the Lighand alters ion conductance activity of the channel in response to contact with light.

Example 4

Synthetic membrane-tethered fusion proteins containing ion channel/receptor blockers or modulators connected to a plant photoreceptor domain via an amino acid linker of varying length were prepared and used to alter the ionic conductances of excitable cells with light.

Membrane-tethered ion channel/receptor modulators that are optogenetic (light-controlled, genetically encodable) were prepared by engineering fusion proteins that contained a peptide ligand (the modulator), a flexible linker; a photoreceptor domain (the light switch), a secretion signal polypeptide; and a membrane tethering signal. In this study, a fusion protein was prepared that included a secretion signal, a peptide toxin (the modulator), a flexible linker, a plant photoreceptor domain (the light switch), and a membrane tethering signal. This fusion protein controlled the "effective availability" of the linked peptide toxin (see FIG. 6).

A membrane-tethered, light-switchable alpha-Dendrotoxin was prepared that can increase baseline excitability of neurons in response to low-intensity light exposure (see for example FIG. 2).

Peptide toxins are small disulfide-rich molecules varying in length from 12-80 amino acids. Cholinergic regulators of the Ly6 superfamily (e.g. lynx1) resemble venom peptide toxins and were anchored to cell membrane via glycosyl-phosphatidylinositol (GPI) anchors. Lynx1 colocalizes with nicotinic acetylcholine receptors and is an allosteric regulator in vivo. Prior studies have demonstrated that by using a secretion signal and consensus sequences for GPI processing of lynx1 it is possible to engineer membrane tethered toxins that are highly effective in modulation neuronal activity (see for example U.S. patent application publication US2006/0057614, incorporated herein by reference). So far around 40 tethered toxin species have been engineered based on venom peptide toxin genes and their effect on ion channels and receptors has been characterized.

Figure 6:
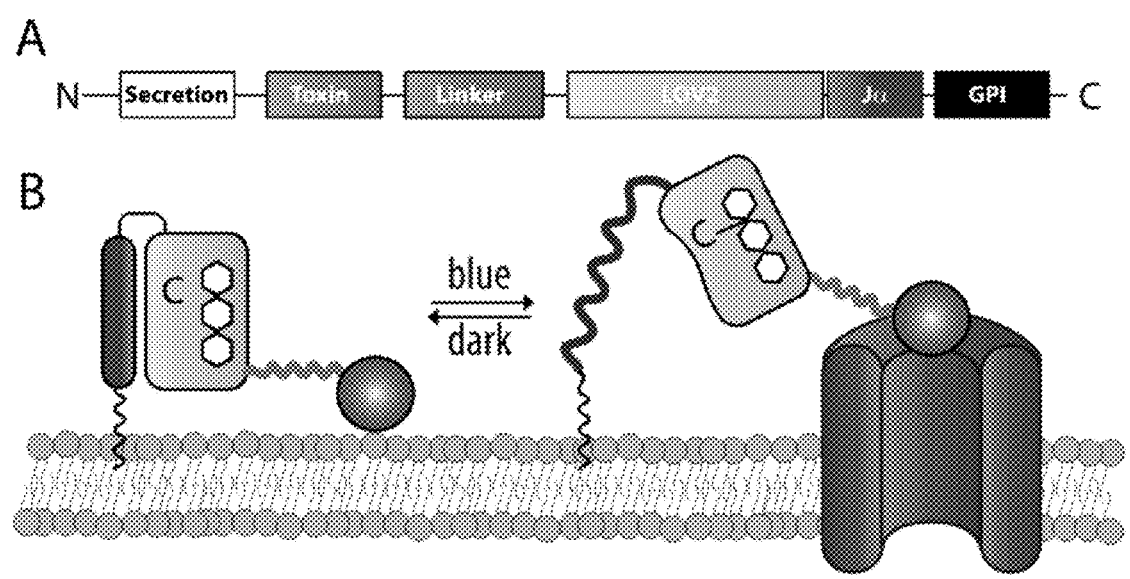
FIG. 6 illustrates a light-dependent peptide design.

To confer light-control to tethered toxins, procedures were performed that employed a class of light-dependent switch; flavin-binding light-oxygen-voltage (LOV) domain sensors found in plants, where they transduce phototropic signals. LOV domains use flavin nucleotide cofactors to detect blue light. LOV2-containing photoreceptors are usually modular in nature. LOV2 domains have a compact structure and the LOV2 domains fold independently and retain all structural and functional aspects when isolated and transplanted into different proteins. Structural studies were performed on the Avena sativa LOV2 domain and the results indicated that the C-terminal Jalpha helix reversibly unfolded upon blue light illumination (FIG. 6).

In one study, the sequence coding for a peptide toxin for example, alpha-Dendrotoxin having the amino acid sequence QPRRKLCILHRNPGRCYDKIPAFYYN-QKKKQCERFDWSGCGGNSNRFKTIEECR RTCIG (SEQ ID NO:1), and the DNA sequence: CAGCCCAGAA- GAAAGCTGTGCATCCTGCACAGAAAC-
CCCGGCAGATGCTACG ACAAGATCCCCGCCTTC-
TACTACAACCAGAAGAAGAAGCAGTGCGAGAGATT
CGACTGGAGCGGCTGCGGCGGCAACAG-
CAACAGATTCAAGACCATCGAGGA GTGCAGAA-
GAACCTGCATCGGC (SEQ ID NO:68) were expressed in cells as follows:

1) The toxin gene was cloned without stop codon into a lentiviral or adeno-associated virus (AAV) packaging plasmid, or another desired expression plasmid, and a secretion signal sequence was cloned upstream, a flexible linker in varying length, LOV2 (residues 404-546) domain from Avena sativa and GPI-anchor were cloned downstream, thus creating a fusion protein (see FIG. 6).
2) The viral or expression plasmid contained either a strong general promoter, a cell-specific promoter, or a strong general promoter followed by one more logical elements (such as a lox-stop-lox sequence, which was removed by Cre recombinase selectively expressed in cells in a transgenic animal, or in a second virus, thus enabling the strong general promoter to then drive the gene).
3) When using a viral plasmid, the viral vector was synthesized using the viral plasmid, using standard techniques.
4) When using a virus, as appropriate for gene therapy, the virus was injected using a small needle or cannula into the area of interest, thus delivering the gene encoding the fusion protein into the cells of interest. If using another expression vector, the vector was directly electroporated or injected into the cell or organism (for acutely expressing the fusion protein, or making a cell line, or a transgenic mouse or other animal).
5) The fusion was illuminated with light using peak illumination wavelength of about 455 nm.
6) The above wavelengths illustrate typical modes of operation, but are not meant to constrain the protocols that can be used. Either narrower or broader wavelengths, or differently-centered illumination spectra, can be used. For prosthetic uses, the devices used to deliver light may be implanted (for example using LED or fiber arrays). For drug screening, a xenon lamp or LED can be used to deliver the light.

It is to be understood that the methods, compositions, and apparatus which have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all literature references, patents, and published patent applications cited throughout this application are incorporated herein by reference in their entirety.

We claim:

1. A fusion protein comprising a peptide ligand domain, a linker polypeptide domain, a photoreceptor polypeptide domain, and a membrane-anchoring polypeptide domain, wherein the peptide ligand is a ligand for an ion channel or receptor, the photoreceptor polypeptide domain is a light-oxygen-voltage (LOV) domain, and the binding specificity of the peptide ligand domain for its cognate channel or receptor is maintained in the presence and absence of a light that alters the conformation of the photoreceptor polypeptide domain.

2. The fusion protein of claim 1, further comprising a trafficking signal polypeptide domain.

3. The fusion protein of claim 2 wherein the trafficking signal is a secretion signal.

4. The fusion protein of claim 1, wherein the membrane-anchoring polypeptide domain comprises a glycophosphatidylinositol (GPI) anchoring polypeptide, a one-pass transmembrane polypeptide, a channel complex-anchoring polypeptide, or a channel complex partner anchoring polypeptide.

5. The fusion protein of claim 3, wherein the secretion signal polypeptide domain comprises a polypeptide derived from a truncated MHC I antigen (ss) polypeptide, a prolactin (prl) polypeptide, an achR beta subunit (acr) polypeptide, or a serine protease I (srl) polypeptide.

6. The fusion protein of claim 1, wherein the photoreceptor polypeptide domain comprises an amino acid sequence derived from an amino acid sequence of a plant photoreceptor polypeptide.

7. The fusion protein of claim 1, further comprising a reporter molecule polypeptide domain.

8. A composition comprising the fusion protein of claim 1 and a pharmaceutical carrier.

9. A cell comprising the fusion protein of claim 1, wherein the cell is an in vitro cell.

10. The cell of claim 9, wherein the cell is an excitable cell.

11. A pharmaceutical composition comprising the fusion protein molecule of claim 1.

12. A polynucleotide molecule that encodes the fusion protein of claim 1.

13. An expression vector comprising the polynucleotide molecule of claim 12.

14. An in vitro cell comprising the polynucleotide molecule of claim 12.

15. A method of modulating a functional state of an ion channel in a cell membrane, the method comprising,
expressing in a cell comprising a cell membrane ion channel, a fusion protein comprising a polypeptide ligand domain, a linker polypeptide domain, a membrane-anchoring polypeptide domain, and a photoreceptor polypeptide domain, wherein the ligand is a ligand for the ion channel, the photoreceptor polypeptide domain is a light-oxygen-voltage (LOV) domain, and the binding specificity of the peptide ligand domain for its cognate channel or receptor is maintained in the presence and absence of a light that alters the conformation of the photoreceptor polypeptide domain; and
contacting the expressed fusion protein with an effective dose of a light to modulate a conformation of the fusion protein, wherein the modulation of the conformation of the fusion protein alters a functional state of the ion channel in the membrane.

16. A method of determining the effect of a candidate therapeutic compound on a functional state of an ion channel of a membrane, the method comprising,
expressing in a cell comprising a cell membrane ion channel, a fusion protein comprising a polypeptide ligand domain, a linker polypeptide domain, a membrane-anchoring polypeptide domain, and a photoreceptor polypeptide domain, wherein the polypeptide ligand is a ligand for the ion channel, the photoreceptor polypeptide domain is a light-oxygen-voltage (LOV) domain, and the binding specificity of the peptide ligand domain for its cognate channel or receptor is maintained in the presence and absence of a light that alters the conformation of the photoreceptor polypeptide domain;
contacting the cell with a candidate therapeutic compound;
contacting the expressed fusion protein with a dose of a light effective to modulate a conformation of the fusion protein;
determining the functional state of the ion channel; and
comparing the determined functional state of the ion channel with a control functional state of the ion channel, wherein a difference between the determined functional state and the control functional state indicates an effect of the candidate therapeutic compound on the functional state of the ion channel.

17. The fusion protein of claim 1, wherein the membrane is a plasma membrane.

18. The fusion protein of claim 1, further comprising a secretion signal polypeptide domain.

19. The fusion protein of claim 18, wherein the membrane is a plasma membrane.

20. The fusion protein of claim 1, wherein the linker polypeptide domain comprises a flexible linker.

21. The fusion protein of claim 7, wherein the reporter molecule polypeptide domain comprises a fluorescent reporter polypeptide.

* * * * *